(12) United States Patent
Koch et al.

(10) Patent No.: US 7,538,120 B2
(45) Date of Patent: *May 26, 2009

(54) METHOD OF TREATING INFLAMMATORY DISEASES

(75) Inventors: Kevin Koch, Boulder, CO (US); T. Brian Hurley, Boston, MA (US); Hong Woon Yang, Superior, CO (US); Joseph Lyssikatos, Superior, CO (US); James F. Blake, Longmont, CO (US); Allison L. Marlow, Louisville, CO (US); Eli M. Wallace, Lyons, CO (US)

(73) Assignee: Array Biopharma Inc., Boulder, CO (US)

( * ) Notice: Subject to any disclaimer, the term of this patent is extended or adjusted under 35 U.S.C. 154(b) by 307 days.

This patent is subject to a terminal disclaimer.

(21) Appl. No.: 11/208,442

(22) Filed: Aug. 19, 2005

(65) Prior Publication Data

US 2006/0030610 A1    Feb. 9, 2006

Related U.S. Application Data

(63) Continuation-in-part of application No. 10/929,295, filed on Aug. 30, 2004, now Pat. No. 7,230,099, which is a continuation-in-part of application No. 10/654,580, filed on Sep. 3, 2003, now Pat. No. 7,144,907.

(51) Int. Cl.
 *A61K 31/44* (2006.01)
(52) U.S. Cl. ...................................... 514/300
(58) Field of Classification Search .................. 514/382, 514/300
 See application file for complete search history.

(56) References Cited

U.S. PATENT DOCUMENTS

| | | | |
|---|---|---|---|
| 5,525,625 A | 6/1996 | Bridges et al. | |
| 6,310,060 B1 | 10/2001 | Barrett et al. | |
| 6,469,004 B1 | 10/2002 | Barrett et al. | |
| 6,506,798 B1 | 1/2003 | Barrett et al. | |
| 7,230,099 B2 * | 6/2007 | Wallace et al. | 544/127 |
| 2003/0004193 A1 | 1/2003 | Barrett et al. | |
| 2003/0045521 A1 | 3/2003 | Tecle | |
| 2003/0078428 A1 | 4/2003 | Barrett et al. | |
| 2003/0092748 A1 | 5/2003 | Barrett et al. | |
| 2003/0216460 A1 | 11/2003 | Wallace et al. | |
| 2003/0232869 A1 | 12/2003 | Wallace et al. | |
| 2004/0116710 A1 | 6/2004 | Wallace et al. | |
| 2005/0049276 A1 | 3/2005 | Kaufman et al. | |

FOREIGN PATENT DOCUMENTS

| | | |
|---|---|---|
| EP | 0 602 242 A1 | 6/1994 |
| WO | WO 92/03286 A1 | 2/1995 |
| WO | WO 98/43960 A1 | 10/1998 |
| WO | WO 99/01421 A1 | 1/1999 |
| WO | WO 99/01426 A1 | 1/1999 |
| WO | WO 00/40235 A2 | 7/2000 |
| WO | WO 00/40237 A1 | 7/2000 |
| WO | WO 00/41505 A2 | 7/2000 |
| WO | WO 00/41994 A1 | 7/2000 |
| WO | WO 00/42002 A1 | 7/2000 |
| WO | WO 00/42003 A1 | 7/2000 |
| WO | WO 00/42022 A1 | 7/2000 |
| WO | WO 00/42029 A1 | 7/2000 |
| WO | WO 00/68201 A1 | 11/2000 |
| WO | WO 01/05390 A2 | 1/2001 |
| WO | WO 01/05391 A2 | 1/2001 |
| WO | WO 01/05392 A2 | 1/2001 |
| WO | WO 01/05393 A2 | 1/2001 |
| WO | WO 01/68619 A1 | 9/2001 |
| WO | WO 02/06213 A2 | 1/2002 |
| WO | WO 02/18319 A1 | 3/2002 |
| WO | WO 02/44166 A1 | 6/2002 |
| WO | WO 03/077855 A2 | 9/2003 |
| WO | WO 03/077914 A1 | 9/2003 |

OTHER PUBLICATIONS

Marteau et al. "Protection from gastrointestinal diseases with the use of probiotics". The American Journal of Clinical Nutrition. 2001. vol. 73 (suppl). pp. 430S-436S.*

* cited by examiner

*Primary Examiner*—Raymond J Henley, III
(74) *Attorney, Agent, or Firm*—John R. Moore; Hogan & Hartson

(57) ABSTRACT

Disclosed are methods of treating inflammatory diseases and disorders, such as arthritis and inflammatory bowel disease, in mammals.

9 Claims, 19 Drawing Sheets

METHOD OF TREATING INFLAMMATORY DISEASES

CROSS-REFERENCE TO RELATED APPLICATIONS

This application is a Continuation-in-Part application of U.S. patent application Ser. No. 10/929,295, filed Aug. 30, 2004 now U.S. Pat. No. 7,230,099, which is a Continuation-in-Part application of U.S. patent application Ser. No. 10/654,580, filed Sep. 3, 2003 now U.S. Pat. No. 7,144,907, each of which is incorporated herein by reference in its entirety.

BACKGROUND OF THE INVENTION

1. Field of the Invention

This invention relates to methods for treating inflammatory diseases and disorders in mammals, especially humans, which method comprises administering an effective amount of a MEK inhibitor to a mammal in need of such treatment.

2. Description of the State of the Art

Cell signaling through growth factor receptors and protein kinases is an important regulator of cell growth, proliferation and differentiation. In normal cell growth, growth factors, through receptor activation (i.e. PDGF or EGF and others), activate MAP kinase pathways. One of the most important and most well understood MAP kinase pathways involved in normal and uncontrolled cell growth is the Ras/Raf kinase pathway. Active GTP-bound Ras results in the activation and indirect phosphorylation of Raf kinase. Raf then phosphorylates MEK1 and 2 on two serine residues (S218 and S222 for MEK1 and S222 and S226 for MEK2) (Ahn et al., *Methods in Enzymology*, 2001, 332, 417-431). Activated MEK then phosphorylates its only known substrates, the MAP kinases ERK1 and 2. ERK phosphorylation by MEK occurs on Y204 and T202 for ERK1 and Y185 and T183 for ERK2 (Ahn et al., *Methods in Enzymology*, 2001, 332, 417-431). Phosphorylated ERK dimerizes and then translocates to the nucleus where it accumulates (Khokhlatchev et al., *Cell*, 1998, 93, 605-615). In the nucleus, ERK is involved in several important cellular functions, including but not limited to nuclear transport, signal transduction, DNA repair, nucleosome assembly and translocation, and mRNA processing and translation (Ahn et al., *Molecular Cell*, 2000, 6, 1343-1354). Overall, treatment of cells with growth factors leads to the activation of ERK1 and 2 which results in proliferation and, in some cases, differentiation (Lewis et al., *Adv. Cancer Res.*, 1998, 74, 49-139).

In proliferative diseases, genetic mutations and/or overexpression of growth factor receptors, downstream signaling proteins, or protein kinases involved in the ERK kinase pathway lead to uncontrolled cell proliferation and, eventually, tumor formation. For example, some cancers contain mutations which result in the continuous activation of this pathway due to continuous production of growth factors. Other mutations can lead to defects in the deactivation of the activated GTP-bound Ras complex, again resulting in activation of the MAP kinase pathway. Mutated, oncogenic forms of Ras are found in 50% of colon and >90% pancreatic cancers as well as many others types of cancers (Kohl et al., *Science*, 1993, 260, 1834-1837). Recently, bRaf mutations have been identified in more than 60% of malignant melanoma (Davies, H. et al., *Nature*, 2002, 417, 949-954). These mutations in bRaf result in a constitutively active MAP kinase cascade. Studies of primary tumor samples and cell lines have also shown constitutive or overactivation of the MAP kinase pathway in cancers of pancreas, colon, lung, ovary and kidney (Hoshino, R. et al., *Oncogene*, 1999, 18, 813-822). Hence, there is a strong correlation between cancers and an overactive MAP kinase pathway resulting from genetic mutations.

Since constitutive or overactivation of MAP kinase cascade plays a pivotal role in cell proliferation and differentiation, inhibition of this pathway is believed to be beneficial in hyperproliferative diseases. MEK is a key player in this pathway as it is downstream of Ras and Raf. Additionally, it is an attractive therapeutic target because the only known substrates for MEK phosphorylation are the MAP kinases, ERK1 and 2. Inhibition of MEK has been shown to have potential therapeutic benefit in several studies. For example, small molecule MEK inhibitors have been shown to inhibit human tumor growth in nude mouse xenografts, (Sebolt-Leopold et al., *Nature-Medicine*, 1999, 5 (7), 810-816; Trachet et al., AACR Apr. 6-10, 2002, Poster #5426; Tecle, H., IBC $2^{nd}$ International Conference of Protein Kinases, Sep. 9-10, 2002), block static allodynia in animals (WO 01/05390 published Jan. 25, 2001) and inhibit growth of acute myeloid leukemia cells (Milella et al., *J. Clin. Invest.*, 2001, 108 (6), 851-859).

Small molecule inhibitors of MEK have been recently disclosed. See, for example, U.S. Pat. No. 5,525,625; WO 98/43960; WO 99/01421; WO 99/01426; WO 00/41505; WO 00/42002; WO 00/42003; WO 00/41994; WO 00/42022; WO 00/42029; WO 00/68201; WO 01/68619; and WO 02/06213.

SUMMARY OF THE INVENTION

This invention provides methods for treating an inflammatory disease or disorder in a mammal, such as a human, which methods comprise administering a MEK inhibitor to a mammal in need of such treatment.

Examples of MEK inhibitors suitable for use in the methods of this invention include compounds of Formula I and solvates, metabolites, and pharmaceutically acceptable salts and prodrugs thereof

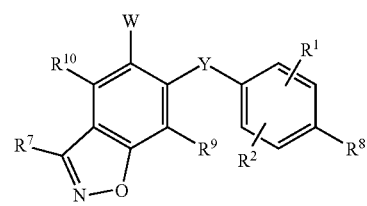

I wherein:

$R^1$, $R^2$, $R^7$, $R^8$, $R^9$, and $R^{10}$ are independently hydrogen, halo, cyano, nitro, trifluoromethyl, difluoromethoxy, trifluoromethoxy, azido, —$OR^3$, —$C(O)R^3$, —$C(O)OR^3$, $NR^4C(O)OR^6$, —$OC(O)R^3$, —$NR^4SO_2R^6$, —$SO_2NR^3R^4$, —$NR^4C(O)R^3$, —$C(O)NR^3R^4$, —$NR^5C(O)NR^3R^4$, —$NR^5C(NCN)NR^3R^4$, —$NR^3R^4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —$S(O)_j$ ($C_1$-$C_6$ alkyl), —$S(O)_j(CR^4R^5)_m$-aryl, aryl, arylalkyl, heteroaryl, heteroarylalkyl, heterocyclyl, heterocyclylalkyl, —$O(CR^4R^{5'})_m$-aryl, —$NR^4(CR^4R^5)_m$-aryl, —$O(CR^4R^5)_m$-heteroaryl, —$NR^4(CR^4R^5)_m$-heteroaryl, —$O(CR^4R^5)_m$-heterocyclyl or —$NR^4(CR^4R^5)_m$-heterocyclyl, wherein said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halo, cyano, nitro, trifluoromethyl, difluoromethoxy, trifluoromethoxy, azido, —$NR^4SO_2R^6$, —SO$_2$NR$^3$R$^4$, —C(O)R$^3$, —C(O)OR$^3$, —OC(O)R$^3$, —NR$^4$C(O)OR$^6$, —NR$^4$C(O)R$^3$, —C(O)NR$^3$R$^4$, —NR$^3$R$^4$, —NR$^5$C(O)NR$^3$R$^4$, —NR$^5$C(NCN)NR$^3$R$^4$, —OR$^3$, aryl, heteroaryl, arylalkyl, heteroarylalkyl, heterocyclyl, and heterocyclylalkyl;

R$^3$ is hydrogen, trifluoromethyl, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, aryl, arylalkyl, heteroaryl, heteroarylalkyl, heterocyclyl, heterocyclylalkyl, phosphate, or an amino acid residue, wherein said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halo, cyano, nitro, trifluoromethyl, difluoromethoxy, trifluoromethoxy, azido, —NR'SO$_2$R'''', —SO$_2$NR'R'', —C(O)R', C(O)OR', —OC(O)R', —NR'C(O)OR'''', —NR'C(O)R'', —C(O)NR'R'', —SR', —S(O)R'''', —SO$_2$R'''', —NR'R'', —NR'C(O)NR''R''', —NR'C(NCN)NR''R''', —OR', aryl, heteroaryl, arylalkyl, heteroarylalkyl, heterocyclyl, and heterocyclylalkyl, or R$^3$ and R$^4$ together with the atom to which they are attached form a 4 to 10 membered carbocyclic, heteroaryl or heterocyclic ring, wherein said carbocyclic, heteroaryl or heterocyclic rings are optionally substituted with one or more groups independently selected from halo, cyano, nitro, trifluoromethyl, difluoromethoxy, trifluoromethoxy, azido, —NR'SO$_2$R'''', —SO$_2$NR'R'', —C(O)R', —C(O)OR', —OC(O)R', —NR'C(O)OR'''', —NR'C(O)R'', —C(O)NR'R'', —SO$_2$R'''', —NR'R'', —NR'C(O)NR''R''', —NR'C(NCN)NR''R''', —OR', aryl, heteroaryl, arylalkyl, heteroarylalkyl, heterocyclyl, and heterocyclylalkyl;

R', R'' and R''' are independently hydrogen, lower alkyl, lower alkenyl, aryl or arylalkyl, and R'''' is lower alkyl, lower alkenyl, aryl or arylalkyl, or any two of R', R'', R''' and R'''' together with the atoms to which they are attached form a 4 to 10 membered carbocyclic, heteroaryl or heterocyclic ring, wherein said alkyl, alkenyl, aryl, arylalkyl carbocyclic rings, heteroaryl rings or heterocyclic rings are optionally substituted with one or more groups independently selected from halo, cyano, nitro, trifluoromethyl, difluoromethoxy, trifluoromethoxy, azido, aryl, heteroaryl, arylalkyl, heteroarylalkyl, heterocyclyl, and heterocyclylalkyl;

R$^4$ and R$^5$ are independently hydrogen or C$_1$-C$_6$ alkyl, or

R$^4$ and R$^5$ together with the atom to which they are attached form a 4 to 10 membered carbocyclic, heteroaryl or heterocyclic ring, wherein said alkyl or said carbocyclic, heteroaryl and heterocyclic rings are optionally substituted with one or more groups independently selected from halo, cyano, nitro, trifluoromethyl, difluoromethoxy, trifluoromethoxy, azido, —NR'SO$_2$R''', —SO$_2$NR'R'', —C(O)R''', —C(O)OR', —OC(O)R', —NR'C(O)OR'''', —NR'C(O)R'', —C(O)NR'R'', —SO$_2$R'''', —NR'R'', —NR''C(O)NR''R''', —NR'C(NCN)NR''R''', —OR', aryl, heteroaryl, arylalkyl, heteroarylalkyl, heterocyclyl and heterocyclylalkyl;

R$^6$ is trifluoromethyl, C$_1$-C$_{10}$ alkyl, C$_3$-C$_{10}$ cycloalkyl, aryl, arylalkyl, heteroaryl, heteroarylalkyl, heterocyclyl, or heterocyclylalkyl, wherein said alkyl, cycloalkyl, aryl, arylalkyl, heteroaryl, heteroarylalkyl, heterocyclyl and heterocyclylalkyl portions are optionally substituted with one or more groups independently selected from oxo, halo, cyano, nitro, trifluoromethyl, difluoromethoxy, trifluoromethoxy, azido, —NR'SO$_2$R'''', —SO$_2$NR'R'', —C(O)R', —C(O)OR', —OC(O)R', —NR'C(O)OR'''', —NR'C(O)R'', —C(O)NR'R'', —SO$_2$R'''', —NR'R'', —NR'C(O)NR''R''', —NR'C(NCN)NR''R''', —OR', aryl, heteroaryl, arylalkyl, heteroarylalkyl, heterocyclyl and heterocyclylalkyl;

W is heteroaryl, heterocyclyl, —C(O)OR$^3$, —C(O)NR$^3$R$^4$, —C(O)NR$^4$OR$^3$, —C(O)R$^4$OR$^3$, —C(O)(C$_3$-C$_{10}$ cycloalkyl), —C(O)(C$_1$-C$_{10}$ alkyl), —C(O)(aryl), —C(O)(heteroaryl), —C(O)(heterocyclyl), —CONH(SO$_2$)CH$_3$ or CR$^3$OR$^3$, wherein any of said heteroaryl, heterocyclyl, —C(O)OR$^3$, —C(O)NR$^3$R$^4$, —C(O)NR$^4$OR$^3$, —C(O)R$^4$R$^3$, —C(O)(C$_3$-C$_{10}$ cycloalkyl), —C(O)(C$_1$-C$_{10}$ alkyl), —C(O)(aryl), —C(O)(heteroaryl), —C(O)(heterocyclyl), —CONH(SO$_2$)CH$_3$ and CR$^3$OR$^3$ are optionally substituted with one or more groups independently selected from —NR$^3$R$^4$, —OR$^3$, —R$^2$, C, —ClO alkyl, C$_2$-C$_{10}$ alkenyl and C$_2$-C$_{10}$ alkynyl, wherein any of said C$_1$-C$_{10}$ alkyl, C$_2$-C$_{10}$ alkenyl and C$_2$-C$_{10}$ alkynyl are optionally substituted with 1 or more groups independently selected from —NR$^3$R$^4$ and —OR$^3$;

m is 0, 1, 2, 3, 4 or 5;

j is 0, 1 or 2; and

Y is a linker.

Additional examples of MEK inhibitors suitable for use in the methods of the present invention include compounds of Formula II and solvates, metabolites, and pharmaceutically acceptable salts and prodrugs thereof

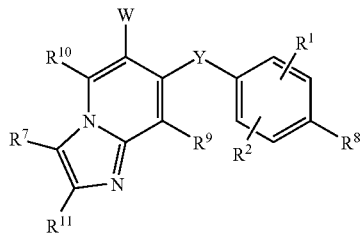

II wherein R$^1$, R$^2$, R$^7$, R$^8$, R$^9$, R$^{10}$, R''', W, and Y are as defined above, and R$^{11}$ is hydrogen, halo, cyano, nitro, trifluoromethyl, difluoromethoxy, trifluoromethoxy, azido, —OR$^3$, —C(O)R$^3$, —C(O)OR$^3$, NR$^4$C(O)OR$^6$, —OC(O)R$^3$, —NR$^4$SO$_2$R$^6$, —SO$_2$NR$^3$R$^4$, —NR$^4$C(O)R$^3$, —C(O)NR$^3$R$^4$, —NR$^5$C(O)NR$^3$R$^4$, —NR$^5$C(NCN)NR$^3$R$^4$, —NR$^3$R$^4$, C$_1$-C$_{10}$ alkyl, C$_2$-C$_{10}$ alkenyl, C$_2$-C$_{10}$ alkynyl, C$_3$-C$_{10}$ cycloalkyl, C$_3$-C$_{10}$ cycloalkylalkyl, —S(O)$_j$(C$_1$-C$_6$ alkyl), —S(O)$_j$(CR$^4$R$^5$)$_m$-aryl, aryl, arylalkyl, heteroaryl, heteroarylalkyl, heterocyclyl, heterocyclylalkyl, —O(CR$^4$R$^5$)$_m$-aryl, —NR$^4$(CR$^4$R$^5$)$_m$-aryl, —O(CR$^4$R$^5$)$_m$-heteroaryl, —NR$^4$(CR$^4$R$^5$)$_m$-heteroaryl, —O(CR$^4$R$^5$)$_m$-heterocyclyl or —NR$^4$(CR$^4$R$^5$)$_m$-heterocyclyl, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halo, cyano, nitro, trifluoromethyl, difluoromethoxy, trifluoromethoxy, azido, —NR$^4$SO$_2$R$^6$, —SO$_2$NR$^3$R$^4$, —C(O)R$^3$, —C(O)OR$^3$, —OC(O)R$^3$, —NR$^4$C(O)OR$^6$, —NR$^4$C(O)R$^3$, —C(O)NR$^3$R$^4$, —NR$^3$R$^4$, —NR$^5$C(O)NR$^3$R$^4$, —NR$^5$C(NCN)NR$^3$R$^4$, —OR$^3$, aryl, heteroaryl, arylalkyl, heteroarylalkyl, heterocyclyl and heterocyclylalkyl Additional examples of MEK inhibitors suitable for use in the methods of the present invention include compounds of Formula III and solvates, metabolites, and pharmaceutically acceptable salts and prodrugs thereof

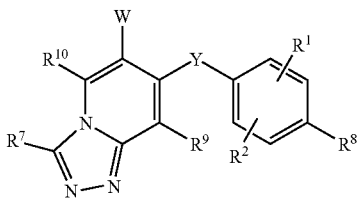

wherein $R^1, R^2, R^7, R^9, R^{10}$, W and Y are as defined above.

Additional examples of MEK inhibitors suitable for use in the methods of the present invention include compounds of Formula IV and solvates, metabolites, and pharmaceutically acceptable salts and prodrugs thereof

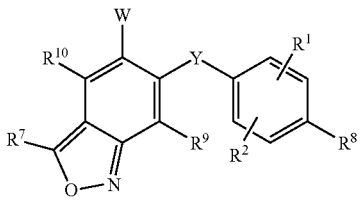

wherein $R^1, R^2, R^7, R^9, R^{10}$, W and Y are as defined above.

Additional examples of MEK inhibitors suitable for use in the methods of the present invention include compounds of Formula V and solvates, metabolites, and pharmaceutically acceptable salts and prodrugs thereof

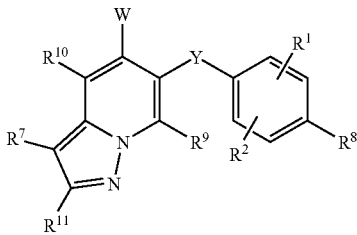

wherein $R^1$, $R^2$, $R^7$, $R^8$, $R^9$, $R^{10}$, $R^{11}$, W and Y are as defined above.

Another aspect of the present invention includes methods for treating inflammatory disorders in mammals, especially humans, which method comprises administering a composition comprising a MEK inhibitor in combination with one or more known therapeutic agents to a mammal in need of such treatment.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

BRIEF DESCRIPTION OF THE FIGURES

The accompanying drawings, which are incorporated herein and form a part of the specification, illustrate non-limiting embodiments of the present invention, and together with the description, serve to explain the principles of the invention.

In the Figures.

Figure 12:
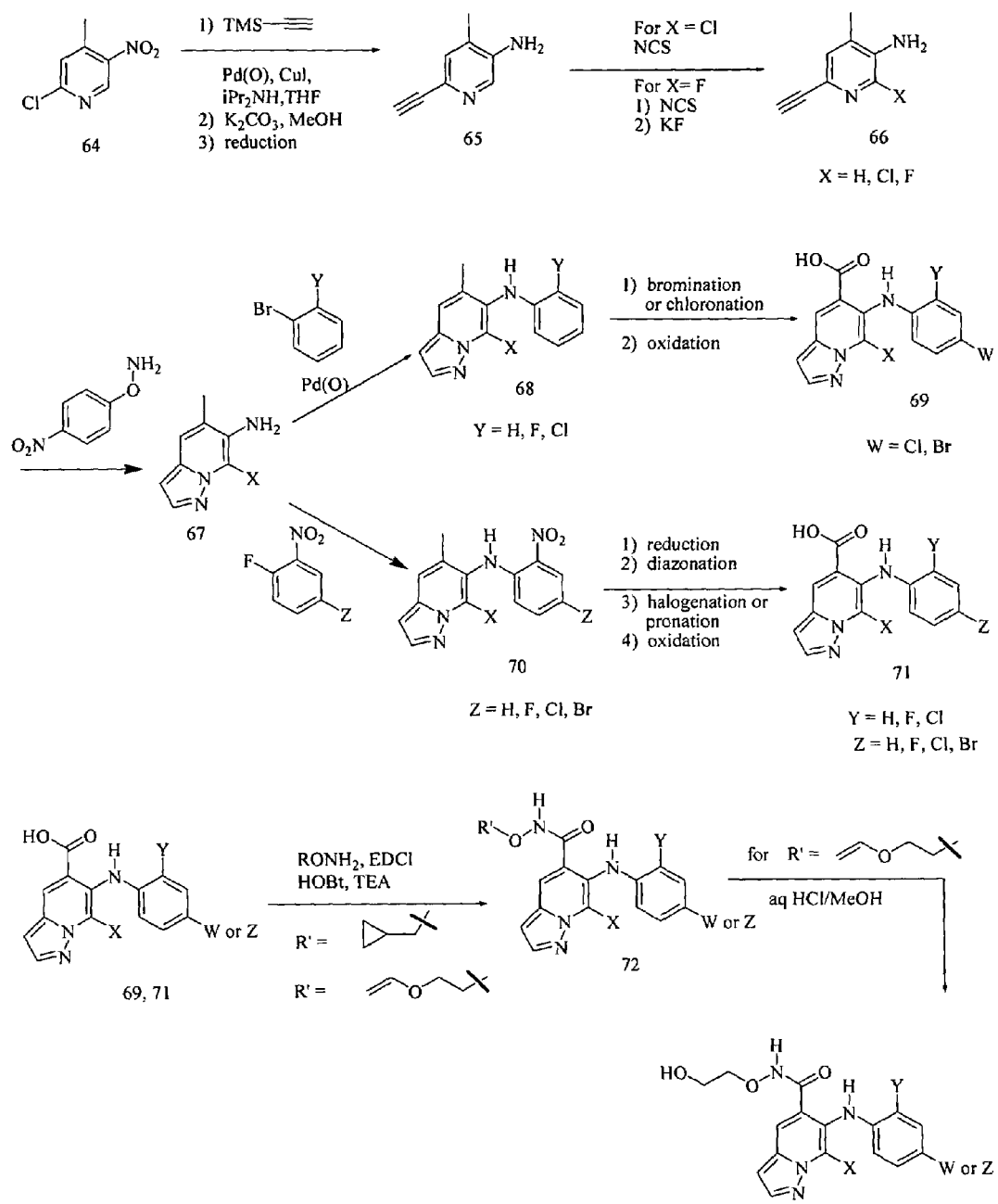
Figure 13A:
Figure 13A:
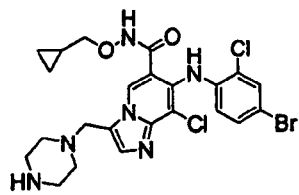
Figure 13A:
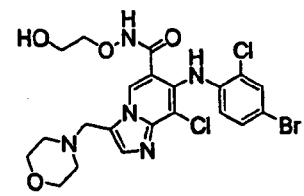
Figure 13A:
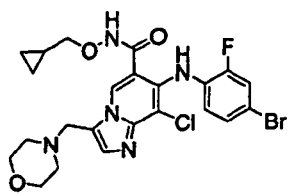
Figure 13A:
Figure 13A:
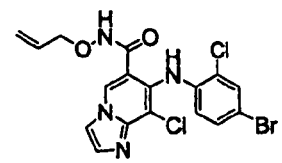
Figure 13A:
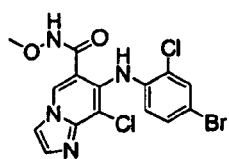
Figure 13A:
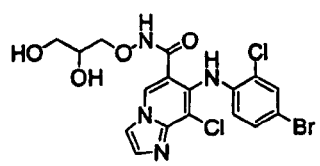
Figure 13A:
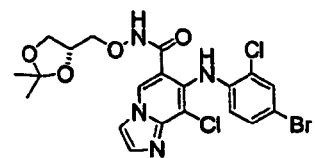
Figure 13A:
Figure 13A:
Figure 13A:
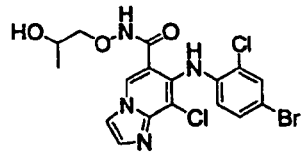
Figure 13A:
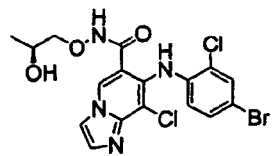
Figure 13A:
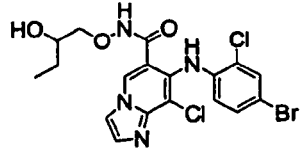
Figure 13A:
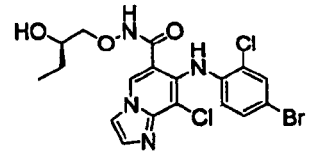
Figure 13A:
Figure 13A:
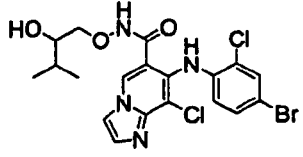
Figure 13A:
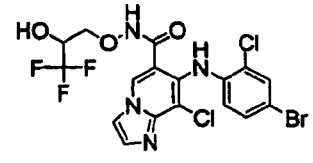
Figure 13B:
Figure 13B:
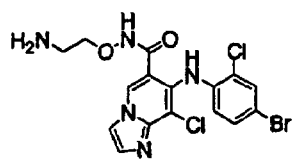
Figure 13B:
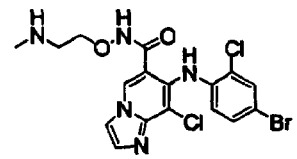
Figure 13B:
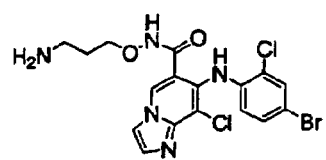
Figure 13B:
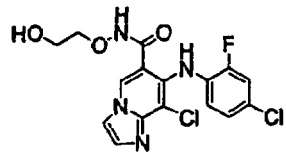
Figure 13B:
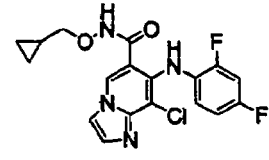
Figure 13B:
Figure 13B:
Figure 13B:
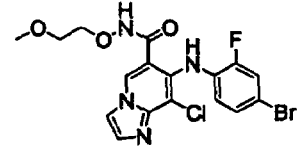
Figure 13B:
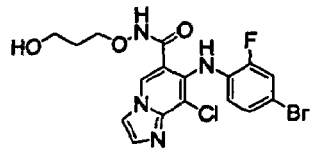
Figure 13B:
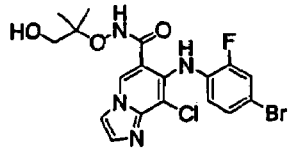
Figure 13B:
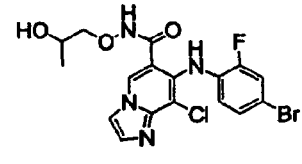
Figure 13B:
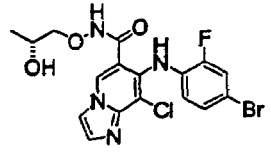
Figure 13B:
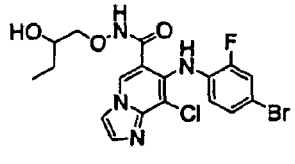
Figure 13B:
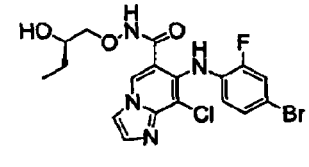
Figure 13B:
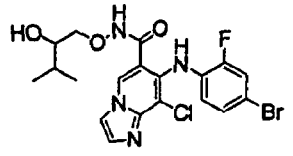
Figure 13B:
Figure 13B:
Figure 13C:
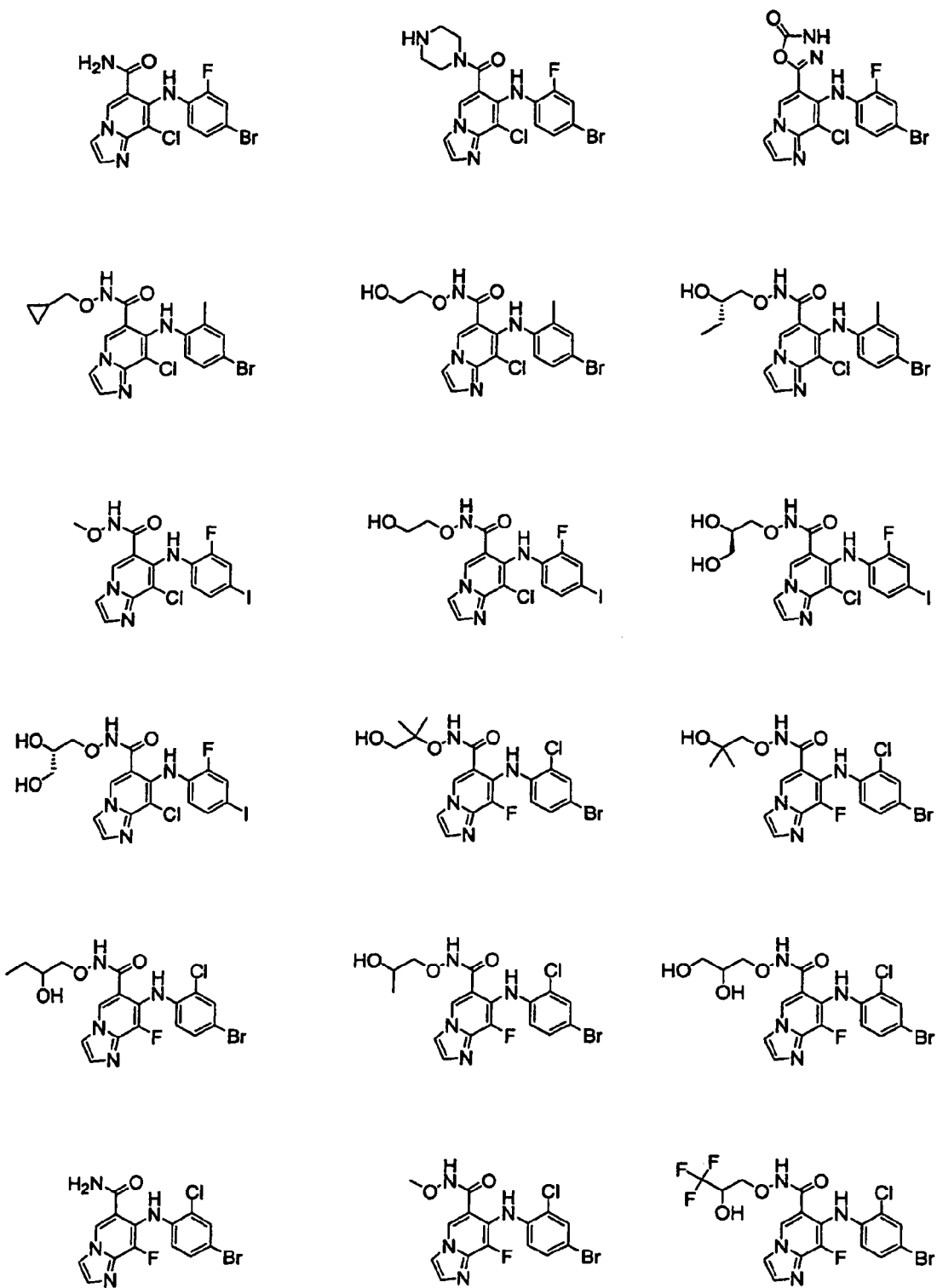
Figure 13D:
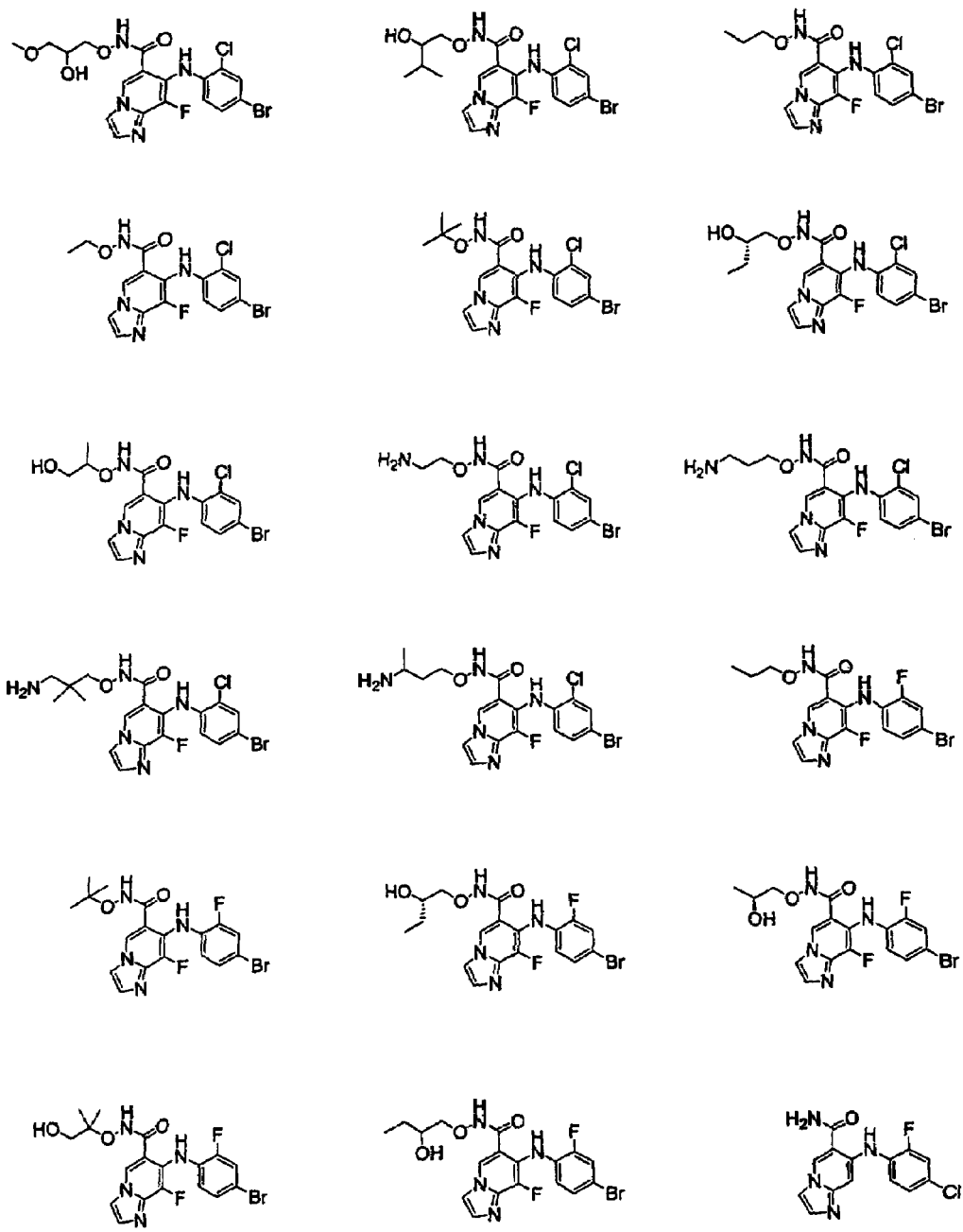
Figure 13E:
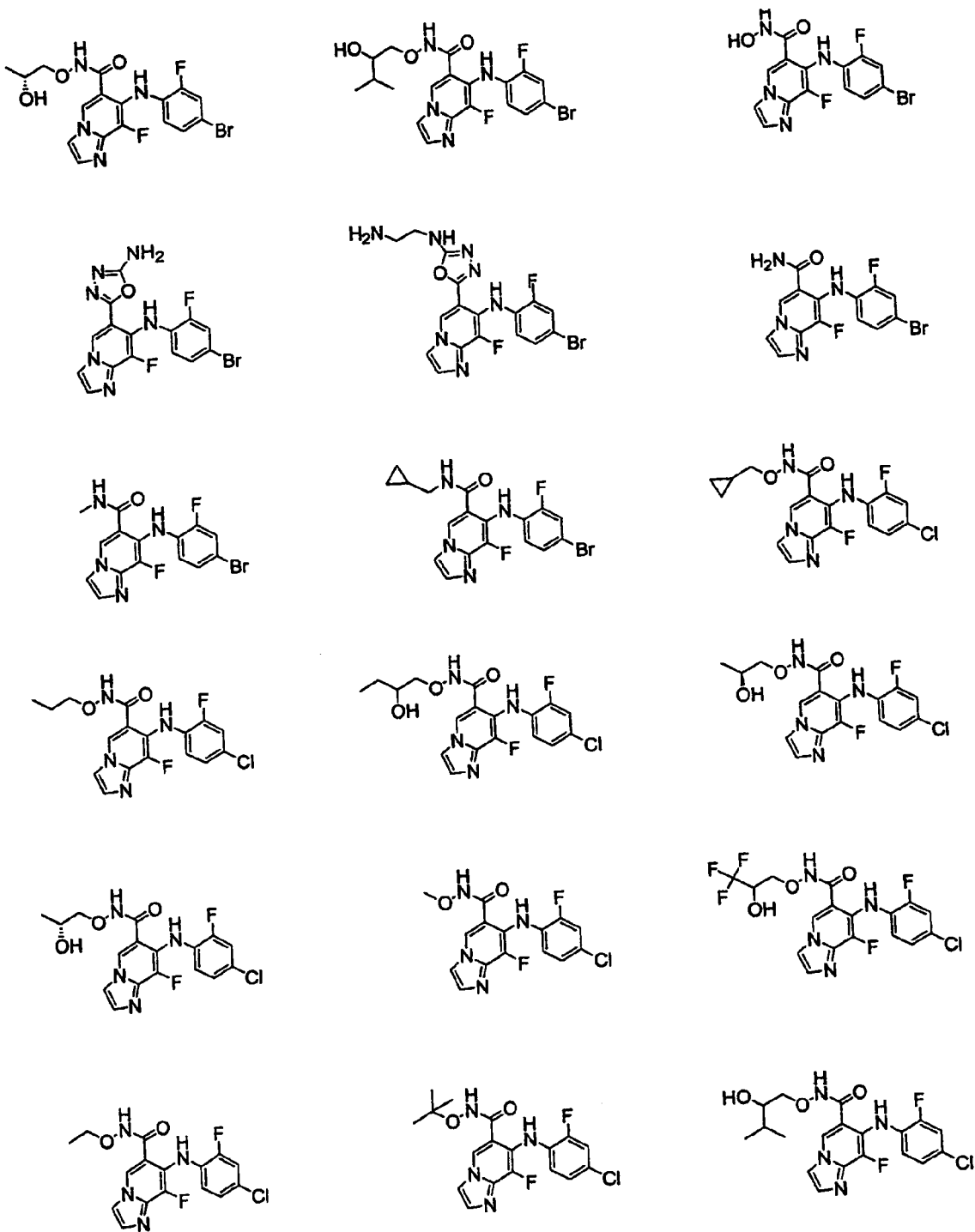
Figure 13F:
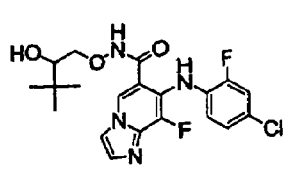
Figure 13F:
Figure 13F:
Figure 13F:
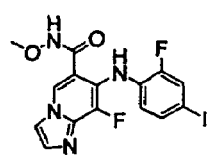
Figure 13F:
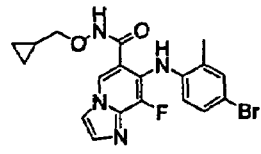
Figure 13F:
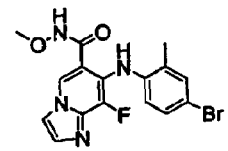
Figure 13F:
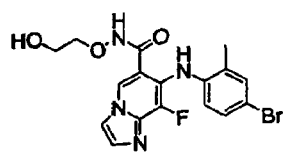
Figure 13F:
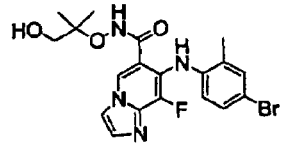
Figure 13F:
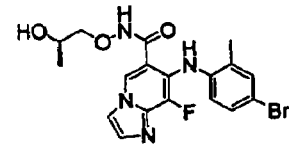
Figure 13F:
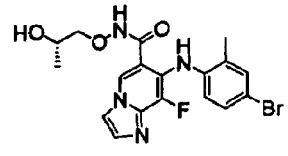
Figure 13F:
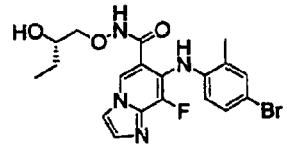
Figure 13F:
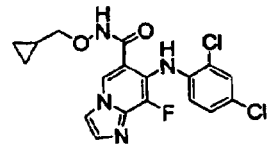
Figure 13F:
Figure 13F:
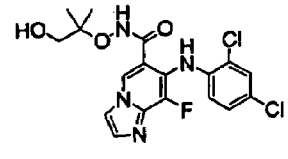
Figure 13F:
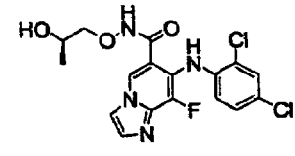
Figure 13F:
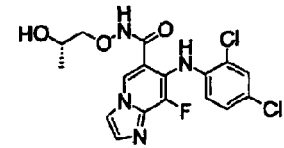
Figure 13F:
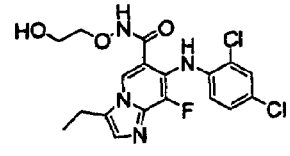
Figure 13F:
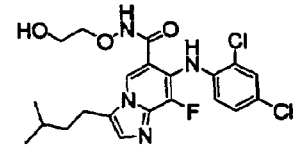
Figure 13G:
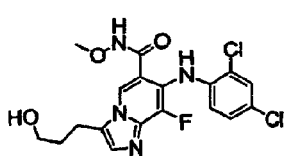
Figure 13G:
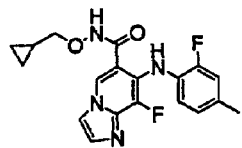
Figure 13G:
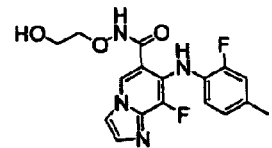
Figure 13G:
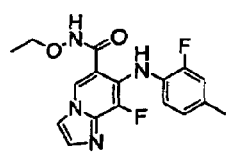
Figure 13G:
Figure 13G:
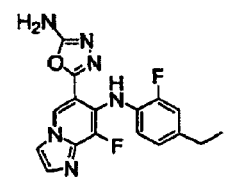
Figure 13G:
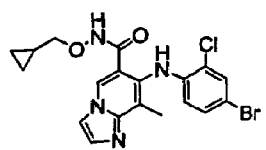
Figure 13G:
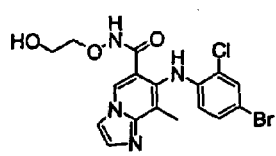
Figure 13G:
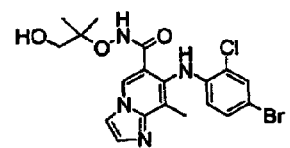
Figure 13G:
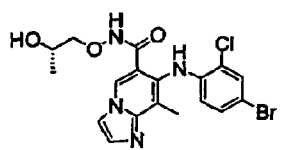
Figure 13G:
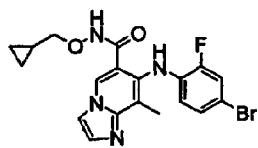
Figure 13G:
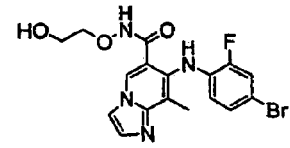
Figure 13G:
Figure 13G:
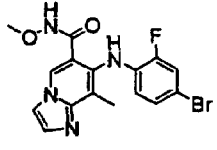
Figure 13G:
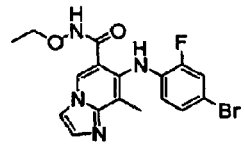
Figure 13G:
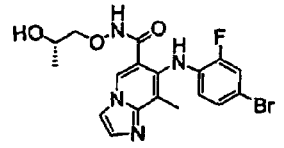
Figure 13G:
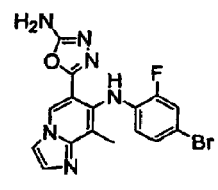
Figure 13G:
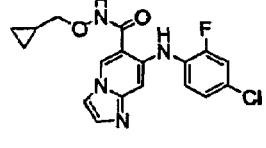
Figure 13G:
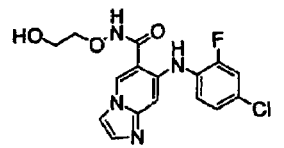

FIG. 12 shows the reaction scheme for the synthesis of Compounds 73a and 73b.

FIGS. 13A-13G show additional compounds suitable for use in the methods of the present invention.

DETAILED DESCRIPTION OF THE INVENTION

Disclosed herein are methods for treating an inflammatory disease or disorder in a mammal, such as a human, which method comprises administering a composition including a MEK inhibitor to a mammal in need of such treatment. In certain embodiments, the methods are used to treat arthritis. In other embodiments, the methods are used to treat inflammatory bowel disease.

As described in detail in the Examples, the effect of a MEK inhibitor of Formula II, AR-14, was investigated in three animal models of arthritis, namely collagen-induced arthritis (CIA), adjuvant induced arthritis (AIA) (Examples 1 and 2, respectively), and carrageenan paw edema (Example 4). Another MEK inhibitor of Formula II, AR-13, was also evaluated in the carrageenan paw edema animal model of inflammation (Example 4).

Oral administration of AR-14 resulted in significant inhibition of the progression of established arthritis (CIA and AIA models) in rats in a dose-dependent manner. In these models, reversal of acute gross and microscopic inflammation was observed with once daily oral doses of 10 and 30 mg/kg AR-14, respectively. The progression of established disease was stopped at 10 mg/kg, and improvement to normal was observed at 60 mg/kg in the CIA model and at 30 mg/kg in the AIA model. In addition, significant amelioration of disease (e.g., joint swelling and microscopic changes) was seen with once daily oral doses of 10 mg/kg AR-14, and significant inhibition of joint destruction was observed at a dose of 1 mg/kg in the CIA model. AR-14 was well tolerated at all doses administered and was found to be a selective inhibitor of MEK in vivo, and is useful as a therapeutic tool for arthritis.

In the carrageenan paw edema model, oral administration of AR-13 and AR-14 was observed to significantly inhibit paw weight, and both compounds were superior to the positive control indomethacin.

As described in detail in Example 3, a model of Crohn's disease (indomethacin-induced intestinal injury) was utilized to evaluate the effectiveness of AR-14 in treating inflammatory bowel disease (IBD). Oral administration of AR-14 resulted in significant inhibition of gross and microscopic gut inflammation in the indomethacin-induced inflammatory bowel disease model in rats, as measured by gut score, weight changes, and microscopic changes, with once daily oral doses of 10 mg/kg AR-14. AR-14 was well tolerated at all doses administered and was found to be a selective inhibitor of MEK in vivo, and is useful as a therapeutic tool for IBD.

Accordingly, one aspect of the invention features the use of MEK inhibitors in the treatment of inflammatory diseases and disorders. Examples of MEK inhibitors suitable for use in the methods of this invention include compounds of Formula I and solvates, metabolites, and pharmaceutically acceptable salts and prodrugs thereof

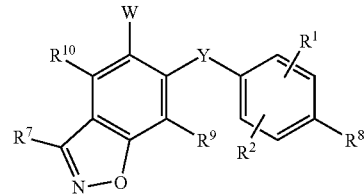

wherein:

$R^1$, $R^2$, $R^7$, $R^8$, $R^9$, and $R^{10}$ are independently hydrogen, halo, cyano, nitro, trifluoromethyl, difluoromethoxy, trifluoromethoxy, azido, —$OR^3$, —$C(O)R^3$, —$C(O)OR^3$, $NR^4C(O)OR^6$, —$OC(O)R^3$, —$NR^4SO_2R^6$, —$SO_2NR^3R^4$, —$NR^4C(O)R^3$, —$C(O)NR^3R^4$, —$NR^5C(O)NR^3R^4$, —$NR^5C(NCN)NR^3R^4$, —$NR^3R^4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —$S(O)_j$($C_1$-$C_6$ alkyl), —$S(O)_j(CR^4R^5)_m$-aryl, aryl, arylalkyl, heteroaryl, heteroarylalkyl, heterocyclyl, heterocyclylalkyl, —$O(CR^4R^5)_m$-aryl, —$NR^4(CR^4R^5)_m$-aryl, —$O(CR^4R^5)_m$-heteroaryl, —$NR^4(CR^4R^5)_m$-heteroaryl, —$O(CR^4R^5)_m$-heterocyclyl or —$NR^4(CR^4R^5)_m$-heterocyclyl, wherein said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halo, cyano, nitro, trifluoromethyl, difluoromethoxy, trifluoromethoxy, azido, —$NR^4SO_2R^6$, —$SO_2NR^3R^4$, —$C(O)R^3$, —$C(O)OR^3$, —$OC(O)R^3$, —$NR^4C(O)OR^6$, —$NR^4C(O)R^3$, —$C(O)NR^3R^4$, —$NR^3R^4$, —$NR^5C(O)NR^3R^4$, —$NR^5C(NCN)NR^3R^4$, —$OR^3$, aryl, heteroaryl, arylalkyl, heteroarylalkyl, heterocyclyl and heterocyclylalkyl;

$R^3$ is hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, phosphate, or an amino acid residue, wherein said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halo, cyano, nitro, trifluoromethyl, difluoromethoxy, trifluoromethoxy, azido, —NR'SO$_2$R'''', —SO$_2$NR'R''', —C(O)R', C(O)OR', —OC(O)R', —NR'C(O)OR'''', —NR'C(O)R'', —C(O)NR'R'', —SR', —S(O)R'''', —SO$_2$R'''', —NR'R'', —NR'C(O)NR''R''', —NR'C(NCN)NR''R''', —OR', aryl, heteroaryl, arylalkyl, heteroarylalkyl, heterocyclyl and heterocyclylalkyl, or $R^3$ and $R^4$ together with the atom to which they are attached form a 4 to 10 membered carbocyclic, heteroaryl or heterocyclic ring, wherein said carbocyclic, heteroaryl or heterocyclic rings are optionally substituted with one or more groups independently selected from halo, cyano, nitro, trifluoromethyl, difluoromethoxy, trifluoromethoxy, azido, —NR'SO$_2$R'''', —SO$_2$NR'R''', —C(O)R', —C(O)OR', —OC(O)R', —NR'C(O)OR'''', —NR'C(O)R'', —C(O)NR'R'', —SO$_2$R'''', —NR'R'', —NR'C(O)NR''R''', —NR'C(NCN)NR''R''', —OR', aryl, heteroaryl, arylalkyl, heteroarylalkyl, heterocyclyl and heterocyclylalkyl;

R', R'' and R''' are independently hydrogen, lower alkyl, lower alkenyl, aryl or arylalkyl, and R'''' is lower alkyl, lower alkenyl, aryl or arylalkyl, or any two of R', R'', R''' and R'''' together with the atoms to which they are attached form a 4 to 10 membered carbocyclic, heteroaryl or heterocyclic ring, wherein said alkyl, alkenyl, aryl, arylalkyl carbocyclic rings, heteroaryl rings or heterocyclic rings are optionally substituted with one or more groups independently selected from halo, cyano, nitro, trifluoromethyl, difluoromethoxy, trifluoromethoxy, azido, aryl, heteroaryl, arylalkyl, heteroarylalkyl, heterocyclyl, and heterocyclylalkyl;

$R^4$ and $R^5$ are independently hydrogen or $C_1$-$C_6$ alkyl, or $R^4$ and $R^5$ together with the atom to which they are attached form a 4 to 10 membered carbocyclic, heteroaryl or heterocyclic ring, wherein said alkyl or said carbocyclic, heteroaryl and heterocyclic rings are optionally substituted with one or more groups independently selected from halo, cyano, nitro, trifluoromethyl, difluoromethoxy, trifluoromethoxy, azido, —NR'SO$_2$R'''', —SO$_2$NR'R'', —C(O)R'''', —C(O)OR', —OC(O)R', —NR'C(O)OR'''', —NR'C(O)R'', —C(O)NR'R'', —SO$_2$R'''', —NR'R'', —NR'C(O)NR''R''', —NR'C(NCN)NR''R''', —OR', aryl, heteroaryl, arylalkyl, heteroarylalkyl, heterocyclyl and heterocyclylalkyl;

$R^6$ is trifluoromethyl, $C_1$-$C_{10}$ alkyl, $C_3$-$C_{10}$ cycloalkyl, aryl, arylalkyl, heteroaryl, heteroarylalkyl, heterocyclyl or heterocyclylalkyl, wherein said alkyl, cycloalkyl, aryl, arylalkyl, heteroaryl, heteroarylalkyl, heterocyclyl and heterocyclylalkyl portions are optionally substituted with one or more groups independently selected from oxo, halo, cyano, nitro, trifluoromethyl, difluoromethoxy, trifluoromethoxy, azido, —NR'SO$_2$R'''', —SO$_2$NR'R'', —C(O)R', —C(O)OR', —OC(O)R', —NR'C(O)OR'''', —NR'C(O)R'', —C(O)NR'R'', —SO$_2$R'''', —NR'R'', —NR'C(O)NR''R''', —NR'C(NCN)NR''R''', —OR', aryl, heteroaryl, arylalkyl, heteroarylalkyl, heterocyclyl and heterocyclylalkyl;

W is heteroaryl, heterocyclyl, —C(O)OR$^3$, —C(O)NR$^3$R$^4$, —C(O)NR$^4$OR$^3$, —C(O)R$^4$OR$^3$, —C(O)(C$_3$-C$_{10}$ cycloalkyl), —C(O)(C$_1$-C$_{10}$ alkyl), —C(O)(aryl), —C(O)(heteroaryl), —C(O)(heterocyclyl), —CONH(SO$_2$)CH$_3$ or CR$^3$OR$^3$, wherein any of said heteroaryl, heterocyclyl, —C(O)OR$^3$, —C(O)NR$^3$R$^4$, —C(O)NR$^4$OR$^3$, —C(O)R$^4$OR$^3$, —C(O)(C$_3$-C$_{10}$ cycloalkyl), —C(O)(C$_1$-C$_{10}$ alkyl), —C(O)(aryl), —C(O)(heteroaryl), —C(O)(heterocyclyl), —CONH(SO$_2$)CH$_3$ and CR$^3$OR$^3$ are optionally substituted with one or more groups independently selected from —NR$^3$R$^4$, —OR$^3$, —R$^2$, $C_1$-$C_{10}$ alkyl, $C_2$-$C_{10}$ alkenyl and $C_2$-$C_{10}$ alkynyl, wherein any of said $C_1$-$C_{10}$ alkyl, $C_2$-$C_{10}$ alkenyl, and $C_2$-$C_{10}$ alkynyl are optionally substituted with 1 or more groups independently selected from —NR$^3$R$^4$ and —OR$^3$;

m is 0, 1, 2, 3, 4 or 5;

j is 0, 1 or 2; and

Y is a linker.

A "linker" is a molecular entity that connects two or more molecular entities through covalent or non-covalent interactions. Examples of linkers include, but are not limited to, NR$^3$, O, S, S(O), S(O)$_2$, C(O), and CH$_2$, where R$^3$ is as defined above. In certain embodiments, the method utilizes a compound of Formula I wherein Y is NR$^3$. In particular embodiments, Y is NH. In certain embodiments, W is —C(O)OR$^3$, —C(O)NR$^4$OR$^3$, or —CONH(SO$_2$)CH$_3$.

Additional examples of MEK inhibitors suitable for use in the methods of the present invention include compounds of Formula II solvates, metabolites, and pharmaceutically acceptable salts and prodrugs thereof

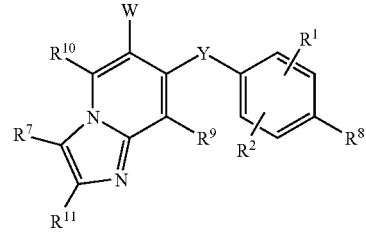

II wherein $R^1$, $R^2$, $R^7$, $R^8$, $R^9$, $R^{10}$, $R^{11}$, W and Y are as defined above, and $R^{11}$ is hydrogen, halo, cyano, nitro, trifluoromethyl, difluoromethoxy, trifluoromethoxy, azido, —OR$^3$, —C(O)R$^3$, —C(O)OR$^3$, NR$^4$C(O)OR$^6$, —OC(O)R$^3$, —NR$^4$SO$_2$R$^6$, —SO$_2$NR$^3$R$^{44}$—NR$^4$C(O)R$^3$, —C(O)NR$^3$R$^4$, —NR$^5$C(O)NR$^3$R$^4$, —NR$^5$C(CN)NR$^3$R$^4$, —NR$^3$R$^4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —S(O)$_j$(C$_1$-C$_6$ alkyl), —S(O)$_j$(CR$^4$R$^5$)$_m$-aryl, aryl, arylalkyl, heteroaryl, heteroarylalkyl, heterocyclyl, heterocyclylalkyl, —O(CR$^4$R$^5$)$_m$-aryl, —NR$^4$(CR$^4$R$^5$)$_m$-aryl, —O(CR$^4$R$^5$)$_m$-heteroaryl, —NR$^4$(CR$^4$R$^5$)$_m$-heteroaryl, —O(CR$^4$R$^5$)$_m$-heterocyclyl or —NR$^4$(CR$^4$R$^5$)$_m$-heterocyclyl, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halo, cyano, nitro, trifluoromethyl, difluoromethoxy, trifluoromethoxy, azido, —NR$^4$SO$_2$R$^6$, —SO$_2$NR$^3$R$^4$, —C(O)R$^3$, —C(O)OR$^3$, —OC(O)R$^3$, —NR$^4$C(O)OR$^6$, —NR$^4$C(O)R$^3$, —C(O)NR$^3$R$^4$, —NR$^3$R$^4$, —NR$^5$C(O)NR$^3$R$^4$, —NR$^5$C(NCN)NR$^3$R$^4$, —OR$^3$, aryl, heteroaryl, arylalkyl, heteroarylalkyl, heterocyclyl and heterocyclylalkyl. In certain embodiments, the method utilizes a compound of Formula II wherein Y is NR$^3$. In particular embodiments, Y is NH. In certain embodiments, W is —C(O)OR$^3$, —C(O)NR$^4$OR$^3$, or —CONH(SO$_2$)CH$_3$.

Additional examples of MEK inhibitors suitable for use in the methods of the present invention include compounds of Formula III and solvates, metabolites, and pharmaceutically acceptable salts and prodrugs thereof

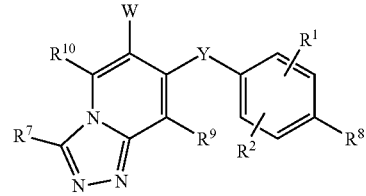

III wherein $R^1$, $R^2$, $R^7$, $R^8$, $R^9$, $R^{10}$, W and Y are as defined above. In certain embodiments, the method utilizes a compound of Formula III wherein Y is NR$^3$. In particular embodiments, Y is NH. In certain embodiments, W is —C(O)OR$^3$, —C(O)NR$^4$OR$^3$, or —CONH(SO$_2$)CH$_3$.

Additional examples of MEK inhibitors suitable for use in the methods of the present invention include compounds of Formula IV and solvates, metabolites, and pharmaceutically acceptable salts and prodrugs thereof

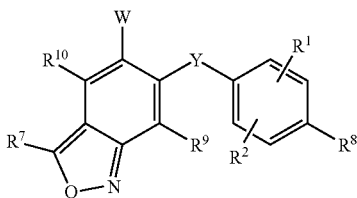

wherein $R^1$, $R^2$, $R^7$, $R^8$, $R^9$, $R^{10}$, W and Y are as defined above. In certain embodiments, the method utilizes a compound of Formula IV wherein Y is $NR^3$. In particular embodiments, Y is NH. In certain embodiments, W is $—C(O)OR^3$, $—C(O)NR^4OR^3$, or $—CONH(SO_2)CH_3$.

Additional examples of MEK inhibitors suitable for use in the methods of the present invention include compounds of Formula V and solvates, metabolites, and pharmaceutically acceptable salts and prodrugs thereof

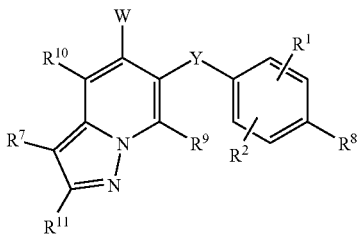

wherein $R^1$, $R^2$, $R^7$, $R^8$, $R^9$, $R^{10}$, $R^{11}$, W and Y are as defined above. In certain embodiments, the method utilizes a compound of Formula V wherein Y is $NR^3$. In particular embodiments, Y is NH. In certain embodiments, W is $—C(O)OR^3$, $—C(O)NR^4OR^3$, or $—CONH(SO_2)CH_3$.

The terms "alkyl" and "lower alkyl" as used herein refer to a saturated linear or branched-chain monovalent hydrocarbon radical having one to ten carbon atoms, wherein the alkyl radical may be optionally substituted independently with one or more substituents described below. Examples of alkyl groups include, but are not limited to, methyl, ethyl, n-propyl, isopropyl, butyl, isobutyl, sec-butyl, tert-butyl, pentyl, isopentyl, neopentyl, tert-pentyl, hexyl, 2-hexyl, 3-hexyl, 3-methylpentyl, heptyl, octyl, and the like.

The terms "alkenyl", "lower alkenyl" and "alkenyl" refer to linear or branched-chain monovalent hydrocarbon radical having two to 10 carbon atoms and at least one double bond, and include, but is not limited to, ethenyl, propenyl, 1-but-3-enyl, 1-pent-3-enyl, 1-hex-5-enyl and the like, wherein the alkenyl radical may be optionally substituted independently with one or more substituents described herein, and includes radicals having "cis" and "trans" orientations, or alternatively, "E" and "Z" orientations.

The terms "lower alkynyl" and "alkynyl" refer to a linear or branched monovalent hydrocarbon radical of two to twelve carbon atoms containing at least one triple bond. Examples include, but are not limited to, ethynyl, propynyl, butynyl, pentyn-2-yl and the like, wherein the alkynyl radical may be optionally substituted independently with one or more substituents described herein.

The term "allyl" refers to a radical having the formula $RC=CHCHR$, wherein R is alkyl, alkenyl, alkynyl, cycloalkyl, heterocycloalkyl, aryl, heteroaryl, or any substituent as defined herein, wherein the allyl may be optionally substituted independently with one or more substituents described herein.

The terms "carbocycle," "carbocyclyl," and "cycloalkyl" refer to saturated or partially unsaturated cyclic hydrocarbon radical having from three to ten carbon atoms. The term "cycloalkyl" includes monocyclic and polycyclic (e.g., bicyclic and tricyclic) cycloalkyl structures, wherein the polycyclic structures optionally include a saturated or partially unsaturated cycloalkyl fused to a saturated or partially unsaturated cycloalkyl or heterocycloalkyl ring or an aryl or heteroaryl ring. Examples of cycloalkyl groups include, but are not limited to, cyclopropyl, cyclobutyl, cyclopentyl, cyclohexyl, cycloheptyl, and the like. The cycloalkyl may be optionally substituted independently in one or more substitutable positions with various groups. For example, such cycloalkyl groups may be optionally substituted with, for example, $C_1$-$C_6$ alkyl, $C_1$-$C_6$ alkoxy, halo, hydroxy, cyano, nitro, amino, mono($C_1$-$C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl.

The term "heteroalkyl" refers to saturated linear or branched-chain monovalent hydrocarbon radical of one to twelve carbon atoms, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkyl radical may be optionally substituted independently with one or more substituents described herein. The term "heteroalkyl" encompasses alkoxy and heteroalkoxy radicals.

The terms "heterocycloalkyl," "heterocycle" or "hetercyclyl" refer to a saturated or partially unsaturated carbocyclic radical of 3 to 8 ring atoms in which at least one ring atom is a heteroatom selected from nitrogen, oxygen and sulfur, the remaining ring atoms being C, wherein one or more ring atoms may be optionally substituted independently with one or more substituent described below. The radical may be a carbon radical or heteroatom radical. The term further includes fused ring systems which include a heterocycle fused to an aromatic group. "Heterocycloalkyl" also includes radicals where heterocycle radicals are fused with aromatic or heteroaromatic rings. Examples of heterocycloalkyl rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl and quinolizinyl. Spiro moieties are also included within the scope of this definition. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). An example of a heterocyclic group wherein 2 ring carbon atoms are substituted with oxo (=O) moieties is 1,1-dioxo-thiomorpholinyl. The heterocycle groups herein are unsubstituted or, as specified, substituted in one or more substitutable positions with various groups. For example, such heterocycle groups may be optionally substituted with, for example, $C_1$-$C_6$ alkyl, $C_1$-$C_6$ alkoxy, halo, hydroxy, cyano, nitro, amino, mono($C_1$-$C_6$) alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$) alkyl, mono($C_1$-$C_6$)alkylamino($C_1$-$C_6$)alkyl or di($C_1$-$C_6$) alkylamino($C_1$-$C_6$)alkyl.

The term "aryl" refers to a monovalent aromatic carbocyclic radical having a single ring (e.g., phenyl), multiple rings (e.g., biphenyl), or multiple condensed rings in which at least one is aromatic, (e.g., 1,2,3,4-tetrahydronaphthyl, naphthyl), which is optionally mono-, di-, or trisubstituted with, e.g., halo, lower alkyl, lower alkoxy, trifluoromethyl, aryl, heteroaryl, and hydroxy.

The term "heteroaryl" refers to a monovalent aromatic radical of 5-, 6-, or 7-membered rings which includes fused ring systems (at least one of which is aromatic) of 5-10 atoms containing at least one and up to four heteroatoms selected from nitrogen, oxygen, or sulfur. Examples of heteroaryl groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and benzopyridinyl. Spiro moieties are also included within the scope of this definition. Heteroaryl groups are optionally mono-, di-, or trisubstituted with, e.g., halo, lower alkyl, lower alkoxy, haloalkyl, aryl, heteroaryl, and hydroxy.

The term "halo" includes fluoro, bromo, chloro, and iodo substituents.

The term "arylalkyl" means an alkyl moiety (as defined above) substituted with one or more aryl moiety (also as defined above). Examples of arylalkyl radicals are aryl-$C_{1-3}$-alkyls including, but not limited to, benzyl, phenylethyl, and the like.

The term "heteroarylalkyl" means an alkyl moiety (as defined above) substituted with a heteroaryl moiety (also as defined above). Examples include 5- or 6-membered heteroaryl-$C_{1-3}$-alkyls such as, but not limited to, oxazolylmethyl, pyridylethyl and the like.

The term "heterocyclylalkyl" means an alkyl moiety (as defined above) substituted with a heterocyclyl moiety (also defined above). Examples include 5- or 6-membered heterocyclyl-$C_{1-3}$-alkyls such as, but not limited to, tetrahydropyranylmethyl.

The term "cycloalkylalkyl" means an alkyl moiety (as defined above) substituted with a cycloalkyl moiety (also defined above). Examples include 5- or 6membered cycloalkyl-$C_{1-3}$-alkyls such as cyclopropylmethyl.

The term "Me" means methyl, "Et" means ethyl, "Bu" means butyl and "Ac" means acetyl.

In general, the various moieties or functional groups of the compounds of Formulas I-V may be optionally substituted by one or more substituents. Examples of substituents suitable for purposes of this invention include, but are not limited to, oxo, halo, cyano, nitro, trifluoromethyl, difluoromethoxy, trifluoromethoxy, azido, —$NR^4SO_2R^6$, —$SO_2NR^3R^4$, —C(O) $R^3$, —C(O)O$R^3$, —OC(O)$R^3$, —$NR^4C(O)OR^6$, —$NR^4C(O)$ $R^3$, —C(O)$NR^3R^4$, —$NR^3R^4$, —$NR^5C(O)NR^3R^4$, —$NR^5C$ (NCN)$NR^3R^4$, —O$R^3$, aryl, heteroaryl, arylalkyl, heteroarylalkyl, heterocyclyl, and heterocyclylalkyl, wherein $R^3$, $R^4$, $R^5$ and $R^6$ are as defined herein.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

In the above compounds, where a term such as $(CR^4R^5)_m$ is used, $R^4$ and $R^5$ may vary with each iteration of m above 1. For instance, where m is 2, the term $(CR^4R^5)_m$ may equal —$CH_2CH_2$— or —$CH(CH_3)C(CH_2CH_3)(CH_2CH_2CH_3)$— or any number of similar moieties falling within the scope of the definitions of $R^4$ and $R^5$.

The compounds of Formulas I-V may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers, diastereomers mixtures, racemic or otherwise, thereof. Accordingly, this invention also includes the use of such isomers, including diastereomeric mixtures and pure enantiomers of the compounds of Formulas I-V, in the treatment of inflammatory disorders and diseases.

This invention also encompasses the use of pharmaceutically acceptable prodrugs of compounds of Formulas I-V in the treatment of inflammatory disorders. A "pharmaceutically acceptable prodrug" is a compound that may be converted under physiological conditions or by solvolysis to the specified compound or to a pharmaceutically acceptable salt of such compound. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of Formulas I-V. The amino acid residues include but are not limited to the 20 naturally occurring amino acids commonly designated by three letter symbols and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. One embodiment of a prodrug suitable for use in the methods of the present invention is a compound of Formula I-V covalently joined to a phosphate residue. Another example of a suitable prodrug is a compound of Formula I-V covalently joined to a valine residue.

Additional types of prodrugs are also encompassed. For instance, free carboxyl groups can be derivatized as amides or alkyl esters. Free hydroxy groups may be derivatized using groups including but not limited to phosphate esters, hemisuccinates, dimethylaminoacetates, and phosphoryloxymethyloxycarbonyls, as outlined in *Advanced Drug Delivery Reviews*, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or wherein the acyl group is an amino acid ester as described above, are also encompassed. Prodrugs of this type are described in *J. Med. Chem.*, 1996, 39, 10. Free amines can also be derivatized as amides, sulfonamides or phosphonamides. All of these prodrug moieties may incorporate groups including but not limited to ether, amine and carboxylic acid functionalities.

In addition, the invention also includes the use of solvates, pharmaceutically active metabolites, and pharmaceutically acceptable salts of compounds of Formulas I-V.

The term "solvate" refers to an aggregate of a compound of Formula I-V with one or more solvent molecules.

A "metabolite" is a pharmacologically active product produced through in vivo metabolism in the body of a compound of Formula I-V or a salt thereof. Such products may result for example from the oxidation, reduction, hydrolysis, amidation, deamidation, esterification, deesterification, enzymatic cleavage, and the like, of the administered compound. Metabolites are typically identified by preparing a radiolabelled (e.g., $^{14}$C or $^{3}$H) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to about 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolites, so long as they are not otherwise found in vivo, are useful in diagnostic assays for therapeutic dosing of the compounds of the invention.

A "pharmaceutically acceptable salt" as used herein, unless otherwise indicated, includes salts that retain the biological effectiveness of the free acids and bases of the specified compound and that are not biologically or otherwise undesirable. A compound of Formula I-V may possess a sufficiently acidic, a sufficiently basic, or both functional groups, and accordingly react with any of a number of inorganic or organic bases, and inorganic and organic acids, to form a pharmaceutically acceptable salt. Examples of pharmaceutically acceptable salts include those salts prepared by reaction of the compounds of the present invention with a mineral or organic acid or an inorganic base, such salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates. Since a single compound of the present invention may include more than one acidic or basic moiety, the compounds of the present invention may include mono, di or tri-salts in a single compound.

If the compound of Formula I-V is a base, the desired pharmaceutically acceptable salt may be prepared by any suitable method available in the art, for example, treatment of the free base with an acidic compound, particularly an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of Formula I-V is an acid, the desired pharmaceutically acceptable salt may be prepared by any suitable method, for example, treatment of the free acid with an inorganic or organic base. In certain embodiments, inorganic salts are those formed with alkali and alkaline earth metals such as lithium, sodium, potassium, barium and calcium. Examples of organic base salts include, for example, ammonium, dibenzylammonium, benzylammonium, 2-hydroxyethylammonium, bis(2-hydroxyethyl)ammonium, phenylethylbenzylamine, dibenzylethylenediamine, and the like salts. Other salts of acidic moieties may include, for example, those salts formed with procaine, quinine and N-methylglusoamine, plus salts formed with basic amino acids such as glycine, ornithine, histidine, phenylglycine, lysine and arginine.

The compounds of Formula I-V may be prepared using the reaction routes and synthesis schemes 1-9 as described below, employing the techniques available in the art using starting materials that are readily available or can be synthesized using methods known in the art.

SCHEME 1

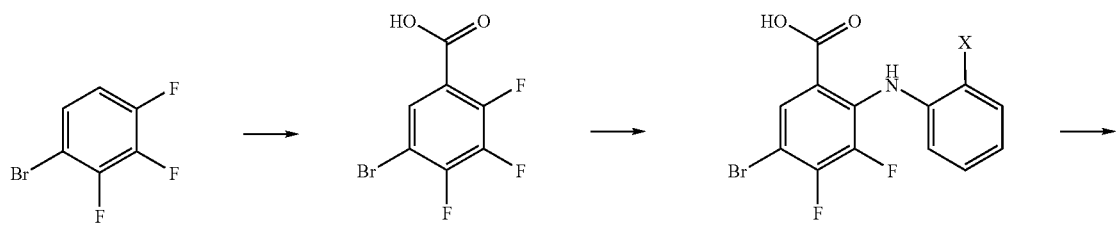

-continued
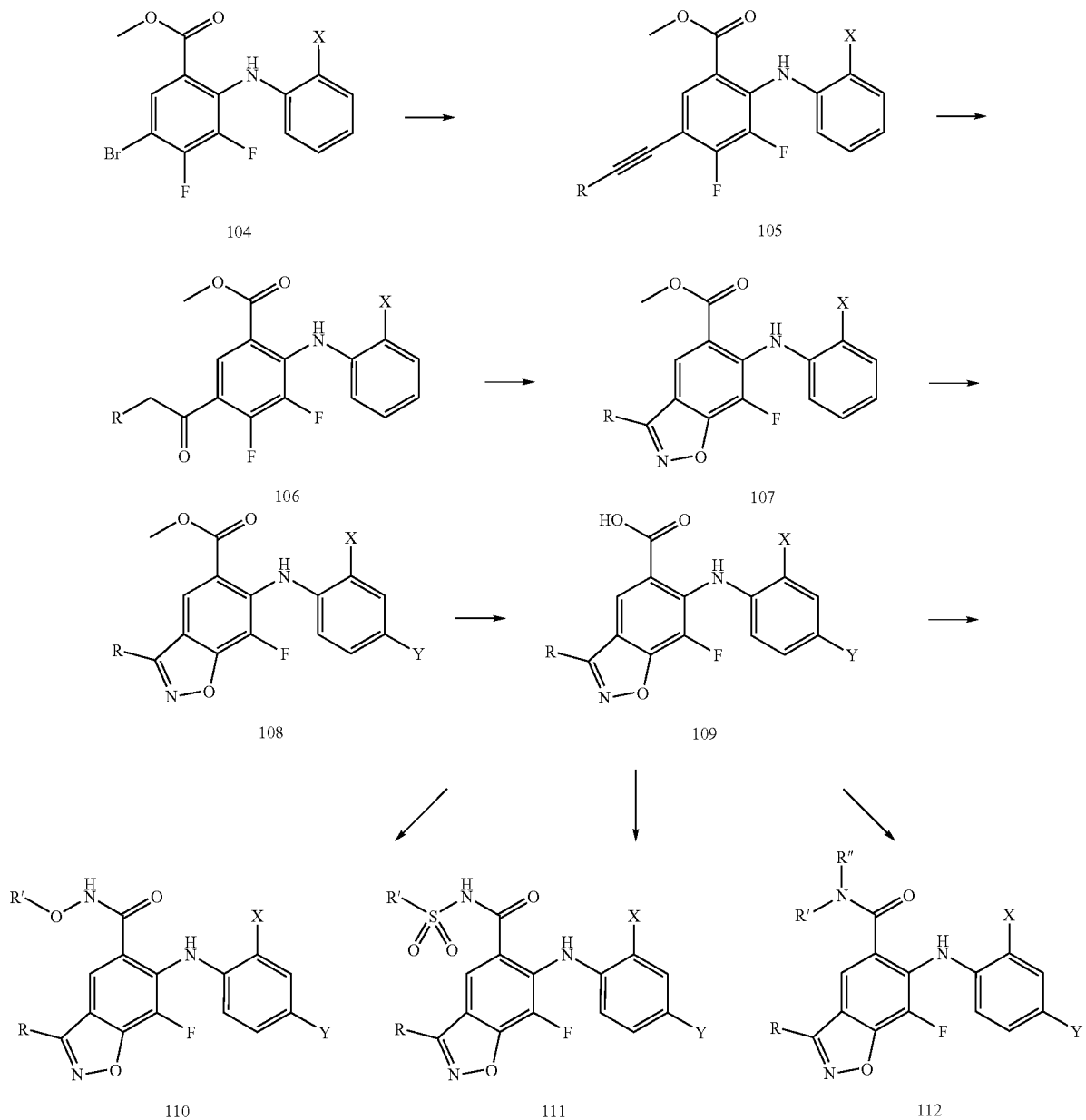
SCHEME 2
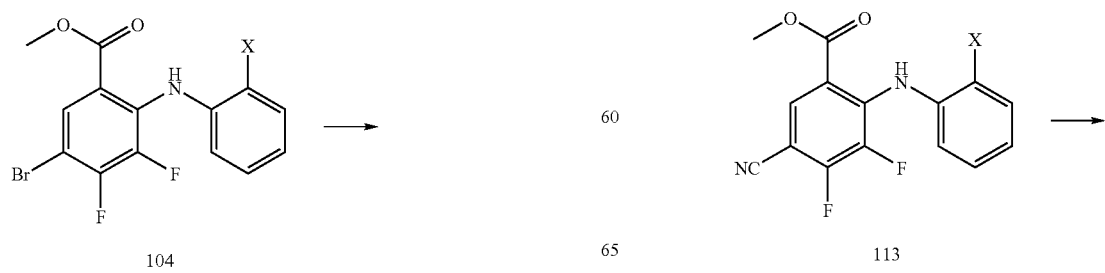
-continued

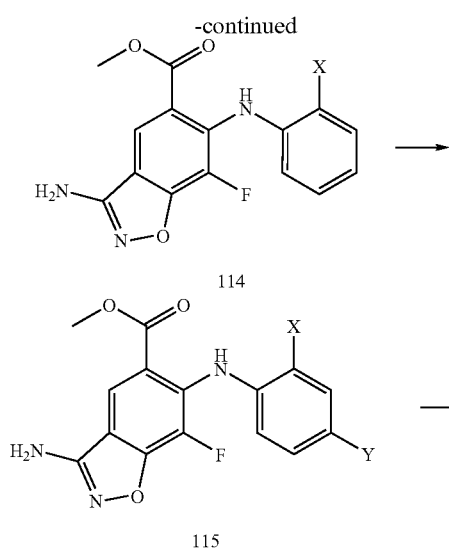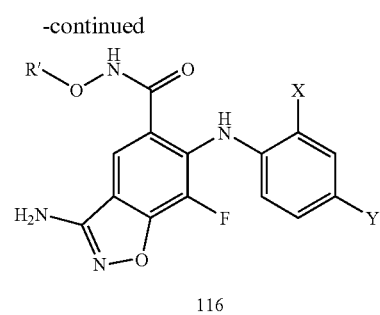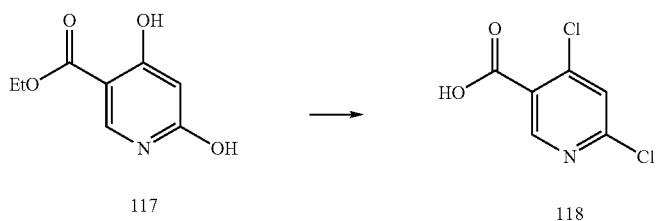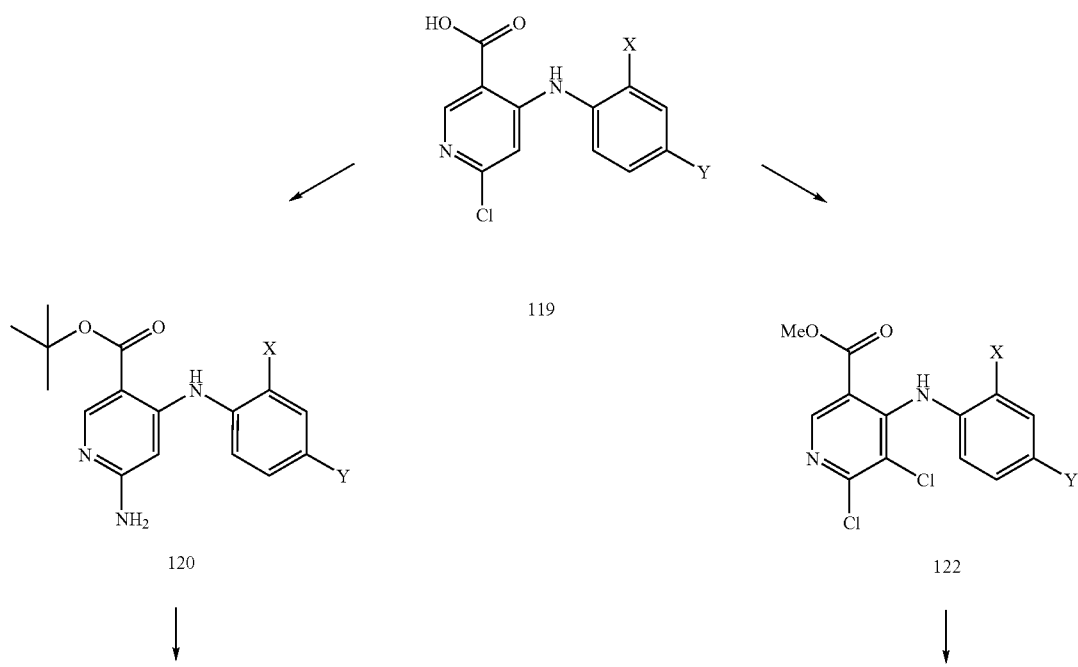

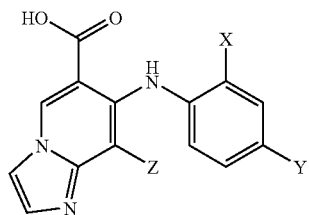
121
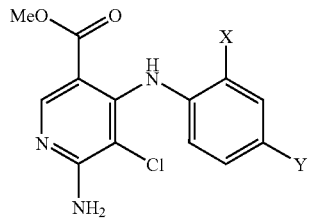
123
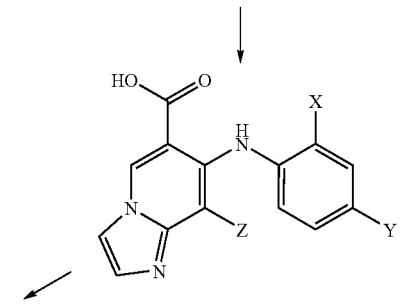
124
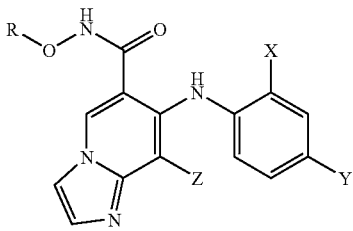
125
SCHEME 4
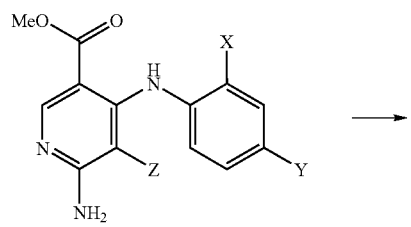
126
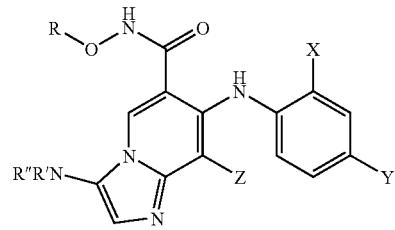
129
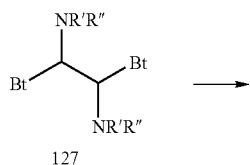
127
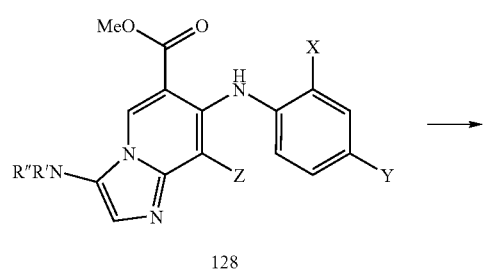
128
Bt = benzotriazole
SCHEME 5
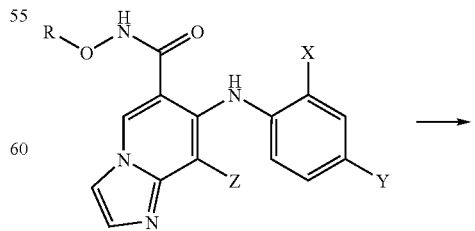
130

-continued
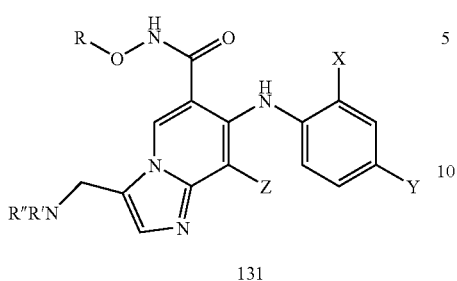
131
SCHEME 6
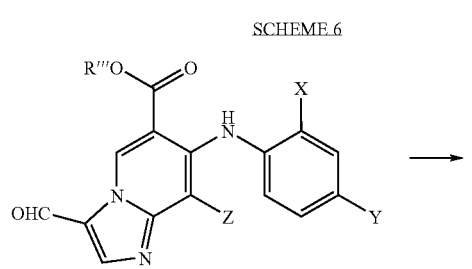
132
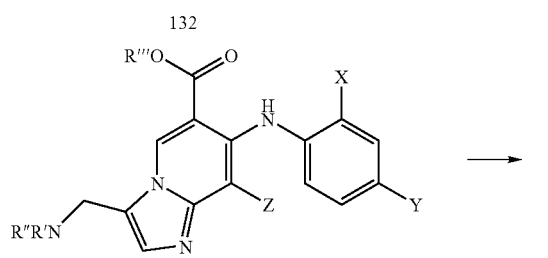
133
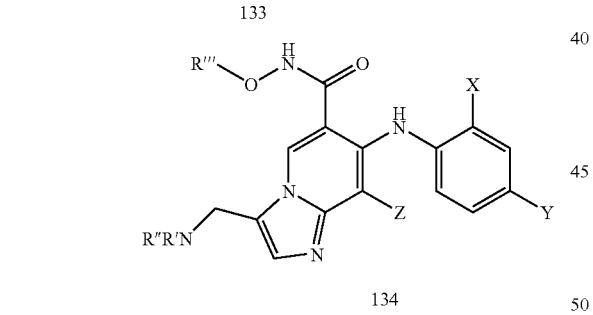
134
SCHEME 7
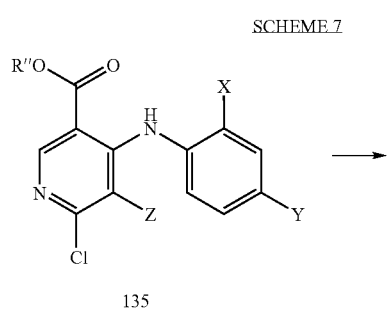
135
-continued
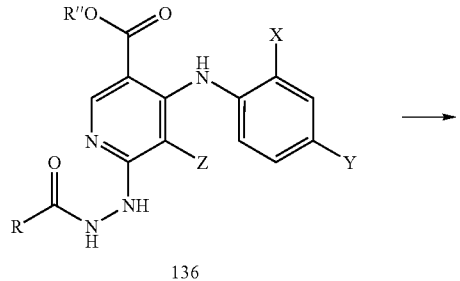
136
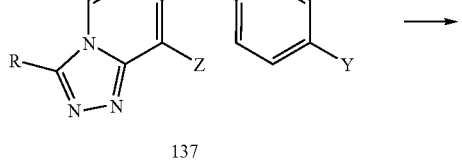
137
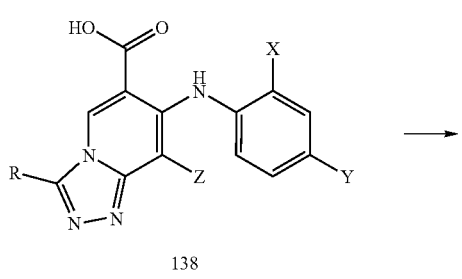
138
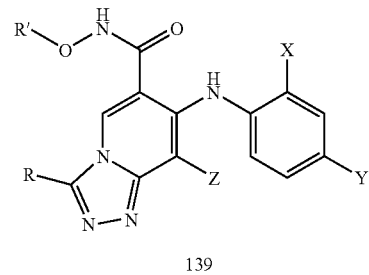
139
SCHEME 8
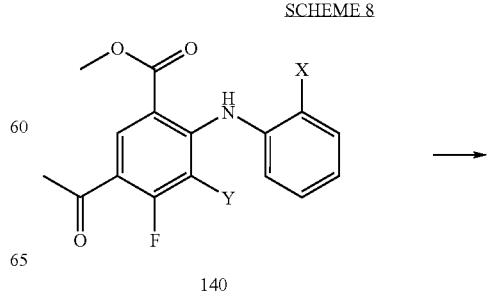
140

25
-continued
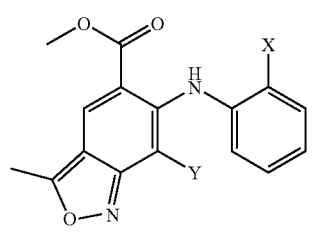
141
26
-continued
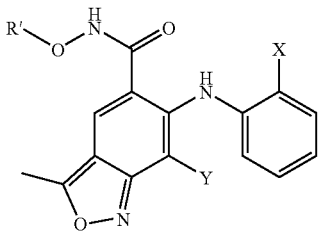
142
SCHEME 9
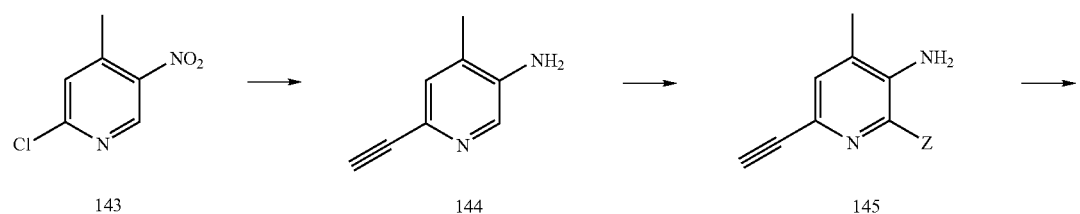
143  144  145
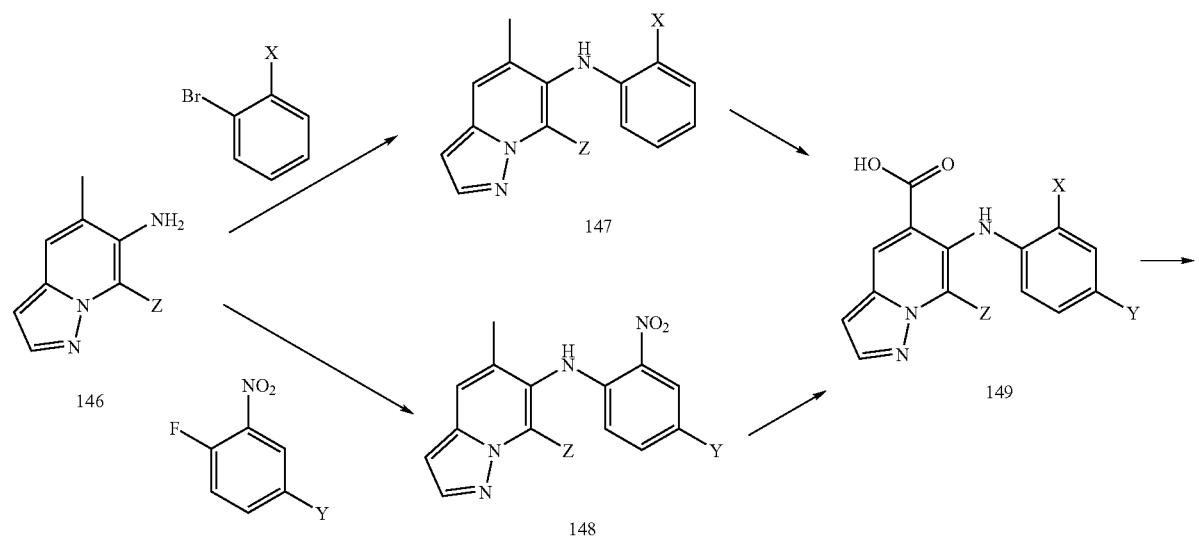
146  147  148  149
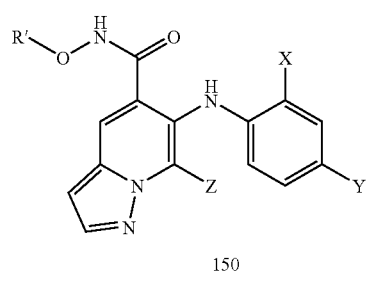
150

Scheme 1 illustrates a method of preparing compounds of the Formula I. Carboxylic acid 102 can be prepared from arene 101 by deprotonation at low temperature (−100 to −60° C.) in the appropriate ethereal solvent such as THF or diethyl ether followed by carbon dioxide quench, which can be performed with solid dry ice. The deprotonation can be accomplished with LDA in THF at −78° C. In one example, the quench method comprises adding the aryllithium THF solution via cannula to a saturated solution of dry carbon dioxide in THF at −78° C. and then warming to room temperature. Aniline 103 can be prepared by deprotonation of an appropriate 2-substituted aniline with KHMDS, LiHMDS, NaHMDS or LDA at low temperature (−100 to −60° C.) in an appropriate ethereal solvent such as THF or diethyl ether, followed by addition of carboxylic acid 102 and warming to room temperature. In one embodiment, deprotonation is accomplished with LDA at −78° C. in THF, followed by addition of carboxylic acid 102 and warming to room temperature. Ester 104 can be prepared by standard methods including, but not limited to, Fisher esterification (MeOH, $H_2SO_4$), reaction with $TMSCHN_2$ or TMSCl in MeOH. Acetylene derivative 105 is prepared by Sonagashria coupling of bromide 104 using an appropriately substituted acetylene, CuI, an amine base, palladium catalyst and organic solvent such as DME, THF, or DMF at temperatures between 25 and 100° C. Suitable palladium catalysts include, but are not limited to, $PdCl_2(dppf)$, $Pd(Ph_3P)_4$, and $Pd_2 dba_3/dppf$. Suitable amine bases include, but are not limited to, $Et_3N$, Hunig's base, and diisopropylamine. In one embodiment, the Pd(0) mediated coupling to prepare acetylene 105 is accomplished with $Pd(PPh_3)_2Cl_2$, CuI, diisopropylamine, and the appropriate substituted acetylene in THF at room temperature. Hydrolysis of acetylene 105 to prepare ketone 106 can be accomplished by standard methods including but not limited to $H_2SO_4$, TFA, trifluorosulfonamide, $FeCl_3$, or $HgSO_4/H_2SO_4$. Benzisoxazole 107 can be prepared in a two-step procedure from ketone 106. Addition of the potassium salt of acetone oxime in suitable organic solvent such as THF or $Et_2O$ at temperatures ranging from −78 to 5° C. is followed by acid catalyzed cyclization. The acetone oxime addition is most easily performed by addition of a THF solution of ketone 106 to the salt at 0° C. The cyclization can be accomplished using a variety of acidic aqueous conditions at a range of temperatures. In one embodiment cyclization is accomplished by treatment of the isopropylideneaminooxybenzoic acid methyl ester with 5% aqueous HCl in MeOH at reflux. Halogenation to form benzisoxazole 108 is accomplished using standard procedures such as NCS or NBS in DMF. Hydrolysis of ester 108 to form carboxylic acid 109 can be performed under standard conditions. The acid can be converted to hydroxamate 110 or amide 112 by standard coupling procedures including but not limited to EDCI/HOBt, PyBOP, or DIC and the appropriate hydroxylamine or amine. Alternatively, hydroxamate 110 or amide 112 can be prepared in two steps by initial conversion to the acid chloride by standard methods followed by addition of the hydroxylamine or amine. Acyl sulfonamide 111 can be synthesized by preparing an activated ester of carboxylic acid 109 followed by treatment with the appropriate sulfonamide and tertiary amine base in a suitable organic solvent such as THF. In one embodiment, acyl sulfonamide 111 is prepared by treatment of carboxylic acid 109 with CDI at elevated temperature (50° C.) in THF followed by treatment with the appropriate sulfonamide and DBU.

Scheme 2 illustrates an alternative method for synthesizing compounds of the Formula I. Nitrile 113 can be prepared by palladium mediated coupling of bromide 104 with zinc cyanide in suitable organic solvent such as DMA, NMP or DMF at elevated temperatures ranging from 50 to 120° C. Several palladium catalysts may be employed including but not limited to $Pd(PPh_3)_4$, $PdCl_2(dppf)$, or $Pd_2 dba_3$ with ligands such as dppe, dppp, dppf or BINAP. In one embodiment, nitrile 113 is prepared from bromide 104 by treatment with zinc cyanide, $Pd_2 dba_3$, and dppf in NMP at 120° C. Amino benzisoxazole 114 can be prepared in a two step procedure from nitrile 113 by the addition of the potassium salt of acetone oxime in suitable organic solvent such as THF or $Et_2O$ at temperatures ranging from −78 to 5° C. followed by acid catalyzed cyclization. In one embodiment the acetone oxime addition can be performed by addition of a THF solution of nitrile 113 to the salt at 0° C. in THF followed by warming to room temperature. The cyclization can be accomplished under a variety of acidic conditions at a range of temperatures. In one embodiment, the cyclization method comprises treatment of the oxime addition product in MeOH with 2M HCl in $Et_2O$. Halogenation to form benzisoxazole 115 is accomplished using standard procedures such as NCS or NBS in DMF. Compound 116 is prepared in a two step procedure comprising hydrolysis of ester 115 under standard conditions to form the corresponding carboxylic acid, followed by conversion of the carboxylic acid to hydroxamate 116 by standard coupling procedures, including but not limited, to EDCI/HOBt, PyBOP, or DIC and the appropriate hydroxylamine.

Scheme 3 illustrates a method of synthesizing compounds of the Formula II. 4,6-Dichloronicotinic acid 118 can be prepared from 4,6-dihydroxynicotinic acid ethyl ester 117 in two steps. In the first step, 4,6-dihydroxynicotinic acid ethyl ester 117 is chlorinated using an appropriate reagent such as $POCl_3$, oxalyl chloride or thionyl chloride. In one embodiment, chlorination is accomplished with $POCl_3$ and $Et_3N$ at elevated temperatures. Hydrolysis of the resulting dichloroethyl ester to provide compound 118 can be performed under standard conditions. Aniline 119 can be prepared by deprotonation of the properly substituted aniline with KHMDS, LiHMDS, NaHMDS or LDA at low temperature (−100 to −60° C.) in appropriate ethereal solvent such as THF or diethyl ether followed by addition of carboxylic acid 118 and warming to room temperature. In one embodiment, deprotonation is accomplished with LiHMDS at −78° C. in THF, followed by addition of carboxylic acid 118 and warming to room temperature. Aminopyridine 120 is prepared in three steps from aniline 119. In the first step, the tert-butyl ester is prepared by treating the acid 119 with 2-tert-butyl-1,3-diisopropylisourea in THF at temperatures ranging from 25 to 75° C. In the second step, sodium azide is added to the tert-butyl ester in DMF at 80° C. The aminopyridine 120 is prepared by reduction of the azide under standard conditions including but not limited to Zn dust/AcOH, Pt/C or $PtO_2$ in the presence of $H_2$ gas, $Ph_3P$ or $SnCl_2/MeOH$. In one embodiment, the azide reduction is accomplished by treatment with Zn dust in a mixture of methylene chloride and acetic acid. Imidazopyridine 121 wherein Z=F is prepared in two steps from aminopyridine 120. In the first step, fluorination is accomplished by treatment of the aminopyridine 120 with SELECTFLUOR® in a mixture of MeOH and water or pH 7 phosphate buffer. Cyclization to form imidazopyridine 121 (Z=H or F) can be accomplished by treatment with chloroacetaldehyde or bromoacetaldehyde in suitable organic solvent such as DMF or EtOH at elevated temperatures (50 to 120° C.). In one embodiment, cyclization is realized by treatment with chloroacetaldehyde in EtOH at 70° C. Alternatively, aniline 119 can be converted to dichloroester 122 in two steps. In the first step, chlorination is performed under standard conditions such as NCS in DMF. In the second step, esterification can be achieved by standard methods including but not limited to Fisher esterification (MeOH, $H_2SO_4$), reaction with $TMSCHN_2$ or TMSCI in MeOH. Aminopyridine 123 can be prepared as described above for aminopyridine 120 with the exception that the sodium azide addition can be accomplished at room temperature. Cyclization (achieved as described above for imidazopyridine 121) followed by standard basic saponification gives imidazopyridine 124. Hydroxamate 125 can be prepared from either imidazopyridine 121 or 124 using standard coupling procedures including but not limited to EDCI/HOBt, PyBOP, or DIC and the appropriate hydroxylamine. Alternatively, hydroxamate 125 can be prepared in two steps by initial conversion to the acid chloride by standard methods followed by addition of the hydroxylamine.

Scheme 4 illustrates an alternative method of preparing compounds of Formula II. An appropriately functionalized 2-aminopyridine 126 in a suitable organic solvent such as dichloromethane or dichloroethane is reacted with a Lewis acid such as zinc bromide and condensation product 127 as disclosed by Katritzky et al. (*J. Org. Chem.*, 2003, 68, 4935-4937: *J. Org. Chem.*, 1990, 55, 3209-3213) to provide the 3-dialkyamino-imidazo[1,2-a]pyridine ring system 128. Condensation products 127 (i.e., condensation of a glyoxal, benzotriazole and a secondary amine) can be generated using benzotriazole, glyoxal and any appropriate secondary amine including, but not limited to dimethylamine, diethylamine, pyrrolidine, piperidine, morpholine, 1-methylpiperazine, N-methylallylamine, diallyamine, and N-methylbenzylamine. The ester 128 is hydrolyzed by standard saponification methods, and the resulting acid can be converted to hydroxamate 129 by standard coupling procedures including but not limited to EDCI/HOBt, PyBOP, or DIC and the appropriate hydroxylamine. Alternatively, hydroxamate 129 can be prepared in two steps by initial conversion of the carboxylic acid to the acid chloride or activated ester by standard methods followed by addition of the hydroxylamine.

Scheme 5 illustrates an alternative method of preparing compounds of the Formula II. The preparation of 3-aminomethylimidazo[1,2-a]pyridines 131 using the modified Mannich reaction procedure developed by Kercher et al. (manuscript in preparation) is illustrated. The reaction is generally carried out by combining 37% aqueous formaldehyde and a suitable amine in 6:1 acetonitrile/water. Several secondary amines can be employed including but not limited to pyrrolidine, piperidine, morpholine, dimethylamine, N-BOC-piperazine and 1-methylpiperazine. The solution of amine and formaldehyde is stirred for approximately half an hour after which time scandium triflate and the appropriate imidazo[1,2-a]pyridine 130 are sequentially added. In one embodiment, the Mannich reaction is catalyzed by a Group IIIA lanthanide triflate, such as scandium triflate, though alternatively it may be performed using an excess of protic acid (AcOH or HCl) or elevated temperatures.

Scheme 6 illustrates an alternative method of preparing compounds of Formula II. In Scheme 6, the preparation of 3-aminomethylimidazo[1,2-a]pyridines 134 via reductive alkylation is illustrated. The 3-aminomethylimidazo[1,2-a]pyridine 133 is prepared from the appropriate 3-formylimidazo[1,2-a]pyridine 132 and a suitable amine using standard reduction methods such as $Na(CN)BH_3$, $Na(OAc)_3BH$, $NMe_4BH(OAc)_3$ with or without the addition of acetic acid in a suitable nonreactive organic solvent such as methylene chloride, acetonitrile or tetrahydrofuran. The reductive amination is generally accomplished by treatment of the aldehyde derivative 132 with the amine and acetic acid in tetrahydrofuran at room temperature followed by the addition of $Na(OAc)_3BH$. In cases wherein R"=H, the corresponding secondary amine 133 can optionally be protected, for example with an acid labile protecting group such as tert-butyl carbamate (BOC) to facilitate handling in subsequent steps. The ester is hydrolyzed by standard saponification methods, and the resulting acid can be converted to hydroxamate 134 by standard coupling procedures including but not limited to EDCI/HOBt, PyBOP, or DIC and the appropriate hydroxylamine. Alternatively, hydroxamate 134 can be prepared in two steps by initial conversion of the carboxylic acid to the acid chloride or activated ester by standard methods followed by addition of the hydroxylamine. Protecting groups, if present, are removed after coupling.

Scheme 7 illustrates a method of preparing compounds of Formula III. In Scheme 7 the preparation of 3-alkyl-[1,2,4]triazolo[4,3-a]pyridine derivatives is illustrated. Compound 136 is prepared from compound 135 in a two-step process. A suitably functionalized 2-chloropyridine derivative 135 is converted to the 2-hydrazinopyridine by reaction with hydrazine. The reaction is generally accomplished by reaction of hydrazine with the 2-chloropyridine derivative 135 in an unreactive organic solvent such as DMF or DMA at elevated temperature (50 to 100° C.). The 2-hydrazinopyridine is then acylated with the appropriate carboxylic acid halide such as fluoride, chloride or bromide, or the appropriate carboxylic acid anhydride or mixed anhydride in a suitable unreactive organic solvent such as dichloromethane, and in the presence of a suitable base such as triethylamine, diisopropylethylamine or pyridine, to provide intermediate 136. Acylation of the 2-hydrazinopyridine can alternatively be accomplished by standard peptide coupling procedures with the appropriate carboxylic acid and appropriate coupling reagent, including but not limited to EDCI/HOBt, PyBOP, or DIC. The intermediate 136 is converted to 3-alkyl-[1,2,4]triazolo[4,3-a]pyridine 137 by treatment with an excess of phosphorus oxychloride in refluxing dichloromethane. The ester 137 is hydrolyzed by standard saponification methods, and the resulting acid 138 can be converted to hydroxamate 139 by standard peptide coupling procedures including but not limited to EDCI/HOBt, PyBOP, or DIC and the appropriate hydroxylamine. Alternatively, hydroxamate 139 can be prepared in two steps by initial conversion of the carboxylic acid to the acid chloride or activated ester by standard methods followed by addition of the hydroxylamine.

Scheme 8 illustrates a method of preparing compounds of the Formula IV. In Scheme 8, the synthesis of 3-methyl-benzo[c]isoxazole derivatives is illustrated. Compound 141 is prepared from compound 140 in a two-step process. Methyl ester 140 is treated with sodium azide in 3:1 acetone/water at elevated temperature (reflux) to effect nucleophilic substitution. The 4-azido derivative is then isolated and heated in water at reflux to effect cyclization to the benzo[c]isoxazole ring system 141. The ester 141 is hydrolyzed by standard saponification methods, and the resulting carboxylic acid can be converted to hydroxamate 142 by standard peptide coupling procedures including but not limited to EDCI/HOBt, PyBOP, or DIC and the appropriate hydroxylamine. Alternatively, hydroxamate 142 can be prepared in two steps by initial conversion of the carboxylic acid to the acid chloride or activated ester by standard methods followed by addition of the hydroxylamine.

Scheme 9 illustrates a method of preparing compounds of Formula V. 2-Chloro-4-methyl-5-nitropyridine 143 can be converted to amino pyridine 144 in a three-step sequence. In the first step, Sonagashria coupling using TMS-acetylene, CuI, amine base, palladium catalyst and organic solvent such as DME, THF, or DMF at temperatures from 25 to 100° C. gives the nitroacetylenic pyridine. Suitable palladium catalysts include, but are not limited to, PdCl$_2$(dppf), Pd(Ph$_3$P)$_4$, Pd(PPh$_3$)$_2$Cl$_2$ and Pd$_2$ dba$_3$/dppf. Suitable amine bases include, but are not limited to, Et$_3$N, Hunig's base, and diisopropylamine. The amino pyridine 144 is then prepared by removal of the TMS group under standard conditions such as K$_2$CO$_3$ in MeOH, followed by reduction of the nitro group using either Zn dust/AcOH, Fe or SnCl$_2$/MeOH. For Z=H, aminopyridine 144 is used directly in the cyclization reaction. When Z=Cl, aminopyridine 144 is halogenated under standard conditions with NCS in DMF and then carried forward to the cyclization. When Z=F, the 2-chloro-3-aminopyridine intermediate is treated with KF, Kryptofix in DMSO to prepare amino pyridine 145. Cyclization to give pyrazolo[1,5-a]pyridine 146 is accomplished by treating aminopyridine 145 with O-(4-nitrophenyl)-hydroxylamine in a suitable organic solvent such as DMF at room temperature in presence of a base such as K$_2$CO$_3$. Carboxylic acid 149 can be prepared, for example, using one the following routes. One route involves palladium mediated cross-coupling with appropriately substituted bromobenzene and aminopyrazolo[1,5-a]pyridine 146. In this case, the cross-coupling can be accomplished with palladium catalyst and organic solvent such as DME, THF, dioxane, and toluene at temperatures from 60 to 120° C. Suitable palladium catalysts include, but are not limited to, Pd(OAc)$_2$, PdCl$_2$(dppf), Pd$_2$(bda)$_3$, and Pd(dba)$_2$. Suitable ligands include, but are not limited to, BINAP, DPPF, and (o-tol)$_3$P. Suitable amine bases include, but are not limited to, NaOt-Bu, KOt-Bu, and Cs$_2$CO$_3$. The second route involves S$_N$Ar reaction with aminopyrazolo[1,5-a]pyridine 146 and the appropriately substituted 2-fluoronitrobenzene. In this case, the coupling can be accomplished by mixing the two components in a suitable organic solvent such as xylenes, toluene, DMSO or DMF at elevated temperatures (80 to 150° C.). Optionally, a base can be employed in the S$_N$Ar coupling such as K$_2$CO$_3$ or Cs$_2$CO$_3$. The carboxylic acid 149 is then prepared by functionalization of the aromatic ring followed by oxidation. In the first case, functionalization involves halogenation under standard conditions with either NCS or NBS in DMF. In the second case, functionalization involves Sandmeyer chemistry to convert the nitroarene into the desired arene or arylhalide (nitro group reduction; diazonation; halogentation or protonation). In both routes, the last step to prepare carboxylic acid 149 is oxidation of the toluyl moiety. This can be achieved using standard methods including but not limited to KMnO$_4$, NaOCl/RuCl$_3$ or Na$_2$Cr$_2$O$_7$/HCl. The resulting carboxylic acid 149 can be converted to hydroxamate 150 by standard peptide coupling procedures including but not limited to EDCIIHOBt, PyBOP, or DIC and the appropriate hydroxylamine. Alternatively, hydroxamate 150 can be prepared in two steps by initial conversion of the carboxylic acid to the acid chloride or activated ester by standard methods followed by addition of the hydroxylamine.

The present invention provides methods for treating chronic inflammatory diseases. The method comprises administering an effective amount of a compound of Formula I-V, or a pharmaceutically acceptable salt, prodrug, solvate or pharmaceutical composition thereof, to a mammal, such as a human, in need of such treatment.

As used herein, the term "inflammatory disease" and "inflammatory disorder" includes a disease or disorder characterized by, caused by, resulting from, or becoming affected by inflammation. Examples of inflammatory diseases or disorders include, but are not limited to, acute and chronic inflammation disorders such as rheumatoid arthritis, osteoarthritis, inflammatory bowel diseases (including, but not limited to, Crohn's disease and ulcerative colitis), chronic obstructive pulmonary disorder (COPD), psoriasis, multiple sclerosis, asthma, diseases and disorders related to diabetic complications, fibrotic organ failure in organs such as lung, liver, kidney, and inflammatory complications of the cardiovascular system such as acute coronary syndrome.

The compounds of Formulas I-V may also be used in the treatment of inflammatory diseases in combination with one or more additional agents such as non-steroidal anti-inflammatory agents (NSAIDs), such as ibuprofen or aspirin (which reduce swelling and alleviate pain); disease-modifying anti-rheumatic drugs (DMARDs) such as methotrexate; 5-aminosalicylates (sulfasalazine and the sulfa-free agents); corticosteroids; immunomodulators such as 6-mercaptoputine ("6-MP"), azathioprine ("AZA"), cyclosporines, and biological response modifiers such as REMICADE (infliximab) and ENBREL (etanercept); fibroblast growth factors; platelet derived growth factors; enzyme blockers such as ARAVA (leflunomide); and/or a cartilage protecting agent such as hyaluronic acid, glucosamine, chondroitin, etc.

The term "treating," as used herein, unless otherwise indicated, means reversing, alleviating, inhibiting the progress of, or preventing the disorder or condition to which such term applies, or one or more symptoms of such disorder or condition, and includes, but is not limited to, preventing the disease condition from occurring in a mammal, particularly when the mammal is found to be predisposed to having the disease condition but has not yet been diagnosed as having it; modulating and/or inhibiting the disease condition; and/or alleviating the disease condition. The term "treatment," as used herein, unless otherwise indicated, refers to the act of treating as "treating" is defined immediately above.

The amount of a given agent that will correspond to such an amount will vary depending upon factors such as the particular compound, disease condition and its severity, the identity (e.g., weight) of the mammal in need of treatment, but can nevertheless be routinely determined by one skilled in the art.

In order to use a compound of the Formula I-V or a solvate, metabolite, pharmaceutically acceptable salt or prodrug thereof, for the therapeutic treatment (including prophylactic treatment) of mammals including humans, it is normally formulated in accordance with standard pharmaceutical practice as a pharmaceutical composition. According to this aspect of the invention there is provided a pharmaceutical composition that comprises a compound of the Formula I-V, or a pharmaceutically acceptable salt or prodrug thereof, in association with a pharmaceutically acceptable diluent or carrier.

Accordingly, the invention also includes a method of treating a hyperproliferative disorder in a mammal, wherein the method comprises administering to said mammal a composition comprising an effective amount of one or more compounds of Formula I-V, or a solvate, metabolite, pharmaceutically acceptable salt or prodrug thereof, and a pharmaceutically acceptable carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, or intramuscular dosing or as a suppository for rectal dosing). For example, compositions intended for oral use may contain, for example, one or more coloring, sweetening, flavoring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 µm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulations, see Chapter 25.2 in Volume 5 of Comprehensive Medicinal Chemistry (Corwin Hansch; Chairman of Editorial Board), Pergamon Press 1990, which is specifically incorporated herein by reference.

The amount of a compound of this invention that is combined with one or more excipients to produce a single dosage form will necessarily vary depending upon the subject treated, the severity of the disorder or condition, the rate of administration, the disposition of the compound and the discretion of the prescribing physician. For example, an effective dosage may be in the range of about 1 to about 60 mg per kg body weight per day, in single or divided doses. In some instances, dosage levels below the lower limit of the aforesaid range may be more than adequate, while in other cases still larger doses may be employed without causing any harmful side effect, provided that such larger doses are first divided into several small doses for administration throughout the day. For further information on routes of administration and dosage regimes, see Chapter 25.3 in Volume 5 of Comprehensive Medicinal Chemistry (Corwin Hansch; Chairman of Editorial Board), Pergamon Press 1990, which is specifically incorporated herein by reference.

The size of the dose for therapeutic or prophylactic purposes of a compound of Formula I-V will naturally vary according to the nature and severity of the conditions, the age and sex of the animal or patient and the route of administration, according to well known principles of medicine.

The activity of the compounds of the present invention may be determined by the following procedure. N-terminal 6 His-tagged, constitutively active MEK-1 (2-393) is expressed in E. coli and protein is purified by conventional methods (Ahn, et al., Science 1994, 265, 966-970). The activity of MEK1 is assessed by measuring the incorporation of $\gamma$-$^{33}$P-phosphate from $\gamma$-$^{33}$P-ATP onto N-terminal His tagged ERK2, which is expressed in E. coli and is purified by conventional methods, in the presence of MEK-1. The assay is carried out in 96-well polypropylene plate. The incubation mixture (100 µL) comprises of 25 mM Hepes, pH 7.4, 10 mM $MgCl_2$, 5 mM O-glycerolphosphate, 100 µM Na-orthovanadate, 5 mM DTT, 5 nM MEK1, and 1 µM ERK2. Inhibitors are suspended in DMSO, and all reactions, including controls are performed at a final concentration of 1% DMSO. Reactions are initiated by the addition of 10 VtM ATP (with 0.5 µCi $\gamma$-$^{33}$P-ATP/well) and incubated at ambient temperature for 45 minutes. Equal volume of 25% TCA is added to stop the reaction and precipitate the proteins. Precipitated proteins are trapped onto glass fiber B filterplates, and excess labeled ATP washed off using a Tomtec MACH III harvester. Plates are allowed to air-dry prior to adding 30 µL/well of Packard Microscint 20, and plates are counted using a Packard TopCount. In this assay, compounds of the invention exhibited an $IC_{50}$ of less than 50 micromolar.

The examples presented below are intended to illustrate particular embodiments of the invention, and are not intended to limit the scope of the specification or the claims in any way.

CHEMICAL EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other MEK inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), N,N-dimethylformamide (DMF), dichloromethane, toluene, and dioxane were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Dyax Corporation) having a silica gel column or on a silica SepPak cartridge (Waters).

$^1$H-NMR spectra were recorded on a Varian instrument operating at 400 MHz. $^1$H-NMR spectra were obtained as $CDCl_3$, $CD_3OD$ or DMSO-$d_6$ solutions (reported in ppm), using chloroform as the reference standard (7.25 ppm). Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

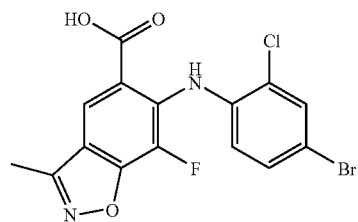

Synthesis of 6-(4-bromo-2-chlorophenylamino)-7-fluoro-3-methylbenzo[d]isoxazole-5-carboxylic acid (9a)

Step A: Preparation of 5-bromo-2,3,4-trifluorobenzoic acid (2): To a solution of 1-bromo-2,3,4-trifluorobenzene (1) (5.0 mL, 41.7 mmol) in THF (120 mL) was added LiHMDS (2.0 M solution, 21 mL, 42 mmol) at −78° C. After stirring for 1 hour at −78° C., the mixture was added to a solution of $CO_2$ in THF (1 L). The dry-ice bath was removed and the reaction mixture stirred overnight at room temperature. The reaction mixture was quenched with 10% aqueous HCl (835 mL), concentrated, and washed with ether (250 mL). The combined organics were washed with 5% aqueous NaOH (300 mL) and water (100 mL). The aqueous layer was acidified (pH 0) with concentrated HCl. The resulting suspension was extracted with ether (2×300 mL), dried over $MgSO_4$, filtered, concentrated under reduced pressure to afford 7.70 g (72% yield) of the desired product (2).

Step B: Preparation of 5-bromo-2-(2-chlorophenylamino)-3,4-difluorobenzoic acid (3): To a solution of LiHMDS (49.0 mL, 2 M in THF/heptane) in THF (40 mL) was added 2-chlorophenylamine (6.50 mL, 60.6 mmol) at −78° C. After vigorous stirring for 10 minutes, a solution of 5-bromo-2,3,4-trifluoro-benzoic acid (2) (7.70 g, 30.2 mmol) in THF (60 mL) was added. The dry-ice bath was removed and the reaction mixture stirred for 4 hours at room temperature. The mixture was concentrated, treated with 10% aqueous HCl (75 mL), and extracted with EtOAc. The combined organic extracts were dried over $MgSO_4$, filtered, and concentrated. Purification by trituration with boiling $CH_2Cl_2$ gave 7.24 g (66%) of the desired acid (3) as a yellow solid Step C: Preparation of 5-bromo-2-(2-chlorophenylamino)-3,4-difluorobenzoic acid methyl ester (4): To a solution of 5-bromo-2-(2-chlorophenylamino)-3,4-difluorobenzoic acid (3) (4.50 g, 12.4 mmol) in a 3:1 mixture of THF:MeOH (32 mL) was added trimethylsilyldiazomethane (8.10 ml of a 2 M solution in hexanes) at room temperature. After stirring for 2 hours, the reaction mixture was quenched with acetic acid, diluted with EtOAc, and washed with water. The organic layer was dried (MgSO$_4$) and concentrated under reduced pressure to give 4.35 g (93%) of the desired methyl ester (4).

Step D: Preparation of 2-(2-chlorophenylamino)-3,4-difluoro-5-trimethylsilanylethynylbenzoic acid methyl ester (5): A mixture of 5-bromo-2-(2-chlorophenylamino)-3,4-difluorobenzoic acid methyl ester (4) (101 mg, 0.268 mmol), TMS-acetylene (0.045 mL, 0.31 mmol), Pd(PPh$_3$)$_2$Cl$_2$ (18.7 mg, 0.0261 mmol), CuI (5.1 mg, 0.027 mmol), and i-Pr$_2$NH (0.075 mL, 0.53 mmol) in THF (1.5 mL) was stirred for 16 hours at room temperature. The reaction mixture was concentrated under reduced pressure, and diluted with EtOAc. The organic layer was washed with saturated aqueous NH$_4$Cl and brine, dried over MgSO$_4$, and concentrated. Purification by flash column chromatography using the Biotage system (100% hexane to 1% EtOAc in hexane) gave 81.3 mg (77% yield) of the desired product (5).

Step E: Preparation of 5-acetyl-2-(2-chlorophenylamino)-3,4-difluorobenzoic acid methyl ester (6): A mixture of 2-(2-chlorophenylamino)-3,4-difluoro-5-trimethylsilanylethynylbenzoic acid methyl ester (5) (79.4 mg, 0.20 mmol), HgSO$_4$ (59.8 mg, 2.0 mmol), and conc. H$_2$SO$_4$ (0.02 mL, 0.40 mmol) in 80% aqueous acetone (2.5 mL), were refluxed for 48 hours. The reaction was concentrated under reduced pressure, and diluted with EtOAc. The organic layer was washed with water and brine, dried over MgSO$_4$ and concentrated to give 50.1 mg (73%) of the desired product (6).

Step F: Preparation of 6-(2-chlorophenylamino)-7-fluoromethylbenzo[d]isoxazole-5-carboxylic acid methyl ester (7): t-BuOK (0.47 mL, 1.0 M in THF) was added to propan-2-one oxime (35 mg, 0.47 mmol). After stirring for 30 minutes, THF (0.5 mL) was added, and the reaction mixture was cooled to −78° C. A solution of 5-acetyl-2-(2-chlorophenylamino)-3,4-difluorobenzoic acid methyl ester (6) (50.0 mg, 0.147 mmol) in THF (1 mL) was added. The reaction mixture was slowly warmed to 0° C. and stirred for 2 hours. The reaction mixture was quenched with saturated aqueous NH$_4$Cl, diluted with EtOAc and water. The aqueous layer was separated and extracted with EtOAc. The combined organic extracts were dried over MgSO$_4$, filtered, and concentrated in vacuo to give 5-acetyl-2-(2-chlorophenylamino)-3-fluoro-4-isopropylideneaminooxybenzoic acid methyl ester. The recovered oxime was suspended in a 1:1 mixture of 5% aqueous HCl and MeOH (30 mL) and heated to reflux. After 1 hour, the reaction mixture was cooled to room temperature and diluted with EtOAc. The organic layer was washed with water, dried (MgSO$_4$) and concentrated. Purification by flash column chromatography using the Biotage system (40% methylene chloride in hexanes) provided 17 mg (35% for two steps) of the desired product (7).

Step G: Preparation of 6-(4-bromo-2-chlorophenylamino)-7-fluoro-3-methylbenzo[d]isoxazole-5-carboxylic acid methyl ester (8a): 6-(2-Chlorophenylamino)-7-fluoro-3-methylbenzo[d]isoxazole-5-carboxylic acid methyl ester (7) (18.6 mg, 0.0556 mmol) and N-bromosuccinimide (12.0 mg, 0.0667 mmol) were stirred in DMF (1 mL) for 16 hours. The reaction mixture was diluted with EtOAc, and washed with water (2×). The organic layer was dried over MgSO$_4$, filtered, and concentrated. Purification by flash column chromatography using the Biotage system (10% EtOAc in hexanes) provided 12.6 mg (55%) of the desired product (8a).

Step H: Preparation of 6-(4-bromo-2-chlorophenylamino)-7-fluoro-3-methylbenzo[d]isoxazole-5-carboxylic acid (9a): To a solution of 6-(4-bromo-2chlorophenylamino)-7-fluoro-3-methylbenzo[d]isoxazole-5-carboxylic acid methyl ester (8a) (200 mg, 0.48 mmol) in THF-water (3 mL/1.5 mL) was added aqueous LiOH (1 M, 1.00 mL) at room temperature. After 15 hours, the reaction mixture was acidified to pH 1 with aqueous HCl (1 M), diluted with water, and extracted with EtOAc/THF. The organic layer was washed with water, dried over MgSO$_4$, filtered, and concentrated in vacuo to give 191.5 mg (99%) of the crude acid (9a) which was used without further purification. MS APCI (−) m/z 397, 399 (M+, Br, Cl pattern) detected. $^1$H NMR (400 MHz, DMSO-d$_6$) δ 9.55 (s, 1H), 8.37 (s, 1H), 7.75 (s, 1H), 7.42 (d, 1H), 6.97 (t, 1H), 2.60 (s, 3H): $^{19}$F NMR (376 MHz, DMSO-d$_6$) −140.15 (s).

Example 2

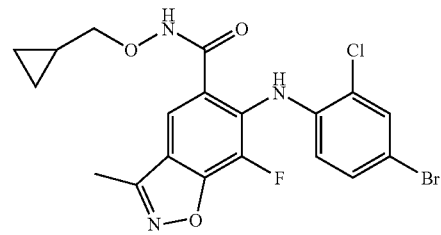

Synthesis of 6-(4-bromo-2-chlorophenylamino)-7-fluoro-3-methylbenzo[d]isoxazole-5-carboxylic acid cyclopropylmethoxyamide (10a)

To a solution of 6-(4-bromo-2-chlorophenylamino)-7-fluoro-3-methylbenzo[d]isoxazole-5-carboxylic acid (9a) (50.0 mg, 0.125 mmol) in DMF (1 mL) was added HOBt (24.6 mg, 0.161 mmol), Et$_3$N (0.060 mL, 0.43 mmol), O-cyclopropylmethyl-hydroxylamine (15.5 mg, 0.178 mmol), and 1-(3-dimethylaminopropyl)-3-ethylcarbodiimide hydrochloride (EDCI) (32.2 mg, 0.168 mmol) at room temperature. After 6 days, the reaction mixture was diluted with EtOAc, washed with saturated aqueous NH$_4$Cl, brine, saturated aqueous NaHCO$_3$, and brine. The organic layer was dried over MgSO$_4$, filtered, concentrated in vacuo, and purified by flash column chromatography using the Biotage system (0.5% MeOH in CH$_2$Cl$_2$) to give 27.6 mg (47% yield) of the desired product (10a). MS APCI (−) m/z 466, 468 (M+, Br, Cl pattern) detected. $^1$H NMR (400 MHz, CD$_3$OD) δ 7.82 (s, 1H), 7.57 (d, 1H), 7.31 (dd, 1H), 6.74 (dd, 1H), 3.73 (d, 2H), 2.60 (s, 3H), 1.16 (m, 1H), 0.55 (m, 2H), 0.28 (m, 2H). $^{19}$F NMR (376 MHz, CD$_3$OD)−140.96 (s, 1F).

Example 3

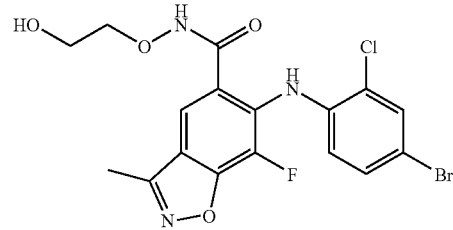

Synthesis of 6-(4-bromo-2-chlorophenylamino)-7-fluoro-3-methylbenzo[d]isoxazole-5-carboxylic acid (2-hydroxyethoxy)-amide (12a)

Step A: Preparation of 6-(4-bromo-2-chlorophenylamino)-7-fluoro-3-methyl-benzo[d]isoxazole-5-carboxylic acid (2-vinyloxyethoxy)-amide (11a): To a solution of 6-(4-bromo-2-chlorophenylamino)-7-fluoro-3-methylbenzo[d]isoxazole-5-carboxylic acid (10a) (75.2 mg, 0.188 mmol) in DMF (1.5 mL) was added HOBt (38.2 mg, 0.249 mmol), Et₃N (0.080 mL, 0.571 mmol), O-(2-vinyloxyethyl)hydroxylamine (28.5 mg, 0.276 mmol), and EDCI (47.2 mg, 0.246 mmol) at room temperature. After 6 days, the reaction mixture was diluted with EtOAc, washed with saturated aqueous NH₄Cl, brine, saturated aqueous NaHCO₃, and brine. The organic layer was dried over MgSO₄, filtered, concentrated in vacuo, and purified by flash column chromatography using the Biotage system (3% MeOH in CH₂Cl₂) to give 57.8 mg (63%) of the desired product (11a).

Step B: Preparation of 6-(4-bromo-2-chlorophenylamino)-7-fluoro-3-methylbenzo[d]isoxazole-5-carboxylic acid (2-hydroxyethoxy)-amide (12a): A solution of 6-(4-bromo-2-chlorophenylamino)-7-fluoro-3-methylbenzo[d]isoxazole-5-carboxylic acid (2-vinyloxyethoxy) amide (11a) (55.4 mg, 0.114 mmol) and aqueous HCl (1 M, 0.23 mL) in EtOH (3 mL) was stirred for 2 hours at room temperature. The pH of the reaction mixture was adjusted to 6-7 with aqueous NaOH (2 M). The reaction was diluted with EtOAc. The organic layer was washed with water, dried over MgSO₄, filtered, and concentrated in vacuo to give 50.2 mg (96% yield) of the desired product (12a). MS APCI (−) m/z 456, 458 (M+, Br, Cl pattern) detected. $^1$H NMR (400 MHz, CD₃OD) δ 7.87 (s, 1H), 7.57 (d, 1H), 7.31 (dd, 1H), 6.74 (dd, 1H), 4.01 (t, 2H), 3.74 (t, 2H), 2.60 (s, 3H): $^{19}$F NMR (376 MHz, CD₃OD)−140.85 (s).

Example 4

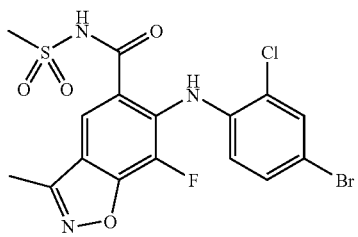

Synthesis of N-[6-(4-bromo-2-chlorophenylamino)-7-fluoro-3-methylbenzo[d]isoxazole-5-carbonyl]-methanesulfonamide (13a)

A mixture of 6-(4-bromo-2-chlorophenylamino)-7-fluoro-3-methylbenzo[d]isoxazole-5-carboxylic acid (9a) (41 mg, 0.102 mmol) and carbonyldiimidazole (23 mg, 0.140 mmol) in THF (1 mL) was stirred at 50° C. in a sealed tube reactor. The reaction mixture was cooled to room temperature and methanesulfonamide (17 mg, 0.179 mmol) was added followed by DBU (0.025 mL, 0.164 mmol). After stirring at 50° C. for 1 hour, the reaction mixture was cooled to room temperature, and diluted with EtOAc. The organic layer was washed with water, 1 N HCl, and brine. The organic layer was dried (MgSO₄) and concentrated. Purification by flash column chromatography using the Biotage system (7% MeOH in CH₂Cl₂) provided 34 mg (65% yield) of the desired product (13a). MS APCI (−) m/z 474, 476 (M+, Br, Cl pattern) detected. $^1$H NMR (400 MHz, CD₃OD) δ 8.27 (s, 1H), 7.53 (s, 1H), 7.27 (d, 1H), 6.73 (t, 1H), 3.11 (s, 3H), 2.55 (s, 3H): $^{19}$F NMR (376 MHz, CD₃OD)−141.84 (s, 1F).

Example 5

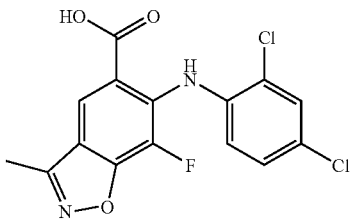

Synthesis of 6-(2,4-dichlorophenylamino)-7-fluoro-3-methylbenzo[d]isoxazole-5-carboxylic acid (9b)

Step A: Preparation of 6-(2,4-dichlorophenylamino)-7-fluoro-3-methylbenzo[d]isoxazole-5-carboxylic acid methyl ester (8b): 6-(2-Chlorophenylamino)-7-fluoro-3-methyl-benzo[d]isoxazole-5-carboxylic acid methyl ester (7) (129 mg, 0.384 mmol) and N-chlorosuccinimide (57 mg, 0.421 mmol) were stirred in DMF (5 mL) for 16 hours. Concentrated HCl (3 μL) was added and the reaction mixture stirred 2 hours. The reaction mixture was diluted with EtOAc, and washed with water (2×). The organic layer was dried over MgSO₄, filtered, and concentrated. Purification by flash column chromatography using the Biotage system (5% EtOAc in hexanes) provided 73 mg (52%) the desired product (8b).

Step B: Preparation of 6-(2,4-dichlorophenylamino)-7-fluoro-3-methylbenzo[d]isoxazole-5-carboxylic acid (9b): Compound 9b was prepared according to Step H of Example 1 using 6-(2,4-dichlorophenylamino)-7-fluoro-3-methyl-benzo[d]isoxazole-5-carboxylic acid methyl ester (8b) to provide 68 mg (98% yield) of the desired product (9b). MS APCI (−) m/z 353, 355 (M+, Br, Cl pattern) detected. $^1$H NMR (400 MHz, DMSO-d₆) δ 9.58 (s, 1H), 8.34 (s, 1H), 7.65 (d, 1H), 7.31 (dd, 1H), 7.04 (dd, 1H), 2.60 (s, 3H): $^{19}$F NMR (376 MHz, DMSO-d₆)−140.36 (s).

Example 6

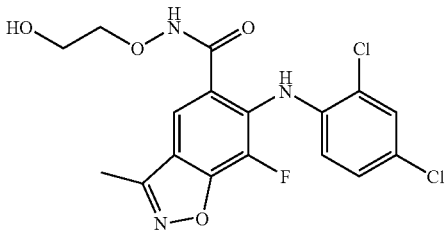

Synthesis of 6-(2,4-dichlorophenylamino)-7-fluoro-3-methylbenzo[d]isoxazole-5-carboxylic acid (2-hydroxyethoxy)amide (12b)

The synthesis of compound 12b was carried out according to Steps A and B of Example 3 using 6-(2,4-dichlrophenylamino)-7-fluoro-3-methylbenzo[d]isoxazole-5-carboxylic acid (9b) as the starting material to provide 29 mg (38% yield for two steps) of 12b. MS APCI (−) m/z 412, 414 (M+, Br, Cl pattern) detected. $^1$H NMR (400 MHz, CD$_3$OD) δ 7.87 (s, 1H), 7.45 (m, 1H), 7.19 (m, 1H), 6.80 (m, 1H), 4.02 (t, 2H), 3.75 (t, 2H), 2.60 (s, 3H): $^{19}$F NMR (376 MHz, CD$_3$OD)−141.05 (s).

Example 7

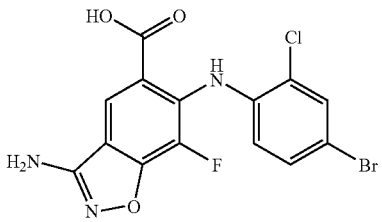

Synthesis of 3-amino-6-(4-bromo-2-chlorophenylamino)-7-fluorobenzo[d]isoxazole-5-carboxylic acid (19)

Step A: Preparation of 2-(2-chlorophenylamino)-5-cyano-3,4-difluorobenzoic acid methyl ester (15): A mixture of 5-bromo-2-(2-chlorophenylamino)-3,4-difluorobenzoic acid methyl ester (14) (3.01 g, 7.99 mmol), 1,1'-bis(diphenylphosphino)ferrocene (dppf) (93 mg, 0.162 mmol), Pd$_2$ dba$_3$ (73 mg, 0.080 mmol) and Zn(CN)$_2$ (573 mg, 4.78 mmol) in 1methyl-2-pyrrolidinone (NMP: 4.5 mL) was heated in a sealed tube reactor. After 20 hours, the reaction mixture was cooled to room temperature, quenched by the addition of 8 mL 4:1:4 (volume) mixture of saturated NH$_4$Cl, concentrated NH$_4$OH and water, and extracted with a mixture of EtOAc/THF. The combined organic extracts were washed with 4:1:4 (volume) mixture of saturated NH$_4$Cl, concentrated NH$_4$OH and water, and brine. The organic layer was dried (MgSO$_4$) and concentrated. Purification by flash column chromatography using the Biotage system (twice: 100% hexanes to 35% CH$_2$Cl$_2$ in hexanes, then 30% CH$_2$Cl$_2$ in hexanes) provided 1.33 g (52%) of the desired product (15).

Step B: Preparation of 3-amino-6-(2-chlorophenylamino)-7-fluorobenzo[d]isoxazole-5-carboxylic acid methyl ester (17): t-BuOK (3.80 mL of a 1.0 M solution in THF) was added to a stirred solution of propan-2-one oxime (285 mg, 3.82 mmol) in THF (5 mL) at room temperature. The reaction mixture was further diluted with THF (20 mL) and after 30 minutes cooled to 0° C. A solution of 2-(2-chlorophenylamino)-5-cyano-3,4-difluorobenzoic acid methyl ester (15) (600 mg, 1.86 mmol) in THF (5 mL) was added. The reaction mixture was slowly warmed to room temperature. After 90 minutes, the reaction mixture was quenched with saturated NH$_4$Cl and diluted with EtOAc. The organic layer was washed with saturated NH$_4$Cl and brine, dried (MgSO$_4$) and concentrated. The residue (16) was diluted with MeOH (10 mL) and a solution of 2 M HCl in diethyl ether (10 mL) was added. After 16 hours, the reaction mixture was diluted with EtOAc, washed with water, saturated NaHCO$_3$ and water. The organic layer was dried (MgSO$_4$) and concentrated. Purification by flash column chromatography using the Biotage system (1.5% MeOH in CH$_2$Cl$_2$) provided 399 mg (64%) of the desired product (17).

Step C: Preparation of 3-amino-6-(4-bromo-2-chlorophenylamino)-7-fluorobenzo[d]isoxazole-5-carboxylic acid methyl ester (18): Compound 18 was prepared according to Step G of Example 1 using compound 17 as the starting material.

Step D: Preparation of 3-amino-6-(4-bromo-2-chlorophenylamino)-7-fluorobenzo[d]isoxazole-5-carboxylic acid (19): Compound 19 was prepared according to Step H of Example 1 using 3-amino-6-(4-bromo-2-chlorophenylamino)-7-fluorobenzo[d]isoxazole-5-carboxylic acid methyl ester (18) as the starting material to provide 188 mg (98% yield) of compound 19. MS APCI (−) m/z 398, 400 (M+, Br, Cl pattern) detected. $^1$H NMR (400 MHz, DMSO-d$_6$) δ 9.47 (s, 1H), 8.49 (s, 1H), 7.73 (m, 1H), 7.41 (dd, 1H), 6.92 (t, 1H), 6.76 (s, 2H): $^{19}$F NMR (376 MHz, DMSO-d$_6$)−141.48 (s).

Example 8

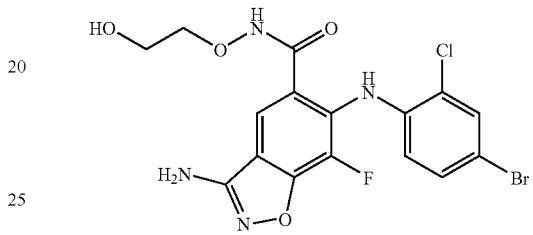

Synthesis of 3-amino-6-(4-bromo-2-chloro-phenylamino)-7-fluorobenzo[d]isoxazole-5-carboxylic acid (2-hydroxyethoxy)-amide (21).

The synthesis of compound 21 was accomplished according to Steps A and B of Example 3 using 3-amino-6-(4-bromo-2-chlorophenylamino)-7-fluorobenzo[d]isoxazole-5-carboxylic acid (19) as the starting material to provide 16 mg (23% yield for two steps) of compound 21. MS APCI (−) m/z 457, 459 (M+, Br, Cl pattern) detected. $^1$H NMR (400 MHz, DMSO-d$_6$) δ 11.92 (s, 1H), 8.59 (s, 11H), 7.94 (s, 11H), 7.69 (s, 1H), 7.36 (d, 11H), 6.75 (dd, 1H), 6.71 (s, 2H), 4.73 (s, 1H), 3.87 (s, 2H), 3.59 (s, 2H): $^{19}$F NMR (376 MHz, DMSO-d$_6$)−140.64 (s).

Example 9

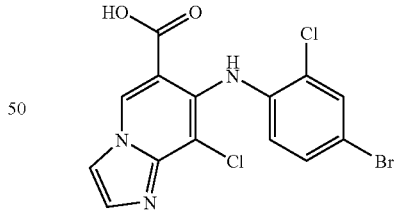

Synthesis of 7-(4-bromo-2-chlorophenylamino)-8-chloroimidazo[1,2-a]pyridine-6-carboxylic acid (30)

Step A: Preparation of 4,6-dichloronicotinic acid ethyl ester (22): POCl$_3$ (100 mL, 1092 mmol) was added to 4,6-dihydroxynicotinic acid ethyl ester (J. Heterocyclic Chem. 1983, 20, 1363) (20.0 g, 109 mmol). The resulting suspension was cooled to 0° C. and triethylamine (15.2 mL, 109 mmol) was added dropwise at such a rate as to maintain the internal reaction mixture temperature below 25° C. Upon completion of addition, the reaction mixture was warmed to room temperature and then to 80° C. After 4 hours, the reaction mixture was cooled to room temperature and stirred for 16 hours. The reaction mixture was carefully poured onto 2 L crushed ice. The mixture was extracted with EtOAc and diethyl ether. The combined organic extracts were washed with brine, dried (Na$_2$SO$_4$) and concentrated. The dark brown liquid was purified by passing through a plug of silica gel (CH$_2$Cl$_2$) to give the desired product (22) as a low melting yellow solid (18.7 g, 78%).

Step B: Preparation of 4.6-dichloronicotinic acid (23): Sodium hydroxide (40 mL, 6.25 M solution) was added to a stirred solution of 4,6-dichloronicotinic acid ethyl ester (22) (25.95 g, 118 mmol) in 4:1:1 THF/MeOH/water (600 mL). After 30 minutes, the reaction mixture was acidified to pH 2 with concentrated HCl, diluted with 1:1 EtOAc/Et$_2$O and washed with water and brine. The organic layer was dried (Na$_2$SO$_4$) and concentrated. The resulting off-white solid was twice concentrated from toluene to give the desired product (23) as a white solid (21.73 g, 96%).

Step C: Preparation of 4-(4-bromo-2-chlorophenylamino)-6-chloronicotinic acid hydrochloride salt (24): LiHMDS (261 mL of a 1 M solution in hexanes) was added dropwise over 30 minutes to a solution of 4-bromo-2-chlorophenylamine (35.0 g, 172 mmol) in THF (80 mL) at −78° C. After 1 hour, 4,6-dichloronicotinic acid (23) (15.7 g, 81.7 mmol) was added dropwise over 30 minutes. The reaction mixture was slowly warmed to room temperature and stirred 16 hours. The reaction mixture was quenched with water, diluted with EtOAc and acidified with 1 M HCl. The resulting precipitate was isolated by filtration and washed with EtOAc. The solids were twice concentrated from toluene, triturated with CH$_2$Cl$_2$ and collected by filtration. The solids were further concentrated from toluene (3x) followed by drying in vacuo to give the desired product (24) containing a small amount of water (36.0 g).

Step D: Preparation of 4-(4-bromo-2-chlorophenylamino)-5,6-dichloronicotinic acid (25): N-Chlorosuccinimide was (13.0 g, 99.0 mmol) added to a suspension of 4-(4-bromo-2-chlorophenylamino)-6-chloronicotinic acid (24) (32.54 g, 89.9 mmol) in DMF (500 mL). The suspension was allowed to stir at room temperature overnight. The reaction mixture was diluted with saturated sodium bisulfite (200 mL) and water (1L) resulting in formation of a thick white precipitate which was isolated by filtration and washed with water. The solids were dissolved into THF. Two volumes of diethyl ether were added and the organic solution washed with brine, dried over NaSO$_4$, filtered, and concentrated in vacuo to provide an orange solid. The solid was triturated with diethyl ether to provide the desired product as an off-white solid (25) (13.34 g, 37%). MS (APCI−) m/z 393, 395, 397 (M−; Cl, Br pattern) detected.

Alternatively, 4-(4-bromo-2-chlorophenylamino)-5,6-dichloronicotinic acid (25) can be synthesized by the route and procedure described below.

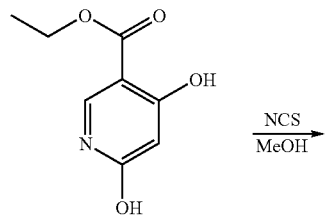

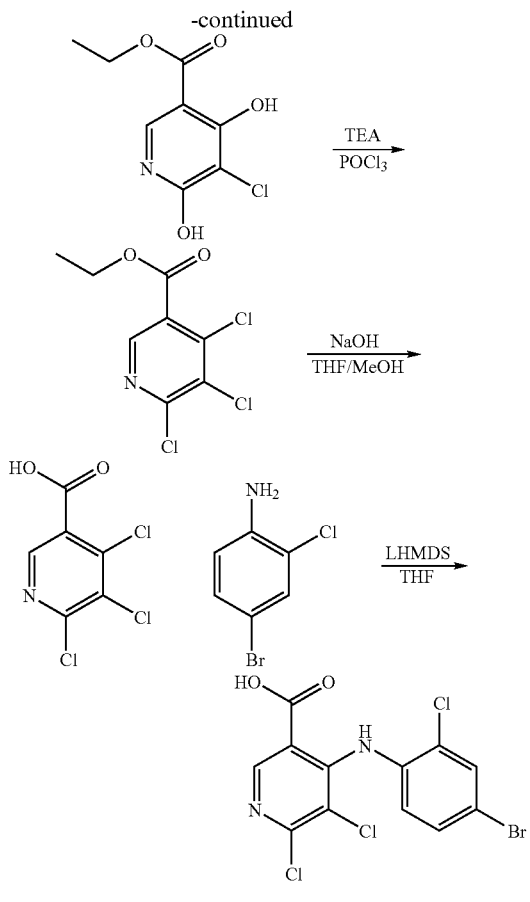

N-Chlorosuccinimide (56.5 g, 423 mmol) was added portionwise to a suspension of 4,6-dihydroxynicotinic acid ethyl ester (70.5 g, 385 mmol) in DMF (705 mL). Concentrated HCl (3.20 mL, 38.5 mmol) was added. After stirring for 2.5 hours, the product was precipitated with water and Na$_2$S$_2$O$_3$ (70 mL). The slurry was acidified to pH 3 with 2 M HCl (30 mL). 5-Chloro-4,6-dihydroxynicotinic acid ethyl ester, the desired product was isolated as a pale yellow solid (75.7 g, 90%) by filtration. MS ESI (+) m/z 218, 220 (M+, Cl pattern) detected.

5-Chloro-4,6-dihydroxynicotinic acid ethyl ester (8.05 g, 37 mmol) was suspended in phosphorous oxychloride (30 mL, 296 mmol). The mixture was cooled to 0° C. and triethylamine (5.16 mL, 37.0 mmol) was added. The reaction was heated to 60° C. for three hours. The solution was cooled to room temperature, poured onto ice, stirred for 15 minutes and extracted with ethyl acetate (2x) and diethyl ether (1x). The combined organic extracts were washed with brine (3x), dried over Na$_2$SO$_4$ and concentrated to a brown liquid. The crude product was passed through a plug of silica gel eluting with dichloromethane. 4,5,6-trichloronicotinic acid ethyl ester, the desired product was obtained as a yellow liquid (7.76 g, 82%).

Sodium hydroxide (1.0 M solution, 61.0 mL, 61.0 mmol) was added to a solution of 4,5,6-trichloronicotinic acid ethyl ester (7.76 g, 30.5 mmol) in 4:1 THF/MeOH (150 mL). After stirring for 30 minutes, the reaction was acidified to pH 1 by addition of concentrated HCl, diluted with ethyl acetate, washed with water (3x) and brine (2x), dried over Na$_2$SO$_4$ and concentrated to provide the desired product, 4,5,6-trichloro-nicotinic acid, as an off white solid (6.77 g, 98%).

LiHMDS (1.0 M solution in hexanes, 53.0 mL, 53.0 mmol) was added dropwise to a stirred solution of 4-bromo-2-chlorophenylamine (7.10 g, 35.0 mmol) in THF (15 mL) cooled to −78° C. After one hour, 4,5,6-trichloronicotinic acid (3.73 g, 16.5 mmol) was added dropwise as a solution in THF (12 mL). The reaction was allowed to warm to room temperature slowly while stirring overnight. The suspension was diluted with 1 M HCl and ethyl acetate, and the aqueous phase was extracted with ethyl acetate (3×). The combined organic phases were dried over $Na_2SO_4$ and concentrated to a tan solid. The solid was triturated with diethyl ether overnight and the solids were isolated by filtration to provide the desired product (25) as a tan-colored solid (4.85 g, 75%). MS APCI (−) m/z 395, 397 (M−, Cl, Br pattern) detected.

Step E: Preparation of 4-(4-bromo-2-chlorophenylamino)-5,6-dichloronicotinic acid methyl ester (26): Trimethylsilyldiazomethane (2.0 M solution in hexanes, 37 mL, 74 mmol) was added slowly to a suspension of 4-(4-bromo-2-chlorophenylamino)-5,6-dichloronicotinic acid (25) (14.67 g, 37 mmol). After the addition was complete the resulting slurry was diluted with hexanes (600 mL) and the solids isolated by filtration washing with hexanes. The desired product was isolated as an off-white solid (10.06 g). The hexanes washes were concentrated and the solids passed through a plug of silica gel eluting with dichloromethane. Concentration of the product-containing fractions provided an additional 3.83 g desired product (26) for a total of 13.89 g (91%). MS (APCI+) m/z 409, 411, 413 (M+; Cl, Br pattern) detected.

Step F: Preparation of 6-azido-4-(4-bromo-2-chlorophenylamino)-5-chloronicotinic acid methyl ester (27): Sodium azide (4.4 g, 68 mmol) was added to a suspension of 4-(4-bromo-2-chlorophenylamino)-5,6-dichloronicotinic acid methyl ester (26) (13.89 g, 33.8 mmol) in DMF (200 mL) and the mixture allowed to stir at room temperature overnight. The solution was diluted with water (600 mL) and the resulting white precipitate was collected by filtration and washed with water. The solids were dissolved into THF. Two volumes of diethyl ether were added and the organic solution washed with brine, dried over $NaSO_4$, filtered, and concentrated in vacuo to the desired product (27) as a light yellow solid (12.94 g, 92%).

Step G: Preparation of 6-amino-4-(4-bromo-2-chlorophenylamino)-5-chloro-nicotinic acid methyl ester (28): Zinc powder (10 g, 155 mmol) was added portionwise to a suspension of 6-azido-4-(4-bromo-2-chlorophenylamino)-5-chloronicotinic acid methyl ester (27) (12.94 g, 31 mmol) in 3:1 dichloromethane/acetic acid (300 mL). After fifteen minutes the reaction mixture was poured into 700 mL ethyl acetate, washed with water, saturated sodium bicarbonate and brine. The organic solution was dried over $NaSO_4$, filtered, and concentrated in vacuo to provide the desired product (28) as an off-white solid (11.85 g, 98%). MS (APCI+) m/z 390, 392, 394 (M+; Cl, Br pattern) detected.

Step H: Preparation of 7-(4-bromo-2-chlorophenylamino)-8-chloroimidazo[1,2-a]pyridine-6-carboxylic acid methyl ester (29): Chloroacetaldehyde (50% aqueous solution, 0.70 mL, 5.7 mmol) was added to a suspension of 6-amino-4-(4-bromo-2-chlorophenylamino)-5-chloronicotinic acid methyl ester (28) in DMF (7 mL) contained in a sealed tube. The reaction mixture was heated at 80° C. for four hours and then allowed to cool to room temperature and stir overnight. The dark brown solution was diluted with water (70 mL) the resulting light brown precipitate was collected by filtration and washed with water. The solids were dissolved into THF. Two volumes of ethyl acetate were added and the organic solution washed with brine, dried over $NaSO_4$, filtered, and concentrated in vacuo to provide a brown solid. The aqueous filtrate was extracted with ethyl acetate and the organic extracts were dried over $NaSO_4$, filtered, and concentrated in vacuo. This material was combined with the previously isolated brown solid and the combined material subjected to column chromatography (dichloromethane, followed by 20:1 dichloromethane/methanol). The desired product (29) was isolated as a light yellow solid (0.752 g, 64%). MS (APCI+) m/z 414, 416, 418 (M+; Cl, Br pattern) detected.

Step I: Preparation of 7-(4-bromo-2-chlorophenylamino)-8-chloroimidazo[1,2-a]pyridine-6-carboxylic acid (30): Sodium hydroxide (1.0 M aqueous solution, 14.6 mL, 14.6 mmol) was added to a solution of 7-(4-bromo-2-chlorophenylamino)-8-chloroimidazo[1,2-a]pyridine-6-carboxylic acid methyl ester (29) in methanol (30 mL) and the solution allowed to stir at room temperature overnight. Methanol was removed by rotary evaporation and the solution diluted with water and acidified to pH 2 by addition of 1.0 M HCl. The aqueous suspension was extracted with 4:1 ethyl acetate/THF. The organic extracts were washed with brine, dried over $NaSO_4$, filtered, and concentrated in vacuo to provide the desired product as a light orange solid (30). MS (APCI+) m/z 400, 402, 404 (M+: Cl, Br pattern) detected. $^1$H NMR (400 MHz, methanol-$d_4$) δ 9.01 (s, 1H), 7.83 (s, 1H), 7.51 (s, 2H), 7.25 (d, 1H), 6.60 (d, 1H).

The following compounds were synthesized in a similar manner as described in Example 9.

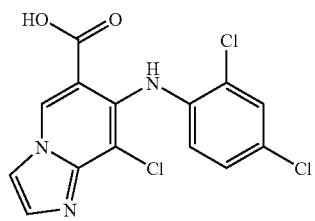

8-Chloro-7-(2,4-dichlorophenylamino)-imidazo[1,2-a]pyridine-6-carboxylic acid

MS APCI (+) m/z 356, 358 (M+, Cl pattern) detected. $^1$H NMR (400 MHz, $CD_3OD$) δ 9.16 (s, 1H), 8.00 (d, 1H), 7.72 (d, 1H), 7.51 (d, 1H), 7.25 (dd, 1H), 7.02 (d, 1H).

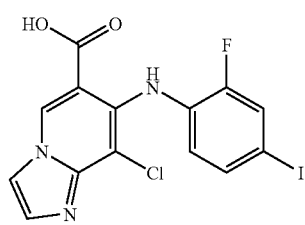

8-Chloro-7-(2-fluoro-4-iodophenylamino)-imidazo[1,2-a]pyridine-6-carboxylic acid MS APCI (+) m/z 432, 434 (M+, Cl pattern) detected. $^1$H NMR (400 MHz, DMSO-$d_6$) δ 9.31 (s, 1H), 8.11 (s, 1H), 7.71 (s, 1H), 7.61 (d, 1H), 7.37 (d, 1H), 6.62 (t, 2H).

47

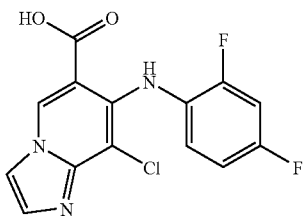

8-Chloro-7-(2,4-difluorophenylamino)-imidazo[1,2-a]pyridine-6-carboxylic acid

MS APCI (+) m/z 324, 326 (M+, Cl pattern) detected. $^1$H NMR (400 MHz, DMSO-$d_6$) δ 9.27 (s, 1H), 8.06 (s, 1H), 7.65 (s, 1H), 7.29 (t, 1H), 6.96 (m, 2H). $^{19}$F (376 MHz, DMSO-$d_6$)–118.9 (s, 1F), –124.8 (s, 1F).

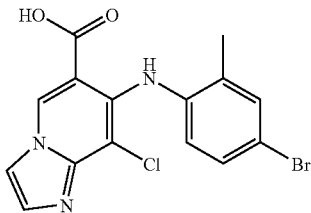

7-(4-Bromo-2-methyl-phenylamino)-8-chloroimidazo[11,2-a]pyridine-6-carboxylic acid MS APCI (+) m/z 380, 382 (M+, Cl, Br pattern) detected. $^1$H NMR (400 MHz, DMSO-$d_6$) δ 9.31 (s, 11H), 8.09 (s, 11H), 7.69 (s, 11H), 7.42 (s, 11H), 7.24 (d, 11H), 6.64 (d, 1H), 2.28 (s, 3H).

Example 10

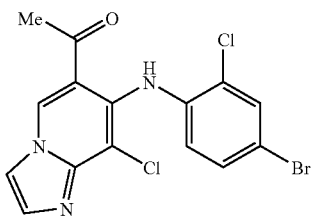

1-[7-(4-Bromo-2-chlorophenylamino)-8-chloroimidazo[1,2-a]pyridin-6-yl]-ethanone

This compound is prepared from compound 29, the product of Example 9, Step H. Tebbe reagent (μ-chloro-μ-methylene[bis(cyclopentadienyl)titanium]dimethyl-aluminum, 1 M solution in toluene, 0.12 mL, 0.12 mmol) was added to a solution of 7-(4-bromo-2-chloro-phenylamino)-8-chloro-imidazo[1,2-a]pyridine-6-carboxylic acid methyl ester (29) (25 mg, 0.061 mmol) in THF (1 mL) cooled to 0° C. The reaction mixture was warmed to room temperature and stirred for 1.5 hours. HCl (10% aqueous solution, 1 mL) was added and the mixture stirred for 16 hours. The reaction was diluted

48 with ethyl acetate, washed with saturated aqueous sodium carbonate, dried over MgSO$_4$, and concentrated. The crude material was purified by flash column chromoatography (dichloromethane to 100:1 dichloromethane/methanol) to provide the desired product (6.8 mg, 28%). MS APCI (−) m/z 396, 398, 400 (M-, Cl, Br pattern) detected. $^1$H NMR (400 MHz, CDCl$_3$) δ 9.05 (br s, 1H), 8.81 (s, 1H), 7.71 (s, 2H), 7.55 (d, 1H), 7.22 (dd, 1H), 6.55 (d, 1H), 2.67 (s, 3H).

Example 11

Preparation of 3-bromo-7-(4-bromo-2-chlorophenylamino)-8-chloro-imidazo[1,2-a]pyridine-6-carboxylic acid (2-hydroxyethoxy)-amide

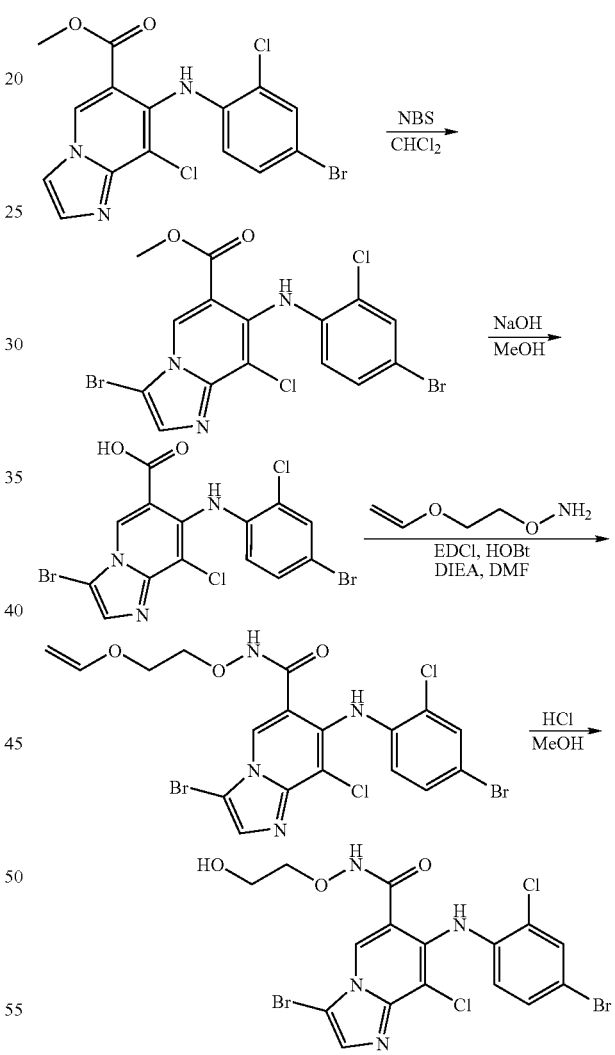

Step A: Preparation of 3-bromo-7-(4-bromo-2-chlorophenylamino)-8-chloroimidazo[1,2-a]pyridine-6-carboxylic acid methyl ester. N-bromosuccinimide (14 mg, 0.080 mmol) was added to a solution of 7-(4-bromo-2-chlorophenylamino)-8chloroimidazo[1,2-a]pyridine-6-carboxylic acid methyl ester (30 mg, 0.072 mmol) in chloroform (1.0 mL). After stirring for five hours the reaction was diluted with ethyl acetate, washed with NaHSO$_3$, brine, dried over Na$_2$SO$_4$, and concentrated to a yellow solid (33 mg, 92%). MS APCI (+)

m/z 494, 496, 498 (M+, Cl, Br pattern) detected. ¹H NMR (400 MHz, CDCl₃) δ 8.82 (s, 1H), 8.65 (s, 1H), 7.67 (s, 1H), 7.55 (dd, 1H), 7.22 (dd, 1H), 6.53 (d, 1H), 3.98 (s, 3H).

Step B: Preparation of 3-bromo-7-(4-bromo-2-chlorophenylamino)-8-chloroimidazo[1,2-a]pyridine-6-carboxylic acid (2-hydroxyethoxy)-amide. The synthesis of the title compound was carried out according to Step H of Example 1 and Steps A and B of Example 3 using 3-bromo-7-(4-bromo-2-chlorophenylamino)-8-chloroimidazo[1,2-a]pyridine-6-carboxylic acid methyl ester as the starting material to provide 20 mg of desired product as a light yellow solid. MS APCI (+) m/z 539, 541, 543 (M+, Cl, Br pattern) detected.

Example 12

Preparation of 7-(4-romo-2-chlorophenylamino)-8-chloro-3-methylimidazo[1,2-a]pyridine-6-carboxylic acid cyclopropylmethoxyamide

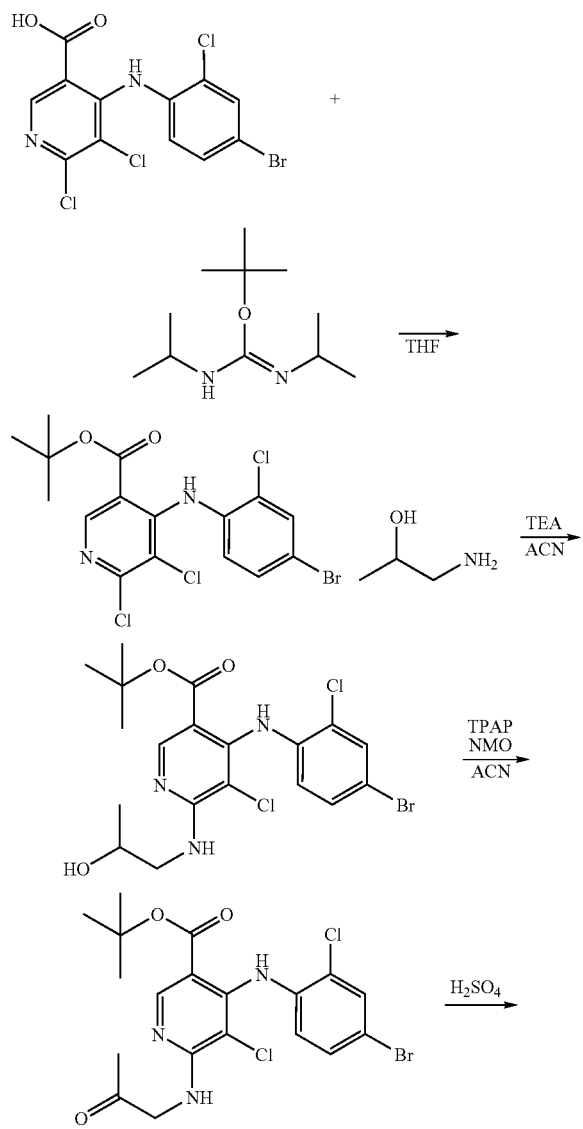

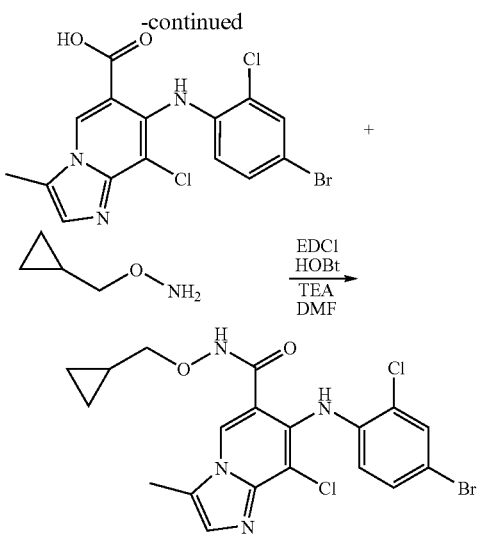

Step A: Preparation of 4-(4-bromo-2-chloroiphenylamino)-5,6-dichloronicotinic acid tert-butyl ester. 2-tert-Butyl-1,3-diisopropyl-isourea (10.6 g, 53 mmol) was added to a solution of 4-(4-bromo-2-chlorophenylamino)-5,6-dichloronicotinic acid (4.21 g, 10.6 mmol) in THF (200 mL). The reaction was heated to reflux. After 30 minutes the reaction was cooled to room temperature and diluted with EtOAc. The organic layer was washed with saturated K₂CO₃ (2×), brine, dried over Na₂SO₄ and concentrated. The yellow solid was triturated with dichloromethane and white solids were removed by filtration. The filtrate was concentrated in vacuo to yield the desired product as a yellow solid (5.53 g, 97%). MS APCI (−) m/z 451, 453 (M−, Cl, Br pattern) detected.

Step B: Preparation of 4-(4-bromo-2-chlorophenylamino)-5-chloro-6-(2-hydroxypropylamino)-nicotinic acid tert-butyl ester. I-Amino-propan-2-ol (2.44 g, 30.3 mmol) and triethylamine (0.42 mL, 3.03 mmol) were added to a solution of 4-(4-bromo-2-chlorophenylamino)-5,6-dichloronicotinic acid tert-butyl ester (1.37 g, 3.03 mmol) in acetonitrile (30 mL). The reaction was heated to reflux. After 23 hours the reaction was cooled to room temperature and diluted with EtOAc, washed with saturated NaHCO₃, water, brine, dried over Na₂SO₄ and concentrated to a white solid. Purification by flash column chromatography (20:1 dichloromethane/methanol) provided the desired product as a white solid (1.11 g, 75%). MS APCI (+) m/z 492, 494 (M+, Cl, Br pattern) detected.

Step C: Preparation of 4-(4-bromo-2-chlorophenylamino)-5-chloro-6-(2-oxopropylamino)-nicotinic acid tert-butyl ester. To a solution of 4-(4-bromo-2-chlorophenylamino)-5-chloro-6-(2-hydroxypropylamino)-nicotinic acid tert-butyl ester (0.28 g, 0.57 mmol) in acetonitrile (1.1 mL) was added 4A molecular sieves and N-methylmorpholine (0.10 g, 0.85 mmol). The mixture was cooled to 0° C. and tetrapropylammonium perruthenate (0.030 g, 0.085 mmol) was added. After stirring for one hour, the reaction was filtered through a plug of silica gel, washing with EtOAc. The filtrate was concentrated. Purification by flash column chromatography (20:1 hexanes/ethyl acetate) provided the desired product as a white solid (86 mg, 31%). MS APCI (+) m/z 490, 492 (M+, Cl, Br pattern) detected.

Step D: Preparation of 7-(4-bromo-2-chlorophenylamino)-8-chloro-3-methylimidazo[1,2-a]pyridine-6-carboxylic acid. 4-(4-Bromo-2-chlorophenylamino)-5-chloro-6-(2-oxopropylamino)-nicotinic acid tert-butyl ester (0.075 g, 0.15 mmol) was dissolved into concentrated H₂SO₄ (0.50 mL). After ten minutes, ice and water were and the mixture was stirred for ten minutes. The mixture was diluted with EtOAc, neutralized with 1 M NaOH, washed with brine, dried over Na₂SO₄ and concentrated to provide the desired product as an off-white solid. MS APCI (+) m/z 416, 418 (M+, Cl, Br pattern) detected.

Step E: Preparation of 7-(4-bromo-2-chlorophenylamino)-8-chloro-3-methylimidazo[1,2-a]pyridine-6-carboxylic acid cyclopropylmethoxy-amide. The synthesis of the title compound was carried out according to Example 2 using 7-(4-bromo-2-chlorophenylamino)-8-chloro-3-methylimidazo[1,2-a]pyridine-6-carboxylic acid as the starting material to provide 8 mg (18%) of desired product as a yellow solid. MS APCI (+) m/z 485, 487 (M+, Cl, Br pattern) detected. ¹H NMR (400 MHz, CDCl₃) δ 8.68 (s, 1H), 7.72 (m, 1H), 7.54 (m, 1H), 7.20 (dd, 1H), 6.42 (d, 1H), 3.58 (d, 2H), 2.57 (s, 3H), 0.64 (m, 1H), 0.57 (m, 2H), 0.23 (m, 2H).

Example 13

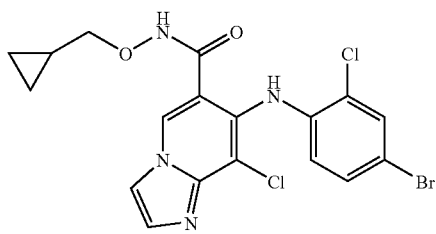

7-(4-bromo-2-chlorophenylamino)-8-chloroimidazo[1,2-a]pyridine-6-carboxylic acid cyclopropyl-methoxyamide (31)

Compound 31 was prepared according to the method of Example 2, using 7-(4-bromo-2-chlorophenylamino)-8-chloroimidazo[1,2-a]pyridine-6-carboxylic acid (30) as the starting material to provide 4.1 g (53% yield) of compound 31. MS (APCI−) m/z 467, 469, 471 (M−: Cl, Br pattern) detected. ¹H NMR (400 MHz, CD₃OD) δ 8.76 (s, 1H), 7.95 (d, 1H), 7.64 (d, 1H), 7.56 (d, 1H), 7.26 (dd, 1H), 6.56 (d, 1H), 3.57 (d, 2H), 1.10 (m, 1H), 0.54 (m, 2H), 0.24 (m, 2H).

The following compounds were synthesized in a similar manner as described in Example 9 using the appropriate aniline in Step C.

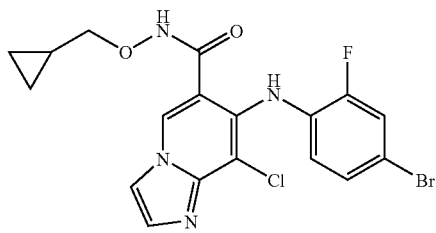

7-(4-Bromo-2-fluorophenylamino)-8-chloroimidazo[1,2-a]pyridine-6-carboxylic acid cyclopropyl-methoxyamide MS ESI (+) m/z 453, 455, 457 (M+, Cl, Br pattern) detected. ¹H NMR (400 MHz, CD₃OD) δ 8.70 (s, 1H), 7.95 (s, 1H), 7.67 (s, 1H), 7.34 (m, 1H), 7.20 (m, 1H), 6.79 (m, 1H), 3.49 (m, 2H), 1.08 (m, 1H), 0.55 (m, 2H), 0.26 (m, 2H). ¹⁹F NMR (376 MHz, CD₃OD) δ −127.4.

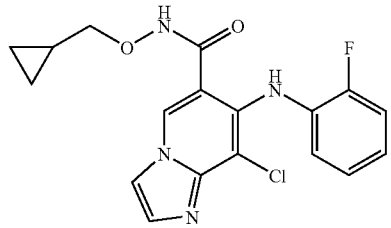

8-chloro-7-(2-fluorophenylamino)-imidazo[1,2-a]pyridine-6-carboxylic acid cyclopropylmethoxyamide MS ESI (+) m/z 375, 377 (M+, Cl pattern) detected. ¹H NMR (400 MHz, CD₃OD) δ 8.70 (s, 1H), 7.91 (s, 1H), 7.60 (s, 1H), 7.09 (m, 1H), 7.00 (m, 1H), 6.95 (m, 1H), 6.77 (m, 1H), 3.47 (d, 2H), 1.05 (m, 1H), 0.51 (m, 2H), 0.22 (m, 2H). ¹⁹F NMR (376 MHz, CD₃OD) δ −132.1.

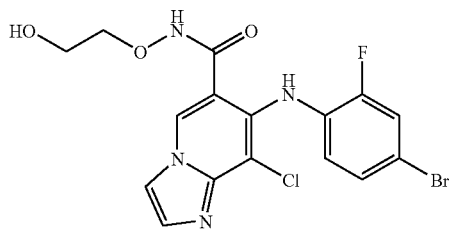

7-(4-bromo-2-fluorophenylamino)-8-chloroimidazo[1,2-a]pyridine-6-carboxylic acid (2-hydroxyethoxy)-amide MS ESI (+) m/z 443, 445, 447 (M+, Cl, Br pattern) detected. ¹H NMR (400 MHz, CD₃OD) δ 8.74 (s, 1H), 7.91 (s, 1H), 7.61 (s, 1H), 7.32 (m, 1H), 7.16 (m, 1H), 6.68 (m, 1H), 3.84 (t, 2H), 3.66 (t, 2H). ¹⁹F NMR (376 MHz, CD₃OD) δ −128.9.

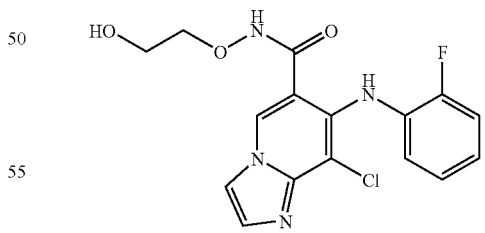

8-Chloro-7-(2-fluorophenylamino)-imidazo[1,2-a]pyridine-6-carboxylic acid (2-hydroxyethoxy)-amide MS ESI (+) m/z 365, 367 (M+, Cl pattern) detected. ¹H NMR (400 MHz, CD₃OD) δ 8.73 (s, 1H), 7.89 (s, 1H), 7.59 (s, 1H), 7.10 (m, 1H), 7.00 (m, 1H), 6.94 (m, 1H), 6.77 (m, 1H), 3.78 (t, 2H), 3.62 (t, 2H). ¹⁹F NMR (376 MHz, CD₃OD) δ −131.9.

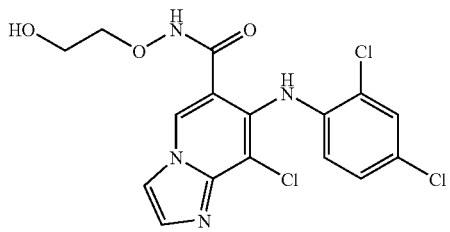

8-chloro-7-(2,4-dichlorophenylamino)-imidazo[1,2-a]pyridine-6-carboxylic acid (2-hydroxyethoxy) amide MS APCI (−) m/z 413, 415, 417 (M−, Cl pattern) detected. ¹H NMR (400 MHz, CD₃OD) δ 8.78 (s, 1H), 7.90 (s, 1H), 7.87 (s, 1H), 7.10 (dd, 1H), 6.61 (d, 1H), 4.0 (m, 2H), 3.72 (m, 2H).

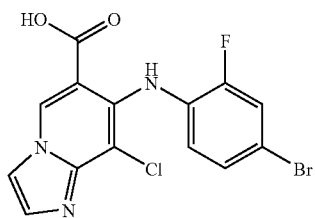

7-(4-Bromo-2-fluorophenylamino)-8-chloroimidazo[1,2-a]pyridine-6-carboxylic acid MS ESI (+) m/z 384, 386, 388 (M+, Cl, Br pattern) detected. ¹H NMR (400 MHz, DMSO-d₆) δ 9.29 (s, 1H), 8.10 (s, 1H), 7.68 (s, 1H), 7.53 (m, 1H), 7.23 (m, 1H), 6.75 (m, 1H). ¹⁹F NMR (376 MHz, DMSO-d₆) δ −127.9.

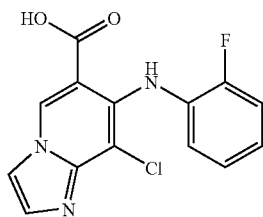

8-Chloro-7-(2-fluorophenylamino)-imidazo[1,2-a]pyridine-6-carboxylic acid

MS ESI (+) m/z 306, 308 (M+, Cl pattern) detected. ¹H NMR (400 MHz, DMSO-d₆) δ 9.30 (s, 1H), 8.09 (s, 1H), 7.67 (s, 1H), 7.22 (dd, 1H), 7.06 (dd, 1H), 6.98 (m, 1H), 6.84 (m, 1H). ¹⁹F NMR (376 MHz, DMSO-d₆) δ −130.5.

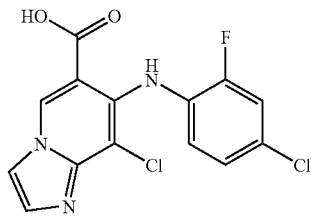

8-Chloro-7-(4-chloro-2-fluorophenylamino)-imidazo[1,2-a]pyridine-6-carboxylic acid MS ESI (+) m/z 340, 342 (M+, Cl pattern) detected. ¹H NMR (400 MHz, DMSO-d₆) δ 9.29 (s, 1H), 8.10 (s, 1H). 7.68 (s, 1H), 7.43 (m, 1H), 7.12 (m, 1H), 6.83 (m, 1H). ¹⁹F NMR (376 MHz, DMSO-d₆) δ −127.8.

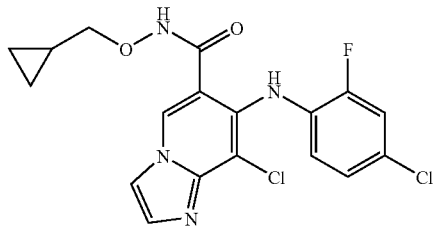

8-Chloro-7-(4-chloro-2-fluorophenylamino)-imidazo[1,2-a]pyridine-6-carboxylic acid cyclopropyl-methoxyamide MS ESI (+) m/z 409, 411 (M+, Cl pattern) detected. ¹H NMR (400 MHz, CD₃OD) δ 9.97 (br s, 1H), 8.82 (s, 1H). 7.73 (s, 1H), 7.71 (s, 1H), 7.18 (m, 1H), 6.97 (m, 1H), 6.56 (m, 1H), 6.47 (br s, 1H), 3.60 (m, 2H), 1.00 (m, 1H), 0.56 (m, 2H), 0.24 (m, 2H). ¹⁹F NMR (376 MHz, CD₃OD) δ −128.7.

Example 14

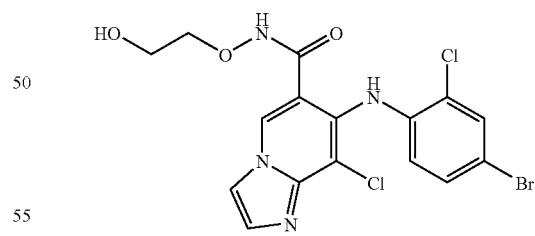

Synthesis of 7-(4-bromo-2-chlorophenylamino)-8-chloroimidazo[1,2-a]pyridine-6-carboxylic acid (2-hydroxyethoxy)-amide (33a)

Compound 33a was prepared according to Steps A and B of Example 3 using 7-(4-bromo-2-chlorophenylamino)-8-chloroimidazo[1,2-a]pyridine-6-carboxylic acid (30) to provide 44 mg (40% yield for two steps) of the desired product. MS (APCI+) m/z 459, 461, 463 (M+: Cl, Br pattern) detected.

¹H NMR (400 MHz, methanol-d₄) δ 8.90 (s, 1H), 8.08 (s, 1H), 7.93 (s, 1H), 7.69 (s, 1H), 7.45, (d, 1H), 7.06 (m, 1H), 3.86 (br s, 2H), 3.72 (br s, 2H).

Example 15

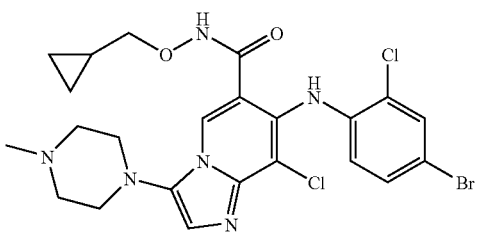

Synthesis of 7-(4-bromo-2-chlorophenylamino)-8-chloro-3-(4-methylpiperazin-1-yl)-imidazo[1,2-a]pyridine-6-carboxylic acid cyclopropylmethoxyamide (36)

Step A: 7-(4-Bromo-2-chlorolphenylamino)-8-chloro-3-(4-methylpiperazin-1-yl)-imidazo[1,2-a]pyridine-6-carboxylic acid methyl ester (34): Preparation was accomplished by modification of the procedure of Katritzky et al. (J. Org. Chem., 2003, 68, 4935-4937; J. Org. Chem., 1990, 55, 3209-3213). Bis(benzotriazazole) adduct (formed with 1-methylpiperazine) (106 mg, 0.230 mmol) was added to a suspension of 6-amino-4-(4-bromo-2-chlorophenylamino)-5-chloronicotinic acid methyl ester (28) (30 mg, 0.076 mmol) in dichloroethylene (1 mL) followed by the addition of ZnBr₂ (52 mg, 0.230 mmol). The reaction mixture was stirred at reflux for 10 hours and then at room temperature for 16 hours. The reaction mixture was diluted with CH₂Cl₂ and filtered. The filtrate was washed with water. The aqueous layer was extracted with CH₂Cl₂. The combined organic extracts were washed with brine, dried (Na₂SO₄) and concentrated. Purification by flash column chromatography using the Biotage system (60:1 CH₂Cl₂:MeOH) provided the desired product (34) as a yellow solid (31 mg, 79%).

Step B: 7-(4-Bromo-2-chlorophenylamino)-8-chloro-3-(4-methylpiperazin-1-yl)-imidazo[1,2-a]pyridine-6-carboxylic acid cyclopropylmethoxyamide (36): Sodium hydroxide (59 µL, 1 M solution) was added to a suspension of 7-(4-bromo-2-chlorophenylamino)-8-chloro-3-(4-methylpiperazin-1-yl)-imidazo[1,2-a]pyridine-6-carboxylic acid methyl ester (34) in MeOH (1 mL). After stirring 18 hours, the reaction mixture was concentrated to dryness. The residue (35) was diluted with toluene and concentrated (repeated), and 31 mg of the recovered yellow residue (35) was carried forward without purification. The residue (35) was suspended in CH₂Cl₂ (1 mL), cooled to 0° C. and oxalyl chloride (150 µL of a 2 M solution in CH₂Cl₂) was added. One drop of DMF was added and the reaction mixture warmed to room temperature. After 10 minutes, concentration of the mixture was followed by concentrating from toluene twice and then drying in vacuo. The resulting yellow solid was suspended in CH₂Cl₂ (1 mL), cooled to 0° C. and cyclopropylmethylhydroxylamine (16 mg, 0.180 mmol) was added. After the reaction mixture was warmed to room temperature and stirred for 16 hours, it was diluted with EtOAc. The organic layer was washed with saturated NaHCO₃ and brine, dried (Na₂SO₄) and concentrated. Purification by flash column chromatography using the Biotage system (15:1 CH₂Cl₂/MeOH) provided the desired product (36) as a pale yellow solid (12 mg, 37%). MS ESI (+) m/z 567, 569, 571 (M+, Cl, Br pattern) detected.
¹H NMR (400 MHz, CD₃OD) δ 8.35 (s, 1H), 7.55 (d, 1H), 7.38 (s, 1H), 7.25 (dd, 1H), 6.54 (d, 1H), 3.59 (d, 2H), 3.17 (t, 4H), 2.74 (m, 4H), 2.43 (s, 3H), 1.09 (m, 1H), 0.54 (m, 2H), 0.24 (m, 2H).

Example 16

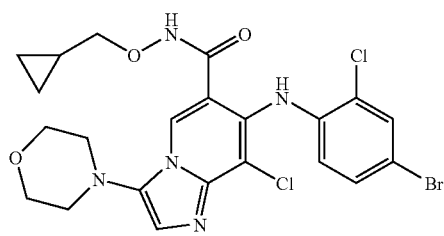

Synthesis of 7-(4-bromo-2-chlorophenylamino)-8-chloro-3-morpholin-4-yl-imidazo[1,2-a]-pyridine-6-carboxylic acid cyclopropylmethoxyamide (37)

Compound 37 was prepared according to Steps A and B of Example 15 using 6-amino-4-(4-bromo-2-chlorophenylamino)-5-chloronicotinic acid methyl ester (28) and the bis(benzotriazazole) adduct (formed with morpholine) to provide 2 mg (8% yield for two steps) of the desired product (37). MS ESI (+) m/z 554, 556, 558 (M+, Cl, Br pattern) detected.
¹H NMR (400 MHz, CD₃OD) δ 8.41 (s, 1H), 7.55 (d, 1H), 7.38 (s, 1H), 7.26 (dd, 1H), 6.54 (d, 1H), 3.91 (t, 4H), 3.59 (d, 2H), 3.11 (t, 4H), 1.08 (m, 1H), 0.54 (m, 2H), 0.24 (m, 2H).

Example 17

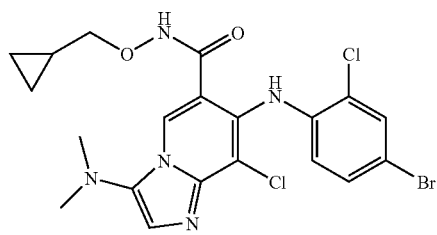

Synthesis of 7-(4-bromo-2-chlorophenylamino)-8-chloro-3-dimethylaminoimidazo[1,2-a]pyridine-6-carboxylic acid cyclopropylmethoxyamide (38)

Compound 38 was prepared according to Steps A and B of Example 15 using 6-amino-4-(4-bromo-2-chlorophenylamino)-5-chloronicotinic acid methyl ester (28) and the bis(benzotriazazole) adduct (formed with dimethylamine) providing 16 mg (37% yield for two steps) of the desired product (38). MS ESI (+) m/z 512, 514, 516 (M+, Cl, Br pattern) detected. ¹H NMR (400 MHz, CD₃OD) δ 8.37 (s, 1H), 7.54 (d, 1H), 7.30 (s, 1H), 7.24 (dd, 1H), 6.52 (d, 1H), 3.59 (d, 2H), 2.86 (s, 6H), 1.07 (m, 1H), 0.53 (m, 2H), 0.23 (m, 2H).

Example 18

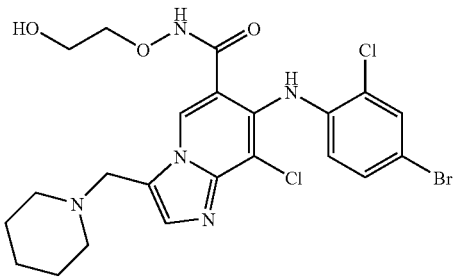

Synthesis of 7-(4-bromo-2-chlorophenylamino)-8-chloro-3-piperidin-1-ylmethylimidazo[1,2-a]pyridine-6-carboxylic acid (2-hydroxyethoxy) amide (39)

Compound 39 was prepared by a modification of the procedure of T. Kercher et al. (manuscript in preparation). Piperidine (4 μL, 0.043 mmol) and 37% aqueous formaldehyde (5 μL, 0.065 mmol) were dissolved in 6:1 MeCN:water (0.5 ml), and stirred 30 minutes. 7-(4-bromo-2-chlorophenylamino)-8-chloroimidazo[1,2-a]pyridine-6-carboxylic acid (2-hydroxyethoxy)amide (33a) (10 mg, 0.022 mmol) was added followed by scandium triflate (1 mg, 0.002 mmol). After stirring 16 hours, additional scandium triflate (1 mg), piperidine (3.8 μL) and aqueous formaldehyde (3.8 μL) were added. After about 60 hours, the reaction mixture was diluted with EtOAc and washed with water, 10% $K_2CO_3$, and brine. The organic layer was dried ($Na_2SO_4$) and concentrated. Purification by flash column chromatography using the Biotage system (40:1 $CH_2Cl_2$/MeOH to 20:1 $CH_2Cl_2$:MeOH to 9:1 $CH_2Cl_2$/MeOH) provided the desired product (39) as a white solid (6 mg, 50%). MS APCI (+) m/z 556, 558, 560 (M+, Cl, Br pattern) detected. $^1$H NMR (400 MHz, $CD_3OD$) δ 8.83 (s, 1H), 7.56 (s, 1H), 7.54 (s, 1H), 7.27 (dd, 1H), 6.56 (d, 1H), 3.91 (m, 4H), 3.70 (m, 2H), 2.51 (broad s, 4H), 1.60 (broad s, 4H), 1.50 (broad s, 2H).

The following compounds were synthesized in a similar manner as described in Example 18.

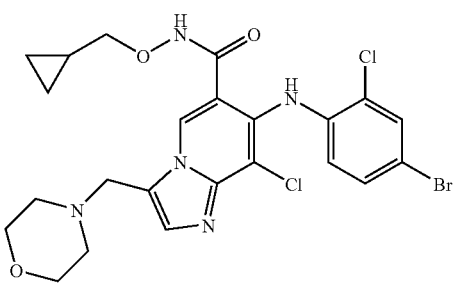

7-(4-Bromo-2-chlorophenylamino)-8-chloro-3-morpholin-4-ylmethyl-imidazo[1,2-a]pyridine-6-carboxylic acid cyclopropylmethoxyamide The reaction scheme for the synthesis of 7-(4-bromo-2-chlorophenylamino)-8-chloro-3-morpholin-4-ylmethylimidazo[1,2-a]pyridine-6-carboxylic acid cyclopropylmethoxyamide is similar to that described in Example 18 using 7-(4-bromo-2-chlorophenylamino)-8-chloroimidazo[1,2-a]pyridine-6-carboxylic acid (2-hydroxyethoxy)amide (33a) and morpholine to provide the desired product. MS APCI (+) m/z 568, 570, 572 (M+, Cl, Br pattern) detected; $^1$H NMR (400 MHz, $CDCl_3$) δ 8.76 (s, 1H), 8.04 (s, 1H), 7.56 (d, 1H), 7.21 (dd, 1H), 6.68 (d, 1H), 4.51 (s, 2H), 4.00 (m, 4H), 3.78 (d, 2H), 1.68 (m, 1H), 0.56 (m, 2H), 0.26 (m, 2H).

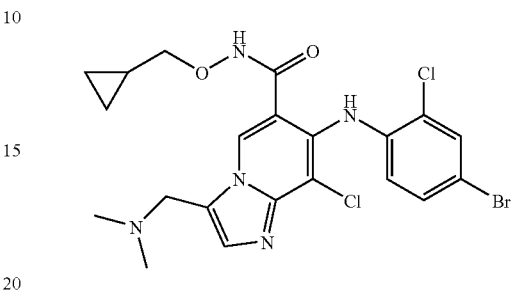

7-(4-Bromo-2-chlorophenylamino)-8-chloro-3-dimethylaminomethylimidazo[1,2-a]pyridine-6-carboxylic acid cyclopropylmethoxyamide The reaction scheme for the synthesis of 7-(4-bromo-2-chlorophenylamino)-8-chloro-3-dimethylaminomethylimidazo[1,2-a]pyridine-6-carboxylic acid cyclopropylmethoxyamide was similar to that described in Example 18, using 7-(4-bromo-2-chlorophenylamino)-8-chloroimidazo[1,2-a]pyridine-6-carboxylic acid (2-hydroxyethoxy)amide (33a) and dimethylamine to provide the desired product. MS APCI (+) m/z 528, 530, 532 (M+, Cl, Br pattern) detected; $^1$H NMR (400 MHz, $CD_3OD$) δ 8.71 (s, 1H), 7.50 (d, 1H), 7.44 (s, 1H), 7.20 (dd, 1H), 6.55 (d, 1H), 3.80 (s, 2H), 3.74 (d, 2H), 2.04 (s, 6H), 1.18 (m, 1H), 0.51 (m, 2H), 0.27 (m, 2H).

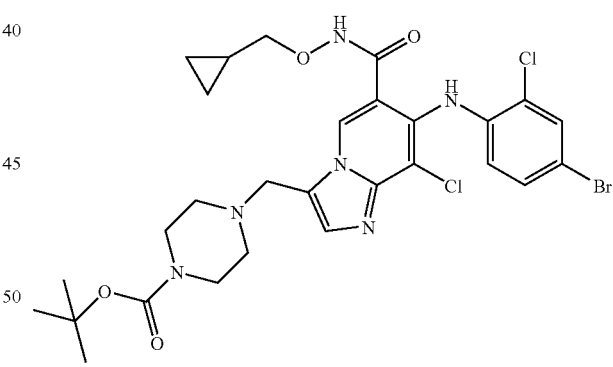

4-[7-(4-Bromo-2-chlorophenylamino)-8-chloro-6-cyclopropylmethoxycarbamoylimidazo[1,2-a]pyridin-3-ylmethyl]-piperazine-1carboxylic acid tert-butyl ester The reaction scheme for the synthesis of 4-[7-(4-bromo-2-chlorophenylamino)-8-chloro-6-cyclopropylmethoxycarbamoylimidazo[1,2-a]pyridin-3-ylmethyl]-piperazine-1-carboxylic acid tert-butyl ester was similar to that to that described in Example 18, using 7-(4-bromo-2-chlorophenylamino)-8-chloroimidazo[1,2-a]pyridine-6-carboxylic acid (2-hydroxyethoxy)amide (33a) and piperazine-1-carboxylic acid tert-butyl ester to provide the desired product. MS APCI (+) m/z 669, 671, 673 (M+, Cl, Br pattern) detected; $^1$H NMR (400 MHz, CDCl$_3$) δ 8.80 (s, 1H), 8.00 (s, 1H), 7.56 (d, 1H), 7.27 (dd, 1H), 6.67 (d, 1H), 4.54 (s, 2H), 3.76 (d, 4H), 3.27 (m, 4H), 1.50 (s, 9H), 1.12 (m, 1H), 0.55 (m, 2H), 0.28 (m, 2H).

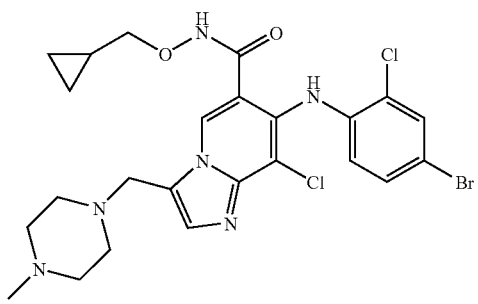

7-(4-Bromo-2-chlorophenylamino)-8-chloro-3-(4-methylpiperazin-1-ylmethyl)-imidazo[1,2-a]pyridine-6-carboxylic acid cyclopropylmethoxyamide The reaction scheme for the synthesis of 7-(4-bromo-2-chlorophenylamino)-8-chloro-3-(4-methylpiperazin-1-ylmethyl)-imidazo[1,2-a]pyridine-6-carboxylic acid cyclopropylmethoxyamide was similar to that described in Example 18, using 7-(4-bromo-2-chlorophenylamino)-8-chloroimidazo[1,2-a]pyridine-6-carboxylic acid (2-hydroxyethoxy) amide (33a) and 1-methylpiperazine to provide the desired product. MS APCI (+) m/z 581, 583, 585 (M+, Cl, Br pattern) detected; $^1$H NMR (400 MHz, CDCl$_3$) δ 8.90 (s, 1H), 7.57 (s, 1H), 7.56 (d, 1H), 7.22 (dd, 1H), 6.47 (d, 1H), 3.83 (s, 2H), 3.60 (d, 2H), 2.47 (m, 8H), 2.31 (s, 3H), 1.02 (m, 1H), 0.56 (m, 2H), 0.26 (m, 2H).

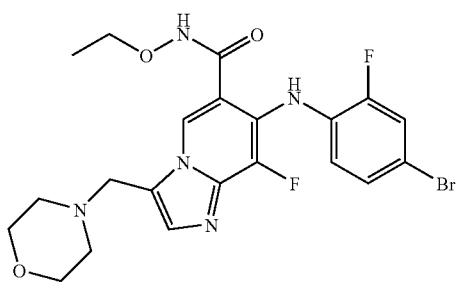

7-(4-Bromo-2-fluorophenylamino)-8-fluoro-3-morpholin-4-ylmethylimidazo[1,2-a]pyridine-6-carboxylic acid ethoxyamide The reaction scheme for the synthesis of 7-(4-bromo-2-fluorophenylamino)-8-fluoro-3-morpholin-4-ylmethylimidazo[1,2-a]pyridine-6-carboxylic acid ethoxyamide is similar to that described in Example 18 using 7-(4-bromo-2-fluorophenylamino)-8-fluoro-imidazo[1,2-a]pyridine-6-carboxylic acid ethoxyamide and morpholine to provide the desired product. MS ESI (+) m/z 510, 512 (M+, Br pattern) detected. $^1$H NMR (400 MHz, CD$_3$OD) δ 8.72 (s, 1H), 7.39 (s, 1H), 7.29 (dd, 1H), 7.17 (d, 1H), 6.76 (m, 1H), 3.99 (q, 2H), 3.85 (s, 2H), 3.68 (m, 4H), 2.49 (br s, 4H), 1.29 (t, 3H). $^{19}$F NMR (376 MHz, CD$_3$OD)–129.97 (s, 1F), –142.85 (s).

Example 19

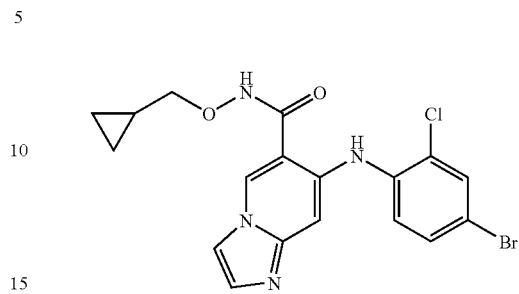

Synthesis of 7-(4-bromo-2-chlorophenylamino)-imidazo[1,2-a]pyridine-6-carboxylic acid cyclopropylmethoxyamide (44a)

Step A: Preparation of 4-(4-bromo-2-chlorophenylamino)-6-chloronicotinic acid tert-butyl ester (40): 2-tert-Butyl-1,3-diisopropylisourea (8.04 g, 40.1 mmol) was added to a mixture of 4-(4-bromo-2-chlorophenylamino)-6-chloronicotinic acid hydrochloride salt (24) (2.91 g, 7.31 mmol) in THF (165 mL). After stirring for 2 hours at room temperature and 30 minutes at reflux, the reaction mixture was cooled to room temperature and diluted with EtOAc. The organic layer was washed with 10% K$_2$CO$_3$ and brine, dried (Na$_2$SO$_4$) and concentrated. The resulting residue was dissolved in CH$_2$Cl$_2$ and filtered. The filtrate was concentrated and purified by flash column chromatography using the Biotage system (CH$_2$Cl$_2$) to give the desired product (40) (3.28 g, 78%).

Step B: Preparation of 6-azido-4-(4-bromo-2-chlorophenylamino)nicotinic acid tert-butyl ester (41): Sodium azide (1.51 g, 23.2 mmol) was added to a suspension of 4-(4-bromo-2-chlorophenylamino)-6-chloronicotinic acid tert-butyl ester (40) (3.23 g, 7.73 mmol) in DMF (60 mL). The reaction mixture was heated to 80° C. and stirred for 16 hours. After cooling to room temperature, the reaction was diluted with EtOAc and washed with water, saturated NaHCO$_3$ and brine. The organic layer was dried (Na$_2$SO$_4$) and concentrated. Purification by flash column chromatography using the Biotage system (CH$_2$Cl$_2$) (repeated) provided the desired product (41) (1.41 g, 43%).

Step C: Preparation of 6-amino-4-(4-bromo-2-chlorophenylamino)-nicotinic acid tert-butyl ester (42): Compound 42 was prepared as described in Step G of Example 9 using 6-azido-4-(4-bromo-2-chlorophenylamino)nicotinic acid tert-butyl ester (41).

Step D: Preparation of 7-(4-bromo-2-chlorophenylamino) imidazo[1,2-a]pyridine-6-carboxylic acid (43): Chloroacetaldehyde (12 μL, 0.188 mmol) was added to a mixture of 6-amino-4-(4-bromo-2-chlorophenylamino)-nicotinic acid tert-butyl ester (42) (50 mg, 0.125 mmol) in EtOH (630 μL). After stirring the reaction mixture at 80° C. for 5 hours, an additional 12 μL of chloroacetaldehyde were added and heating was continued for 10 hours. The reaction mixture was cooled to room temperature and diluted with EtOAc to give a cloudy semi-solution. The organic layer was washed with water, saturated NaHCO$_3$ and brine. The organic layer contains a precipitate, which was collected by filtration to give the desired product (43) (15 mg, 33%). MS APCI (–) m/z 364, 366, (M-, Cl, Br pattern) detected. $^1$H NMR (400 MHz, DMSO-d$_6$) δ 9.12 (s, 1H), 8.31 (s, 1H), 7.91 (s, 1H), 7.80 (s, 1H), 7.65-7.54 (m, 2H), 6.91 (s, 1H).

Step E: Preparation of 7-(4-bromo-2-chlorophenylamino)-imidazo[112-a]pyridine-6-carboxylic acid cyclopropylmethoxyamide (44a): Oxalyl chloride (2.0 M solution in CH$_2$Cl$_2$, 102 µL) was added to a stirred suspension of 7-(4-bromo-2-chlorophenylamino)imidazo[1,2-a]pyridine-6-carboxylic acid (43) (15 mg, 0.041 mmol) in CH$_2$Cl$_2$ (1 mL) at 0° C. One drop of DMF was added. The reaction mixture was warmed to room temperature, stirred for 25 minutes, and then concentrated. The residue was twice concentrated from toluene and dried in vacuo. The residue was suspended in CH$_2$Cl$_2$ (1 mL), cooled to 0° C. and cyclopropylmethylhydroxylamine (36 mg, 0.409 mmol) was added. The reaction mixture was warmed to room temperature, stirred for 2 hours and diluted with EtOAc. The organic layer was washed with saturated NaHCO$_3$ and brine, dried (Na$_2$SO$_4$) and concentrated. Purification by flash column chromatography using the Biotage system (40:1 CH$_2$Cl$_2$/MeOH to 20:1 CH$_2$Cl$_2$/MeOH) provided the desired product (44a) as a tan solid (6 mg, 31%). MS APCI (−) m/z 433, 435 (M−, Cl, Br pattern) detected. $^1$H NMR (400 MHz, CDCl$_3$) δ 8.68 (s, 1H), 7.69 (m, 1H), 7.67 (d, 1H), 7.52-7.44 (m, 3H), 7.08 (s, 1H), 3.83 (d, 2H), 0.90 (m, 1H), 0.62 (m, 2H), 0.35 (m, 2H).

The following compounds were synthesized in a similar manner as described in Example 18, using the appropriate aniline in Step C.

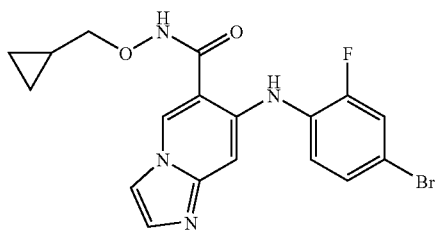

7-(4-Bromo-2-fluorophenylamino)-imidazo[1,2-a]pyridine-6-carboxylic acid

MS ESI (+) m/z 350, 352 (M+, Br pattern) detected. (400 MHz, DMSO-d$_6$) δ 9.13 (s, 1H), 7.94 (d, 1H). 7.70 (dd, 1H), 7.67 (d, 1H), 7.59 (t, 1H), 7.47 (m, 1H), 6.84 (s, 1H). $^{19}$F NMR (376 MHz, DMSO-d$_6$) δ −128.9.

7-(4-Bromo-2-fluorophenylamino)-imidazo[1,2-a]pyridine-6-carboxylic acid cyclopropylmethoxyamide MS ESI (+) m/z 419, 421 (M+, Br pattern) detected. $^1$H NMR (400 MHz, DMSO-d$_6$) δ 11.91 (br s, 1H), 8.79 (s, 1H), 8.72 (br s, 1H), 7.81 (s, 2H), 7.64 (m, 1H), 7.50 (m, 1H), 7.45 (m, 1H), 7.39 (m, 1H), 6.90 (s, 1H), 3.74 (d, 2H), 1.14 (m, 1H), 0.55 (m, 2H), 0.29 (m, 2H). $^{19}$F NMR (376 MHz, DMSO-d$_6$) δ −124.3.

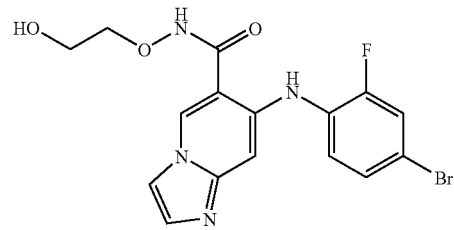

7-(4-bromo-2-fluorophenylamino)-imidazo[1,2-a]pyridine-6-carboxylic acid (2-hydroxyethoxy)-amide MS ESI (+) m/z 409, 411 (M+, Br pattern) detected. $^1$H NMR (400 MHz, DMSO-d$_6$) δ 12.02 (br s, 1H), 8.83 (s, 1H), 7.80 (s, 1H), 7.63 (s, 1H), 7.51 (m, 1H), 7.45 (m, 1H), 7.39 (m, 1H), 6.91 (s, 1H), 4.79 (br s, 1H), 3.94 (t, 2H), 3.64 (t, 2H). $^{19}$F NMR (376 MHz, DMSO-d$_6$) δ −124.4.

Example 20

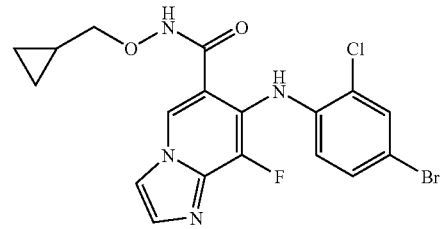

Synthesis of 7-(4-bromo-2-chlorophenylamino)-8-fluoroimidazo[1,2-a]pyridine-6-carboxylic acid cyclopropylmethoxyamide (47a)

Step A: Preparation of 6-amino-4-(4-bromo-2-chlorophenylamino)-5-fluoronicotinic acid tert-butyl ester (45): 1-Chloromethyl-4-fluoro-1,4-diazoniabicyclo[2.2.2]octane bis(tetrafluoroborate) (889 mg, 2.508 mmol) was added to a mixture of 6-amino-4-(4-bromo-2-chlorophenylamino)nicotinic acid tert-butyl ester (42) (1.00 g, 2.51 mmol) in 1:1 MeOH/water (25 mL). After about 2 hours, the reaction mixture was diluted with EtOAc and water. The layers were separated and the organic layer washed with 0.5 N HCl and brine. The aqueous washes were back extracted with EtOAc. The combined organic extracts were dried (Na$_2$SO$_4$) and concentrated. Purification by flash column chromatography using the Biotage system (20:1 hexanes/EtOAc to 15:1 hexanes/EtOAc) provided the desired product (45) as a yellow solid (75 mg, 7%).

Step B: Preparation of 7-(4-bromo-2-chlorophenylamino)-8-fluoroimidazo[1,2-a]pyridine-6-carboxylic acid (46): Chloroacetaldehyde (23 µL, 0.360 mmol) was added to a mixture of 6-amino-4-(4-bromo-2-chlorophenylamino)-5-fluoronicotinic acid tert-butyl ester (45) (75 mg, 0.180 mmol) in EtOH (1 mL). After stirring the reaction mixture at 70° C. for 10 hours, an additional 10 µL chloroacetaldehyde was added and heating was continued for 33 hours. The reaction mixture was cooled to room temperature and desired product (46) was collected by filtration. The filtrate was diluted with EtOAc and washed with water, saturated NaHCO$_3$ and brine.

The organic layer was dried (Na₂SO₄) and concentrated to give additional product (46) (51 mg, 74% combined recovery). MS APCI (−) m/z 382, 384, 386 (M-, Cl, Br pattern) detected. ¹H NMR (400 MHz, CD₃OD) δ 8.86 (s, 1H), 7.85 (s, 1H), 7.53 (s, 2H), 7.32 (d, 1H), 6.82 (t, 1H). ¹⁹F NMR (376 MHz, CD₃OD)−148.3 (s).

7-(4-Bromo-2-chlorophenylamino)-8-fluoroimidazo[1,2-a]pyridine-6-carboxylic acid (46) was alternatively synthesized by the route shown below.

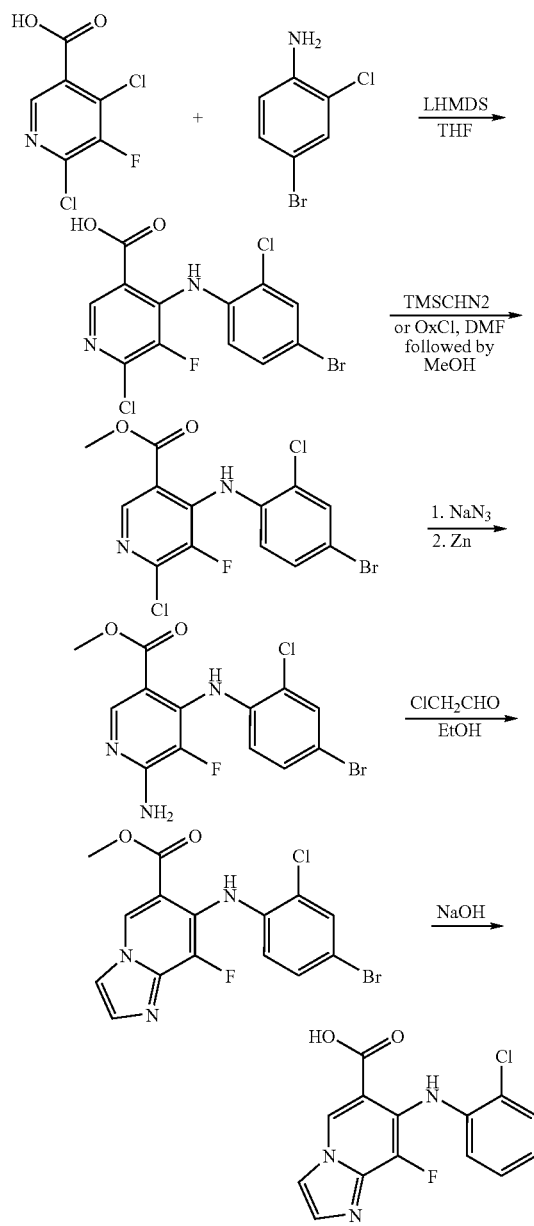

In the first step of this alternative procedure, 4,6-dichloro-5-fluoronicotinic acid (*J. Heterocyclic Chemistry* 1993, 30, 855-859) was used to synthesize 4-(4-bromo-2-chlorophenylamino)-5-bromo-6-chloronicotinic acid according to the alternate procedure described in Example 9, Step B.

Step C: Preparation of 7-(4-bromo-2-chlorophenylamino)-8-fluoroimidazo[1,2-a]pyridine-6-carboxylic acid cyclopropylmethoxyamide (47a): Compound 47 was prepared as described in Step E of Example 19 using 7-(4-bromo-2-chlorophenylamino)-8-fluoroimidazo[1,2-a]pyridine-6-carboxylic acid (46) to give 15 mg (24%) of the desired product (47a) as a white solid. MS APCI (+) m/z 453, 455, 457 (M+, Cl, Br pattern) detected. ¹H NMR (400 MHz, CD₃OD) δ 8.66 (s, 1H), 7.93 (m, 1H), 7.61 (s, 1H), 7.56 (d, 1H), 7.32 (dd, 1H), 6.73 (q, 1H) 3.70 (d, 2H), 1.14 (m, 1H), 0.56 (m, 2H), 0.26 (m, 2H): ¹⁹F (400 MHz, CD₃OD)−139.4 (s).

The following compounds were synthesized in a similar manner as described in Example 20.

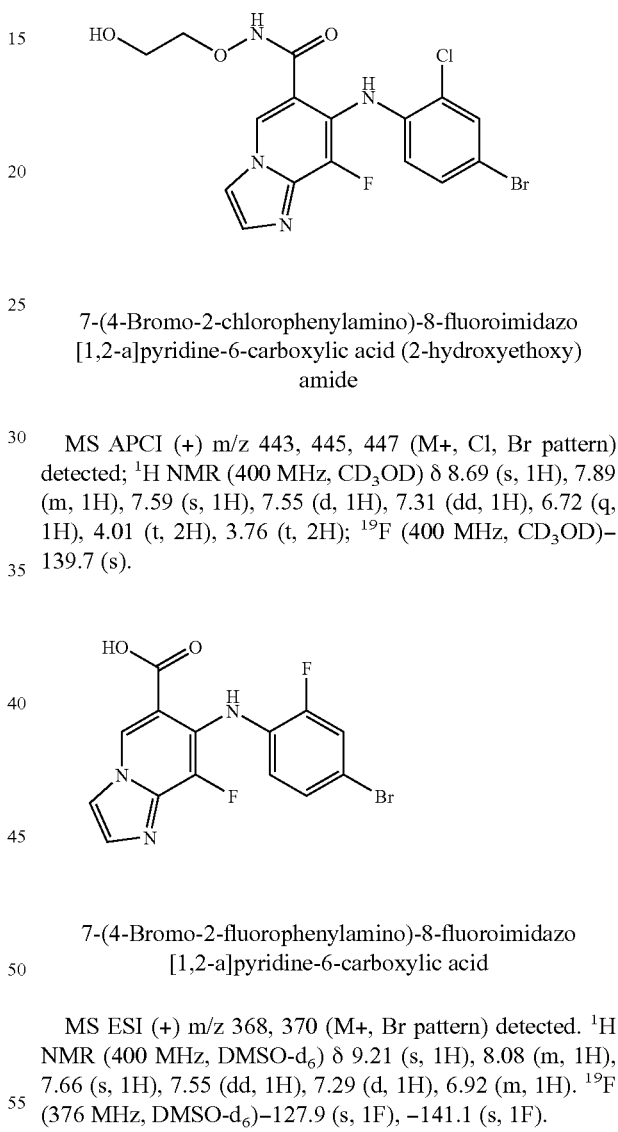

7-(4-Bromo-2-chlorophenylamino)-8-fluoroimidazo[1,2-a]pyridine-6-carboxylic acid (2-hydroxyethoxy) amide MS APCI (+) m/z 443, 445, 447 (M+, Cl, Br pattern) detected; ¹H NMR (400 MHz, CD₃OD) δ 8.69 (s, 1H), 7.89 (m, 1H), 7.59 (s, 1H), 7.55 (d, 1H), 7.31 (dd, 1H), 6.72 (q, 1H), 4.01 (t, 2H), 3.76 (t, 2H); ¹⁹F (400 MHz, CD₃OD)−139.7 (s).

7-(4-Bromo-2-fluorophenylamino)-8-fluoroimidazo[1,2-a]pyridine-6-carboxylic acid MS ESI (+) m/z 368, 370 (M+, Br pattern) detected. ¹H NMR (400 MHz, DMSO-d₆) δ 9.21 (s, 1H), 8.08 (m, 1H), 7.66 (s, 1H), 7.55 (dd, 1H), 7.29 (d, 1H), 6.92 (m, 1H). ¹⁹F (376 MHz, DMSO-d₆)−127.9 (s, 1F), −141.1 (s, 1F).

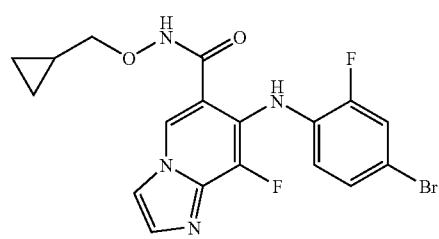

7-(4-Bromo-2-fluorophenylamino)-8-fluoroimidazo[1,2-a]pyridine-6-carboxylic acid cyclopropyl-methoxyamide MS ESI (+) m/z 437, 439 (M+, Br pattern) detected. $^1$H NMR (400 MHz, CD$_3$OD) δ 9.55 (br s, 1H), 8.57 (s, 1H). 7.68 (s, 2H), 7.65 (s, 1H), 7.28 (m, 1H), 7.14 (m, 1H), 6.78 (br s, 1H), 6.63 (m, 1H), 3.72 (m, 2H), 1.07 (m, 1H), 0.59 (m, 2H), 0.28 (m, 2H). $^{19}$F NMR (376 MHz, CD$_3$OD) δ−128.9 (s, 1F), −138.1 (s, 1F).

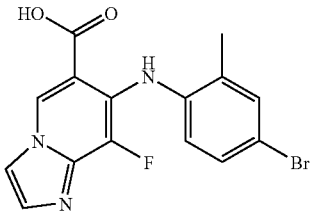

7-(4-Bromo-2-methylphenylamino)-8-fluoroimidazo[1,2-a]pyridine-6-carboxylic acid MS APCI (+) m/z 364, 366 (M+, Br pattern) detected. $^1$H NMR (400 MHz, DMSO-d$_6$) δ 9.22 (s, 1H), 8.07 (m, 1H), 7.68 (s, 1H), 7.42 (d, 1H), 7.28 (dd, 1H), 6.78 (t, 1H), 2.29 (s, 3H). $^{19}$F (376 MHz, DMSO-d$_6$)−142.5 (s).

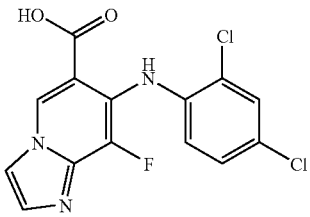

7-(2,4-dichlorophenylamino)-8-fluoroimidazo[1,2-a]pyridine-6-carboxylic acid MS APCI (+) m/z 440, 442 (M+, Cl pattern) detected. $^1$H NMR (400 MHz, DMSO-d$_6$) δ 9.27 (s, 1H), 8.13 (s, 1H), 7.71 (s, 1H), 7.62 (s, 1H), 7.32 (dd, 1H), 6.95 (t, 1H). $^{19}$F (376 MHz, DMSO-d$_6$)−129.9 (s).

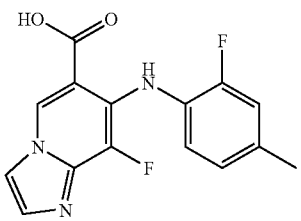

8-Fluoro-7-(2-fluoro-4-methylphenylamino)-imidazo[1,2-a]pyridine-6-carboxylic acid MS APCI (+) m/z 304 (M+1) detected. $^1$H NMR (400 MHz, DMSO-d$_6$) δ 9.48 (br s, 1H), 9.32 (s, 1H), 8.12 (s, 1H), 7.86 (s, 1H), 7.12 (m, 2H), 6.98 (d, 1H), 2.31 (s, 3H). $^{19}$F (376 MHz, DMSO-d$_6$)−128.1 (s, 1F), −148.8 (s, 1F).

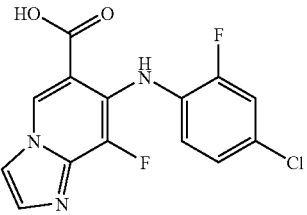

7-(4-Chloro-2-fluorophenylamino)-8-fluoroimidazo[1,2-a]pyridine-6-carboxylic acid MS APCI (+) m/z 324, 326 (M+, Cl pattern) detected. $^1$H NMR (400 MHz, DMSO-d$_6$) δ 9.19 (s, 1H), 8.07 (m, 1H), 7.64 (s, 1H), 7.45 (dd, 1H), 7.17 (d, 1H), 6.98 (m, 1H). $^{19}$F (376 MHz, CD$_3$OD)−128.8 (s, 1F), −154.8 (s, 1F).

Example 21

3-Chloro-7-(2,4-dichlorophenylamino)-8-fluoroimidazo[1,2-a]pyridine-6-carboxylic acid (2-hydroxyethoxy)-amide

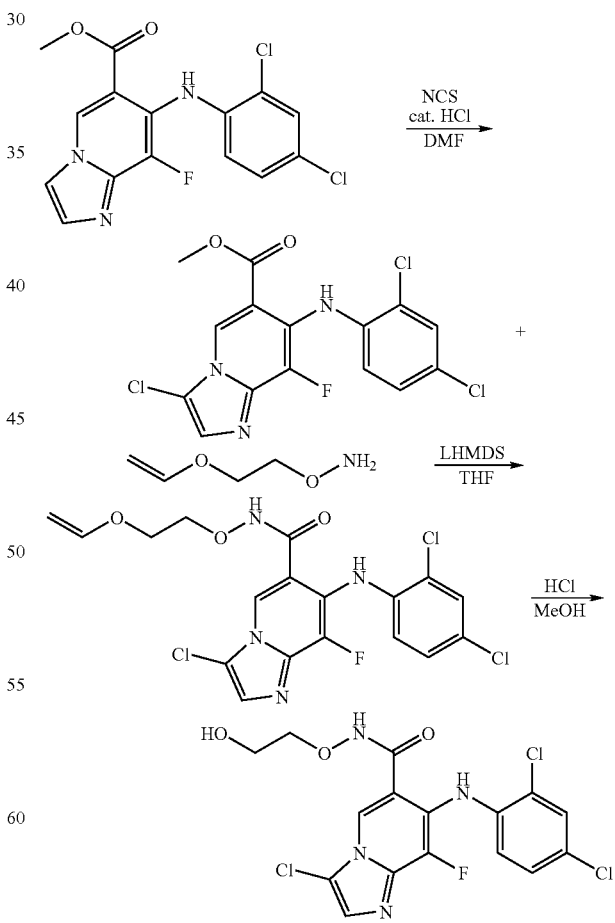

Step A: Preparation of 3-chloro-7-(2,4-dichlorophenylamino)-8-fluoroimidazo[1,2a]pyridine-6-carboxylic acid methyl ester. 7-(2,4-Dichlorophenylamino)-8-fluoroimidazo[1,2-a]pyridine-6-carboxylic acid methyl ester (57.0 mg, 0.16 mmol), which was synthesized in a manner similar to the alternate procedure described in Example 20, Step B, was dissolved into DMF (3 mL). Added N-chlorosuccinimide (17.0 mg, 0.13 mmol) and HCl (1.0 M aqueous solution, 16 μL, 0.016 mmol). After stirring for 16 hours, the suspension was diluted with ethyl acetate, washed with NaHSO$_3$, water (2×), brine, dried over Na$_2$SO$_4$ and concentrated to a yellow solid. Purification by flash column chromatography (4:1 hexanes/ethyl acetate) provided the desired product as a light yellow solid (40 mg, 64%). MS APCI (+) m/z 388, 390 (M+, Cl pattern) detected. $^1$H NMR (400 MHz, CDCl$_3$) δ 8.70 (s, 2H), 7.58 (s, 1H), 7.40 (d, 1H), 7.14 (dd, 1H), 6.77 (t, 1H), 4.02 (s, 3H): $^{19}$F NMR (376 MHz, CDCl$_3$)–135.84 (s).

Step B: Preparation of 3-chloro-7-(2,4-dichlorophenylamino)-8-fluoroimidazo[1,2-a]pyridine-6-carboxylic acid (2-vinyloxyethoxy)-amide. LiHMDS (1.0 M in hexanes, 0.34 mL, 0.34 mmol) was added to a solution 3-chloro-7-(2,4-dichlorophenylamino)-8-fluoroimidazo[1,2-a]pyridine-6-carboxylic acid methyl ester (38 mg, 0.098 mmol) and O-(2-vinylox-ethyl)-hydroxylamine (25 mg, 0.24 mmol) in THF (1.0 mL) cooled to 0° C. The solution was allowed to warm to room temperature and stir for 16 hours. The solution was diluted with ethyl acetate, washed with saturated NaHCO$_3$, water (3×), brine, dried over Na$_2$SO$_4$ and concentrated to a yellow liquid. Purification by flash column chromatography (20:1 to 10:1 dichloromethane/MeOH) provided the desired product as a yellow solid (42 mg, 93%). MS APCI (+) m/z 459, 461 (M+, Cl pattern) detected.

Step C: Preparation of 3-chloro-7-(2,4-dichlorophenylamino)-8-fluoroimidazo[1,2-a]pyridine-6-carboxylic acid (2-hydroxyethoxy)-amide. 3-Chloro-7-(2,4-dichlorophenylamino)-8-fluoro-imidazo[1,2-a]pyridine-6-carboxylic acid (2-vinyloxy-ethoxy)-amide was converted to the desired product according to Example 3, Step B, to provide 31 mg (78%) of desired product as a light yellow solid. MS APCI (+) m/z 433, 435 (M+, Cl pattern) detected. $^1$H NMR (400 MHz, CD$_3$OD) δ 8.52 (s, 1H), 7.57 (s, 1H), 7.42 (d, 1H), 7.16 (dd, 1H), 6.79 (dd, 1H), 4.07 (m, 2H), 3.80 (m, 2H). $^{19}$F NMR (376 MHz, CD$_3$OD) –140.83 (s).

Example 22

7-(4-Ethyl-2-fluorophenylamino)-8-fluoroimidazo[1,2-a]pyridine-6-carboxylic acid ethoxyamide

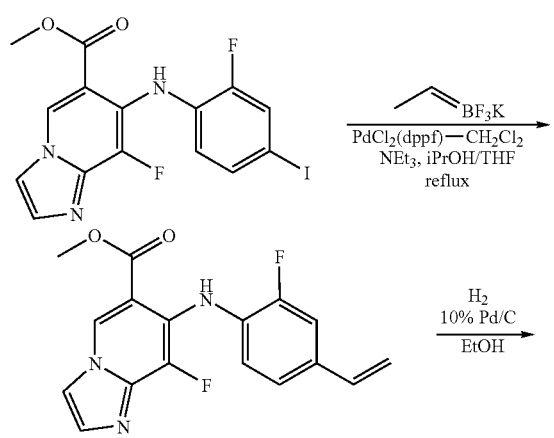

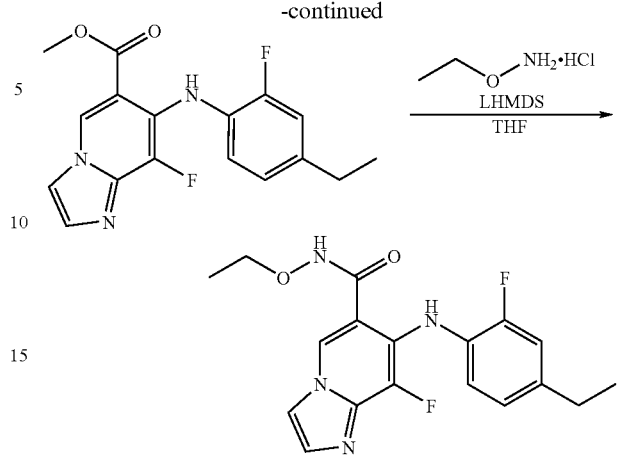

Step A: Preparation of 8-fluoro-7-(2-fluoro-4-vinylphenylamino)-imidazo[1,2-a]pyridine-6-carboxylic acid methyl ester. 8-Fluoro-7-(2-fluoro-4-iodophenylamino)-imidazo[1,2-a]pyridine-6-carboxylic acid methyl ester (250 mg, 0.58 mmol), which was synthesized in a similar manner to the alternative synthesis set forth in Example 20 Step B, was suspended in isopropyl alcohol (6 mL) and tetrahydrofuran (1 mL). Potassium vinyltrifluoroborate (90 mg, 0.67 mmol) and triethylamine (0.165 mL, 1.2 mmol) were added, at which time the reaction mixture became a solution. The reaction mixture was sparged with N$_2$. PdCl$_2$(dppf)-CH$_2$Cl$_2$ (2 mol %, 9 mg) was then added and the reaction was heated to 90° C. and stirred under N$_2$ for 16 hours. The reaction mixture was cooled to room temperature and diluted with water, followed by extraction with ethyl acetate (2×). The combined organic layers were washed with saturated aqueous NaCl, dried over Na$_2$SO$_4$ and concentrated. Purification of the crude product by flash column chromatography (30:1 dichloromethane/methanol) provided the desired product (143 mg, 81%) as a dark yellow solid. MS ESI (+) m/z 330 (M+1) detected.

Step B: Preparation of 7-(4-ethyl-2-fluorophenylamino)-8-fluoroimidazo[1,2-a]pyridine-6-carboxylic acid methyl ester. 8-Fluoro-7-(2-fluoro-4-vinyl-phenylamino)-imidazo[1,2-a]pyridine-6-carboxylic acid methyl ester (165 mg, 0.50 mmol) was suspended in ethanol (5mL), added 10% Pd/C (267 mg, 0.25 mmol) and placed under an atmosphere of H$_2$. The reaction mixture was stirred vigorously at room temperature for 16 hours. The reaction mixture was filtered through CELITE, washed with ethanol and tetrahydrofuran and the filtrate concentrated to a yellow oil. Purification of the crude product by flash column chromatography (gradient of dichloromethane to 20:1 dichloromethane/methanol) provided the desired product (110 mg, 66%) as a dark yellow solid. MS ESI (+) m/z 332 (M+1) detected.

Step C: Preparation of 7-(4-ethyl-2-fluorophenylamino)-8-fluoroimidazo[1,2-a]pyridine-6-carboxylic acid ethoxyamide. 7-(4-Ethyl-2-fluorophenylamino)-8-fluoroimidazo[1,2-a]pyridine-6-carboxylic acid methyl ester (40 mg, 0.12 mmol) was converted to the desired product according to procedure of Step B of Example 21, using O-ethyl-hydroxylamine HCl salt, to provide the desired product as a yellow colored solid (31 mg, 71%). MS ESI (+) m/z 361 (M+1) detected. $^1$H NMR (400 MHz, CD$_3$OD) δ 8.62 (s, 1H), 7.86

(s, 1H), 7.56 (s, 1H), 6.97 (d, 1H), 6.90-6.80 (m, 2H), 3.88 (q, 2H), 2.60 (q, 2H), 1.23 (m, 9H). $^{19}$F (376 MHz, CD$_3$OD)–132.7 (s, 1F), –145.2 (s, 1F).

Example 23

3-Ethyl-8-fluoro-7-(2-fluoro-4-methylphenylamino)-imidazo[1,2-a]pyridine-6-carboxylic acid (2-hydroxyethoxy)-amide

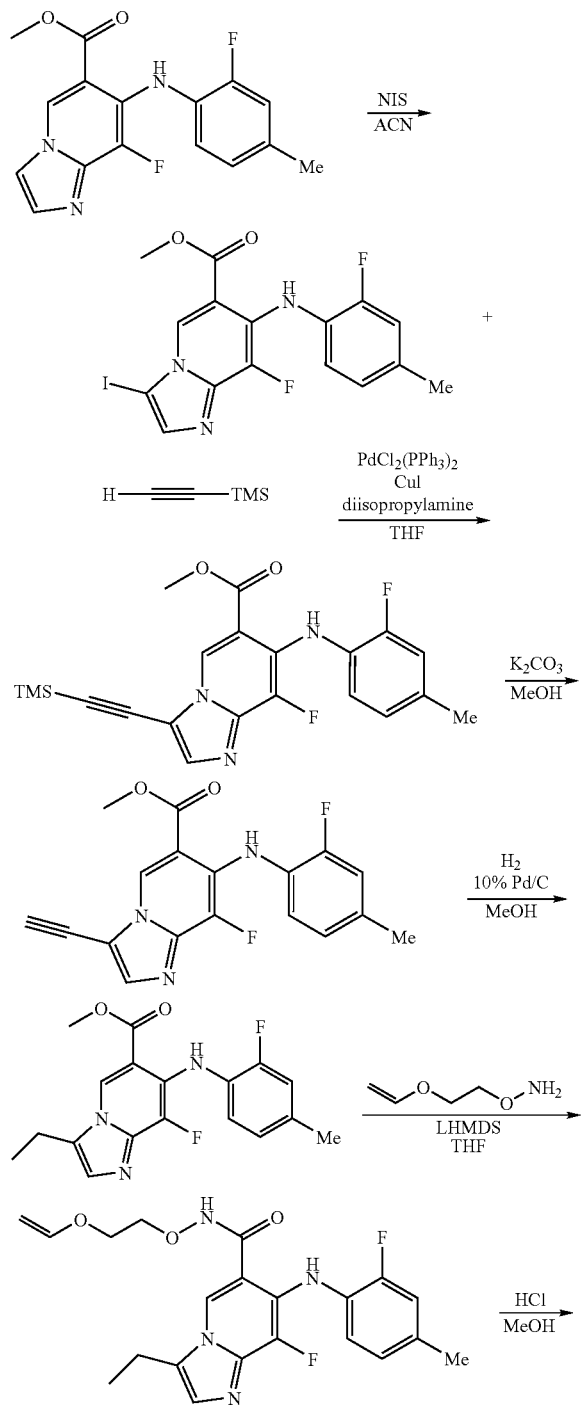

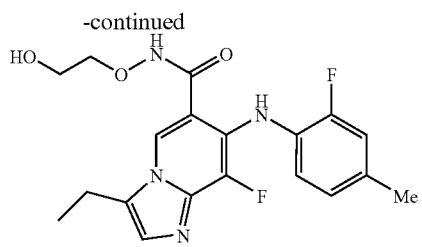

Step A: Preparation of 8-Fluoro-7-(2-fluoro-4-methylphenylamino)-3-iodo-imidazo[1,2-a]pyridine-6-carboxylic acid methyl ester. N-iodosuccinimide (134 mg, 0.60 mmol) was added in a single portion to a solution of 8-fluoro-7-(2-fluoro-4-methylphenylamino)-imidazo[1,2-a]pyridine-6-carboxylic acid methyl ester (172 mg, 0.54 mmol) in acetonitrile (10 mL) resulting in a thick precipitate after ten minutes of stirring. The suspension was diluted with ethyl acetate, washed with NaHSO$_3$, saturated NaHCO$_3$, water, brine, and dried over Na$_2$SO$_4$. Concentration provided the desired product as a yellow solid (241 mg, 100%). MS APCI (+) m/z 444 (M+1) detected. $^1$H NMR (400 MHz, CD$_3$OD) δ 8.78 (s, 1H), 7.62 (s, 1H), 6.95 (m, 3H), 4.00 (s, 3H), 2.33 (s, 3H). $^{19}$F NMR (376 MHz, CD$_3$OD)–131.11 (s, 1F), –146.71 (s, 1F).

Step B: Preparation of 8-fluoro-7-(2-fluoro-4-methylphenylamino)-3-trimethylsilanylethynyl-imidazo[1,2-a]pyridine-6-carboxylic acid methyl ester. THF (1.0 mL), diisopropylamine (95 µL, 0.68 mmol) and trimethylsilylacetylene (38 µL, 0.27 mmol) were added to a mixture of 8-fluoro-7-(2-fluoro-4-methylphenylamino)-3-iodo-imidazo[1,2-a]pyridine-6-carboxylic acid methyl ester (100 mg, 0.23 mmol), CuI (4.0 mg, 0.023 mmol) and PdCl$_2$(PPh$_3$)$_2$ (16 mg, 0.023 mmol). The solution was stirred at room temperature for 16 hours. The reaction was diluted with ethyl acetate, washed with saturated NaHCO$_3$ (3×), brine (2×), dried over Na$_2$SO$_4$ and concentrated to a dark brown solid. Flash column chromatography (40:1 dichloromethane/MeOH) provide desired product (30 mg, 32%) as a yellow liquid. MS APCI (+) m/z 414 (M+1) detected. $^1$H NMR (400 MHz, CDCl$_3$) δ 8.77 (s, 1H), 8.61 (s, 1H), 7.80 (s, 1H), 6.90 (m, 3H), 4.00 (s, 3H), 2.32 (s, 3H), 0.33 (s, 9H). $^{19}$F NMR (376 MHz, CDCl$_3$)–129.12 (s, 1F), –141.99 (s, 1F).

Step C: Preparation of 3-ethynyl-8-fluoro-7-(2-fluoro-4-methylphenylamino)-imidazo[1,2-a]pyridine-6-carboxylic acid methyl ester. Potassium carbonate (70 mg, 0.51 mmol) was added to a solution of 8-fluoro-7-(2-fluoro-4-methylphenylamino)-3-trimethylsilanylethynylimidazo[1,2-a]pyridine-6-carboxylic acid methyl ester in MeOH (5 mL) and stirred at room temperature for two hours. The mixture was diluted with ethyl acetate, washed with brine (2×), dried over Na$_2$SO$_4$ and concentrated to a brown residue. Flash column chromatography (dichloromethane to 80:1 dichloromethane/MeOH) provided the desired product (16 mg, 65%) as a yellow liquid. MS APCI (+) m/z 342 (M+1) detected.

Step D: Preparation of 3-ethyl-8-fluoro-7-(2-fluoro-4-methylphenylamino)-imidazo[1,2-a]pyridine-6-carboxylic acid methyl ester. A mixture of 3-ethynyl-8-fluoro-7-(2-fluoro-4-methylphenylamino)-imidazo[1,2-a]pyridine-6-carboxylic acid methyl ester (16 mg, 0.047 mmol) and 10% Pd/C (5 mg) under an atmosphere of hydrogen (balloon) was stirred vigorously for one hour. The mixture was filtered through a plug of rinsing with dichloromethane and concentrated to provide the desired product (14 mg, 86%) as a yellow foam. MS APCI (+) m/z 346 (M+1) detected. $^1$H NMR (400 MHz, CDCl$_3$) δ

8.51 (s, 1H), 8.31 (s, 1H), 7.38 (s, 1H), 6.91 (d, 1H), 6.84 (s, 2H), 3.97 (s, 3H), 2.86 (q, 2H), 2.30 (s, 3H), 1.43 (t, 3H).

Step E: Preparation of 3-ethyl-8-fluoro-7-(2-fluoro-4-methylphenylamino)-imidazo[1,2-a]pyridine-6-carboxylic acid (2-hydroxy-ethoxy)-amide. 3-Ethyl-8-fluoro-7-(2-fluoro-4-methyl-phenylamino)-imidazo[1,2-a]pyridine-6-carboxylic acid methyl ester (14 mg, 0.041 mmol) was converted to the desired product according to the Step A of example 21 and Step B of Example 3, Step B to provide the desired product (hydrochloride salt) as a tan colored solid (9 mg, 51% over two steps). MS APCI (+) m/z 391 (M+1) detected. ¹H NMR (400 MHz, CD₃OD) δ 8.63 (s, 1H), 7.65 (s, 1H), 7.16 (m, 1H), 7.01 (m, 2H), 4.04 (br s, 2H), 3.79 (br s, 2H), 2.97 (q, 2H), 2.35 (2, 3H), 1.45 (t, 3H). ¹⁹F NMR (376 MHz, CD₃OD)– 127.69 (s, 1F), –155.07 (s, I F).

Example 24

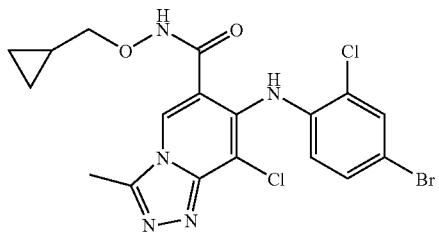

Synthesis of 7-(4-bromo-2-chlorophenylamino)-8-chloro-3-methyl-[1,2,4]-triazolo-[4,3-a]pyridine-6-carboxylic acid cyclopropylmethoxyamide (53a)

Step A: Preparation of 4-(4-bromo-2-chlorophenylamino)-5-chloro-6-hydrazinonicotinic acid ethyl ester (49): 4-(4-Bromo-2-chlorophenylamino)-5,6-dichloronicotinic acid ethyl ester (48) was prepared by standard methods from 4-(4-bromo-2-chlorophenylamino)-5,6-dichloronicotinic acid. Hydrazine monohydrate (0.59 mL, 12.16 mmol) was added to a solution of 4-(4-bromo-2-chlorophenylamino)-5,6-dichloronicotinic acid ethyl ester (48) (1.72 g, 4.05 mmol) in N,N-dimethylacetamide (20 mL). After stirring at 90° C. for 1 hour, the reaction mixture was cooled to room temperature and diluted with EtOAc. The organic layer was washed with water and brine, dried (Na₂SO₄) and concentrated. Purification by flash column chromatography using the Biotage system (20:1 CH₂Cl₂:EtOAc) provided the desired product (49) (307 mg, 18%).

Step B: Preparation of 7-(4-bromo-2-chlorophenylamino)-8-chloro-3-methyl-[1,2,4]triazolo[4,3-a]pyridine-6-carboxylic acid ethyl ester (51a): Acetic anhydride (22 μL, 0.238 mmol) was added to a solution of 4-(4-bromo-2-chlorophenylamino)-5-chloro-6-hydrazinonicotinic acid ethyl ester (49) (0.100 g, 0.238 mmol) and triethylamine (66 μL, 0.476 mmol) in CH₂Cl₂ (2.5 mL) at 0° C., and then the solution was warmed to room temperature to provide compound 50a (not isolated). After 10 minutes, POCl₃ (87 μL, 0.952 mmol) was added dropwise and the reaction mixture was warmed to room temperature. After 16 hours, the reaction mixture was heated to reflux and stirred for 3 days. The reaction mixture was cooled to room temperature and concentrated. The residue was diluted with EtOAc and saturated NaHCO₃ was added and the mixture stirred for 20 minutes. The layers were separated and the organic layer was washed with brine. The aqueous washings were back extracted with EtOAc. The combined organic extracts were dried (Na₂SO₄) and concentrated. Purification by flash column chromatography using the Biotage system (9:1 CH₂Cl₂/EtOAc) provided compound 51a (80 mg, 75%).

Step C: Preparation of 7-(4-bromo-2-chlorophenylamino)-8-chloro-3-methyl-[1,2,4]triazolo[4,3-a]pyridine-6-carboxylic acid (52a): Sodium hydroxide (715 μL of a 1 M solution) was added to a solution of 7-(4-bromo-2-chlorophenylamino)-8-chloro-3-methyl-[1,2,4]triazolo[4,3-a]pyridine-6-carboxylic acid ethyl ester (51a) (79 mg, 179 mmol) in 3:1 THF:water (4.5 mL). After 16 hours, the reaction mixture was poured into a separatory funnel, diluted with brine and acidified with 1 M HCl to about pH 2. The aqueous layer was extracted with 1:1 EtOAc/THF. The combined organic extracts were dried (Na₂SO₄) and concentrated and the residue (52a) was carried forward without further purification.

Step D: Preparation of 7-(4-bromo-2-chlorophenylamino)-8-chloro-3-methyl-[1,2,4]triazolo[4,3-a]pyridine-6-carboxylic acid cyclopropylmethoxyamide (53a): Compound 53a was prepared as described in Example 2 using 7-(4-bromo-2-chlorophenylamino)-8-chloro-3-methyl-[1,2,4]triazolo[4,3-a]pyridine-6-carboxylic acid (52a) to give 2 mg (5%) of the desired product. MS APCI (–) m/z 482, 484, 486 (M-, Cl, Br pattern) detected.

Example 25

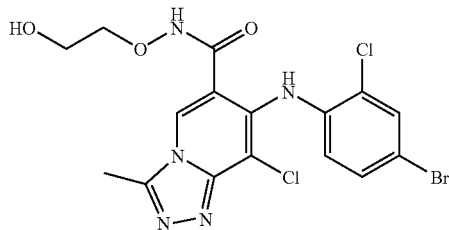

Synthesis of 7-(4-bromo-2-chlorophenylamino)-8-chloro-3-methyl-[1,2,4]triazolo[4,3-a]pyridine-6-carboxylic acid (2-hydroxyethoxy)-amide (54a)

Compound 54a was prepared as described herein starting with 7-(4-bromo-2-chlorophenylamino)-8-chloro-3-methyl-[1,2,4]triazolo[4,3-a]pyridine-6-carboxylic acid (52a) to give 1 mg (2% for the two steps) desired product (54a). MS APCI (–) m/z 472, 474, 476 (M-, Cl, Br pattern) detected.

Example 26

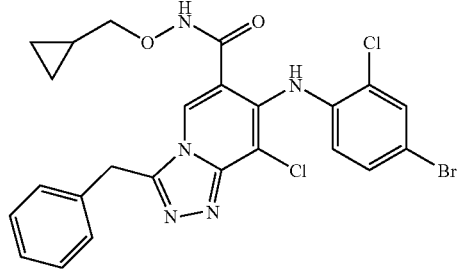

Synthesis of 3-benzyl-7-(4-bromo-2-chlorophenylamino)-8-chloro-[1,2,4]triazolo[4,3-a]pyridine-6-carboxylic acid cyclopropylmethoxyamide (53b)

Step A: Preparation of 3-benzyl-7-(4-bromo-2-chlorophenylamino)-8-chloro-[1,2,4]triazolo[4,3-a]pyridine-6-carboxylic acid methyl ester (51b): Phenylacetyl chloride (152 μL, 1.148 mmol) was added to a solution of 4-(4-bromo-2-chlorophenylamino)-5-chloro-6-hydrazinonicotinic acid methyl ester (49) (0.233 g, 0.574 mmol) and triethylamine (160 μL, 1.148 mmol) in $CH_2Cl_2$ (5.7 mL) at 0° C. After warming to room temperature, an additional 75 μL phenylacetyl chloride was added. After 6 hours, the reaction mixture was concentrated and diluted with EtOAc. The organic layer was washed with water and brine, dried ($Na_2SO_4$) and concentrated. The residue (50b) was diluted with dichloroethylene (2 mL) and $POCl_3$ (465 μL, 5.082 mmol) was added. After stirring at reflux for 12 hours, the reaction mixture was cooled to room temperature and concentrated. The residue was diluted with EtOAc and saturated $NaHCO_3$ was added and the mixture stirred for 20 minutes. The resulting solid was collected by filtrate to give the desired product (51b) (97 mg, 30%).

Step B: Preparation of 3-benzyl-7-(4-bromo-2-chlorophenylamino)-8-chloro-[1,2,4]triazolo[4,3-a]pyridine-6-carboxylic acid cyclopropylmethoxyamide (53b): Compound 53b was prepared as described in Step C of Example 24 and Example 2 using 3-benzyl-7-(4-bromo-2-chlorophenylamino)-8-chloro-[1,2,4]triazolo[4,3-a]pyridine-6-carboxylic acid methyl ester (5 lb) as the starting material to give 5 mg (4% for the two steps) of the desired product (53b). MS APCI (−) m/z 558, 560, 562 (M-, Cl, Br pattern) detected.

$^1H$ NMR (400 MHz, $CDCl_3$) δ 8.22 (s, 1H), 7.30 (m, 6H), 6.50 (d, 1H), 4.53 (s, 2H), 3.49 (m, 2H), 0.94 (m, 1H), 0.51 (m, 2H), 0.19 (m, 2H).

Example 27

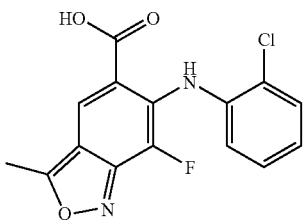

Synthesis of 6-(2-chlorophenylamino)-7-fluoro-3-methylbenzo [c]isoxazole-5-carboxylic acid (56)

Step A: Preparation of 6-(2-chlorophenylamino)-7-fluoro-3-methyl-benzo[c]-isoxazole-5-carboxylic acid methyl ester (55): Sodium azide (128 mg, 1.95 mmol) was added to a mixture of 5-acetyl-2-(2-chlorophenylamino)-3,4-difluorobenzoic acid methyl ester (6) (601 mg, 1.59 mmol) in 3:1 acetone:water (16 ml) and heated to reflux. After 16 hours, the reaction mixture was cooled to room temperature, and diluted with EtOAc and water. The organic layer was washed with water, dried ($MgSO_4$) and concentrated. The resulting residue was diluted with water (8 mL) and heated to reflux. After 5 hours, the mixture was cooled to room temperature and diluted with EtOAc. The organic layer was washed with water, dried ($MgSO_4$) and concentrated. Purification by flash column chromatography using the Biotage system (20% EtOAc in hexanes) provided the desired product (55) (410 mg, 77%).

Step B: Preparation of 6-(2-chlorophenylamino)-7-fluoro-3-methylbenzo [c]-isoxazole-5-carboxylic acid (56): To a solution of 6-(2-chlorophenylamino)-7-fluoro-3-methylbenzo[c]-isoxazole-5-carboxylic acid methyl ester (55) (100 mg, 0.299 mmol) in 6:1 THF:water (3.5 mL) was added LiOH (0.60 ml of a 1 M solution in water). After 1 hour, the reaction was acidified to pH 1 with 1 N HCl, diluted with water and extracted with EtOAc. The combined organic extracts were washed with water, dried ($MgSO_4$) and concentrated to give the desired product (56) (87 mg, 91%). MS APCI (−) m/z 319, 321 (M+, Cl pattern) detected. $^1H$ NMR (400 MHz, $CD_3OD$) δ 8.45 (s, 1H), 7.38 (dd, 1H), 7.20 (m, 1H), 6.91 (m, 2H), 2.88 (s, 3H); $^{19}F$ NMR (376 MHz, $CD_3OD$)−136.40 (s).

Example 28

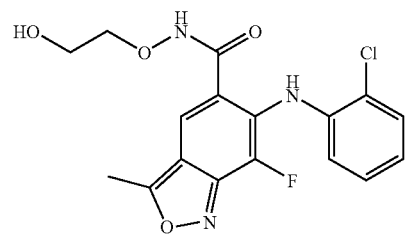

Synthesis of 6-(2-chlorophenylamino)-7-fluoro-3-methylbenzo [c]isoxazole-5-carboxylic acid (2-hydroxyethoxy)amide (57a)

Compound 57a was prepared as described in Example 27 using 6-(2-chlorophenylamino)-7-fluoro-3-methylbenzo[c]isoxazole-5-carboxylic acid (56) to give 35 mg (44%) desired product. MS APCI (−) m/z 388, 390 (M+, Cl pattern) detected; $^1H$ NMR MHz, $CD_3OD$) δ 7.73 (s, 1H), 7.36 (d, 1H), 7.17 (t, 1H), 6.89 (t, 1H), 6.81 (dd, 1H), 3.72 (d, 2H), 2.87 (s, 3H), 1.15 (m, 1H), 0.54 (d, 2H), 0.26 (d, 2H); $^{19}F$ NMR (376 MHz, $CD_3OD$)−135.08 (s).

Example 29

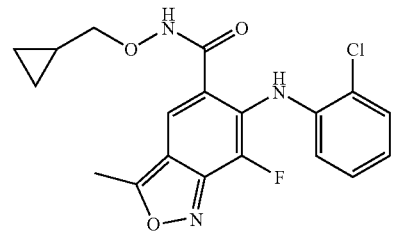

Synthesis of 6-(2-chloro-phenylamino)-7-fluoro-3-methylbenzo[c]isoxazole-5-carboxylic acid cyclopropylmethoxy-amide (57b)

Compound 57b was prepared as described in Example 27 using 6-(2-chlorophenylamino)-7-fluoro-3-methylbenzo[c]isoxazole-5-carboxylic acid (56) to give 35 mg (44%) desired product. MS APCI (−) m/z 388, 390 (M+, Cl pattern) detected; $^1H$ NMR MHz, CD$_3$OD) δ 7.73 (s, 1H), 7.36 (d, 1H), 7.17 (t, 1H), 6.89 (t, 1H), 6.81 (dd, 1H), 3.72(d, 2H), 2.87 (s, 3H), 1.15 (m, 1H), 0.54 (d, 2H), 0.26 (d, 2H); $^{19}$F NMR (376 MHz, CD$_3$OD)−135.08 (s).

Example 30

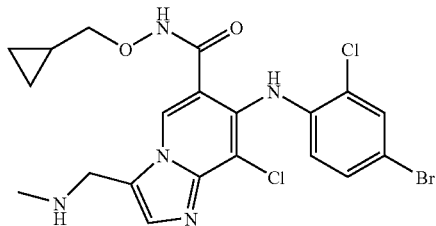

Synthesis of 7-(4-bromo-2-chlorophenylamino)-8-chloro-3-methylaminomethyl-imidazo[1,2-a]pyridine-6-carboxylic acid cyclopropylmethoxyamide (63)

Step A: Preparation of 7-(4-bromo-2-chlorophenylamino)-8-chloro-3-formylimidazo[1,2-a]pyridine-6-carboxylic acid methyl ester (58): A suspension of 6-amino-4-(4-bromo-2-chlorophenylamino)-5-chloro-nicotinic acid methyl ester (28) (1.06 g, 2.72 mmol) and 2-chloro-malonaldehyde (587 mg, 5.43 mmol) was heated to 80° C. for 45 minutes. The solution was allowed to cool to room temperature, and then washed with saturated aqueous NaHCO$_3$, and brine. The organic layer was dried over NaSO$_4$, filtered, concentrated in vacuo, and purified by column chromatography (20:1 methylene chloride/methanol) to give the desired product as a dark yellow solid. The solid was triturated with ethyl acetate and isolated by filtration to provide the desired product as a yellow solid (0.436 g, 36%). MS (APCI+) m/z 442, 444, 446 (M+; Cl, Br pattern) detected.

Step B: Preparation of 7-(4-bromo-2-chlorophenylamino)-8-chloro-3-methylaminomethylimidazo[1,2-a]pyridine-6-carboxylic acid methyl ester (59): A suspension of 7-(4-bromo-2-chlorophenylamino)-8-chloro-3-formylimidazo[1,2-a]pyridine-6-carboxylic acid methyl ester (58) (25 mg, 0.056 mmol), acetic acid (7 μL, 0.11 mmol), and methylamine (2.0 M solution in THF, 56 μL, 0.11 mmol) was stirred for 0.5 hours. Sodium triacetoxyborohydride (36 mg, 0.17 mmol) was added and the solution allowed to stir overnight. The reaction mixture was concentrated to dryness and purified by flash column chromatography (dichloromethane followed by 10:1 dichloromethane/methanol) to provide the desired product as a yellow solid (12 mg, 46%). MS (APCI+) m/z 455, 457, 459 (M+; Cl, Br pattern) detected.

Step C: Preparation of 7-(4-bromo-2-chlorophenylamino)-3-[(tert-butoxycarbonylmethylamino)-methyl]-8-chloroimidazo[1,2-a]pyridine-6-carboxylic acid methyl ester (60): Di-tert-butyl dicarbonate (6 mg, 0.029 mmol) and triethylamine (4 μL, 0.029 mmol) were added to a solution of 7-(4-bromo-2-chlorophenylamino)-8-chloro-3-methyaminomethylimidazo[1,2-a]pyridine-6-carboxylic acid methyl ester (59) (12 mg, 0.026 mmol) in dichloromethane. The solution was stirred at room temperature for 0.5 hr after which time HPLC analysis indicated the reaction had gone to completion. The solution was rotovapped to dryness to provide the desired product as a yellow foam (15 mg, quantitative). MS (APCI+) m/z 557, 559, 561 (M+; Cl, Br pattern) detected.

Step D: Preparation of 7-(4-bromo-2-chlorophenylamino)-3-[(tert-butoxycarbonylmethylamino)-methyl]-8-chloroimidazo[1,2-a]pyridine-6-carboxylic acid (61): Sodium hydroxide (1.0 M aqueous solution, 0.16 mL, 0.16 mmol) was added to a solution of 7-(4-bromo-2-chlorophenylamino)-3-[(tert-butoxycarbonylmethylamino)-methyl]-8-chloroimidazo[1,2-a]pyridine-6-carboxylic acid methyl ester (60) (15 mg, 0.026 mmol) in 4:1 MeOH/water (5 mL). When the reaction was complete, the solution was diluted with water, acidified to pH 3 by addition of 1.0 M aqueous HCl, and extracted with ethyl acetate. The organic extracts were dried over NaSO$_4$, filtered, concentrated in vacuo to provide the desired product as a white crystalline solid (12 mg, 84%). MS (APCI−) m/z 541, 543, 545 (M−; Cl, Br pattern) detected.

Step E: Preparation of [7-(4-bromo-2-chlorophenylamino)-8-chloro-6-cyclopropylmethoxycarbamoylimidazo[1,2-a]pyridin-3-ylmethyl]-methylcarbamic acid tert-butyl ester (62): EDCI (6 mg, 0.033 mmol) and HOBt (5 mg, 0.033 mmol) were added to a solution of 7-(4-bromo-2-chlorophenylamino)-3-[(tert-butoxycarbonylmethylamino)-methyl]-8-chloroimidazo[1,2-a]pyridine-6-carboxylic acid (61) in dimethylacetamide (0.4 mL). The yellow solution was allowed to stir at room temperature for 0.5 hours after which time O-cyclopropylmethyl-hydroxylamine (6 mg, 0.066 mmol) and triethylamine (6 μL, 0.044 mmol) were added and the solution allowed to stir overnight. The reaction mixture was diluted with ethyl acetate, washed with water, saturated aqueous ammonium chloride, saturated aqueous potassium carbonate and brine. The organic phase was dried over NaSO$_4$, filtered, concentrated in vacuo to provide the desired product as a yellow residue (11.5 mg, 85%). MS (APCI+) m/z 612, 614, 616 (M+; Cl, Br pattern) detected.

Step F: Preparation of 7-(4-bromo-2-chlorophenylamino)-8-chloro-3-methylaminomethylimidazo[1,2-a]pyridine-6-carboxylic acid cyclopropylmethoxyamide (63): A solution of [7-(4-bromo-2-chlorophenylamino)-8-chloro-6-cyclopropylmethoxy-carbamoyl-imidazo[1,2-a]pyridin-3-ylmethyl]-methyl-carbamic acid tert-butyl ester (62) in 1:1 dichloromethane/trifluoroacetic acid was stirred for two hours. Solvent was removed under reduced pressure and the residue redissolved into ethyl acetate. The organic solution was washed with saturated aqueous potassium carbonate and brine. The aqueous washes were back-extracted with ethyl acetate. The combined organic extracts are dried over NaSO$_4$, filtered, and concentrated in vacuo to provide the desired product as a yellow solid (8 mg, 83%). MS (APCI+) m/z 512, 514, 516 (M+; Cl, Br pattern) detected. $^1$H NMR (400 MHz, methanol-d$_4$) δ 8.72 (s, 1H), 7.58 (s, 1H), 7.54 (s, 1H), 7.25 (d, 1H), 6.55 (d, 1H), 4.23 (s, 2H), 3.67 (d, 2H), 2.51 (s, 3H), 1.13 (m, 1H), 0.50 (d, 2H), 0.24 (d, 2H).

Example 31

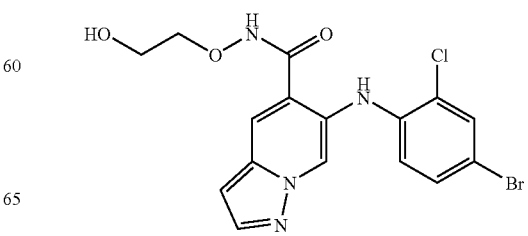

6-(4-bromo-2-chlorophenylamino)-pyrazolo[1,5-a]pyridine-5-carboxylic acid (2-hydroxyethoxy)amide (73a)

Compound 73a, where W=Br, Y=Cl, and X=H, can be prepared as shown in FIG. 12.

Example 32

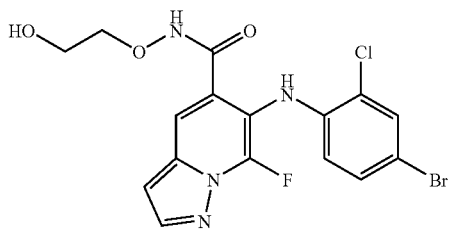

Synthesis of 6-(4-bromo-2-chlorophenylamino)-7-fluoropyrazolo[1,5-a]pyridine-5-carboxylic acid (2-hydroxyethoxy)-amide (73b)

Compound 73b, where W=Br, Y=Cl, and X=F, can be prepared as shown in FIG. 12.

Example 33

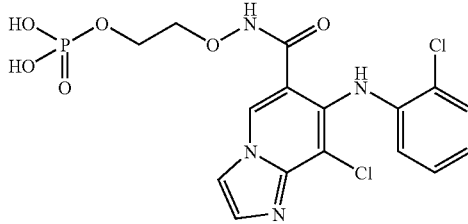

Synthesis of phosphoric acid mono-(2-{[7-(4-bromo-2-chlorophenylamino)-8-chloro-imidazo[1,2-a]pyridine-6-carbonyl]-aminooxy}-ethyl) ester (74)

7-(4-bromo-2-chlorophenylamino)-8-chloroimidazo[1,2-a]pyridine-6-carboxylic acid (2-hydroxyethoxy)-amide (33a) (100 mg, 0.234 mmol), tetrazole (23 mg, 0.327 mmol) and di-tert-butyl diisopropylphosphoramidite (0.096 mL, 0.304 mmol) were dissolved/suspended in 30 mL of anhydrous DMF under an atmosphere of dry N$_2$. The reaction mixture was stirred for about 3 hours, after which time the reaction was cooled to −78° C. and tert-butyl hydrogen peroxide (0.100 mL of 70% solution in water) was added. The cooling bath was then taken away and the reaction was slowly warmed up to room temperature and reacted over night. The reaction mixture was then partitioned between a solution of ethyl ether/ethyl acetate (5:1) and saturated aqueous NaHCO$_3$. The organic layer was saved and successively washed with 10% aqueous sodium sulfite, 3 times with water and finally with brine. The resulting organic layer was dried over MgSO$_4$, filtered and concentrated under vacuum. The residue was dissolved in 3 mL of a solution of TFA/DCM (2:1) under an atmosphere of dry N$_2$. The reaction was stirred at room temperature for about 2 hours after which time it was concentrated under vacuum and the resulting residue was stirred in methanol for about 1 hour. The off-white solid was collected via suction filtration, washed with methanol followed by ethyl ether and then air-dried to give the desired compound (74).

Example 34

7-(4-Bromo-2-chlorophenylamino)-8-methylimidazo[1,2-a]pyridine-6-carboxylic acid

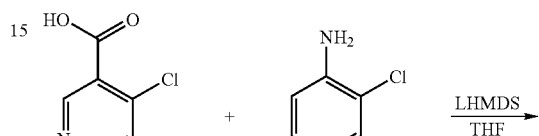

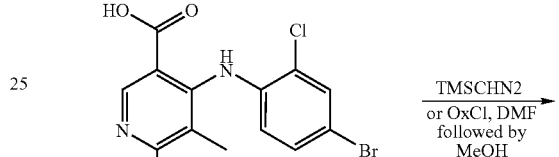

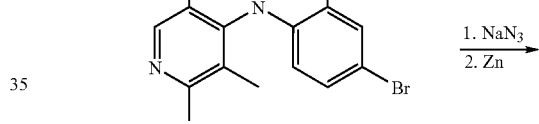

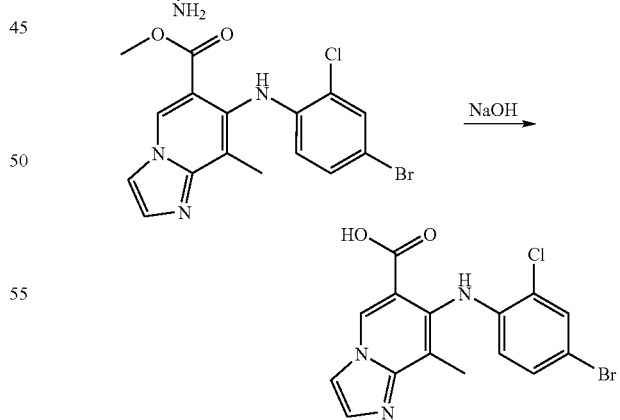

4,6-Dichloro-5-methylnicotinic acid (*J. Heterocyclic Chemistry* 1999, 36, 953-957) was converted to 7-(4-bromo-2-chloro-phenylamino)-8-methylimidazo[1,2-a]pyridine-6-carboxylic acid according to the steps described in the alternate synthesis of Step D, Example 9. It was determined that addition of sodium azide to the 4-(4-bromo-2-chloro-phenylamino)-6-chloro-5-methylnicotinic acid methyl ester intermediate required heating to 50° C., which results in a separable mixture of the desired methyl ester, 6-azido-4-(4-bromo-2-chlorophenylamino)-5-methylnicotinic acid methyl ester, and the corresponding carboxylic acid. MS ESI (+) m/z 380, 382 (M+, Cl, Br pattern) detected. $^1$H NMR (400 MHz, DMSO-$d_6$) δ 9.46 (s, 1H), 9.40 (br s, 1H), 8.25 (d, 1H), 8.12 (d, 1H), 7.79 (m, 1H), 7.42 (dd, 1H), 6.80 (d, 1H), 2.07 (s, 3H).

The following compound was prepared as described in the above example using 4-bromo-2-fluorophenylamine in the first step:

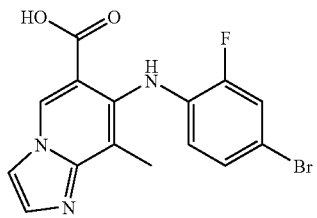

7-(4-Bromo-2-fluorophenylamino)-8-methylimidazo[1,2-a]pyridine-6-carboxylic acid MS ESI (+) m/z 364, 366 (M+, Cl, Br pattern) detected. $^1$H NMR (400 MHz, DMSO-$d_6$) δ 9.40 (s, 1H), 9.26 (br s, 1H), 8.22 (d, 1H), 8.10 (d, 1H), 7.61 (dd, 1H), 7.29 (dd, 1H), 6.87 (t, 1H), 2.14 (s, 3H). $^{19}$F (376 MHz, DMSO-$d_6$)−125.7 (s).

Example 35

Preparation of [6-(5-Amino-[1,3,4]oxadiazol-2-yl)-8-chloro-imidazo [1,2-a]pyridin-7-yl]-(4-bromo-2-fluorophenyl)-amine

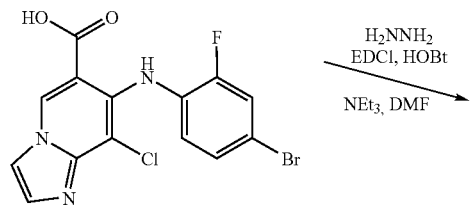

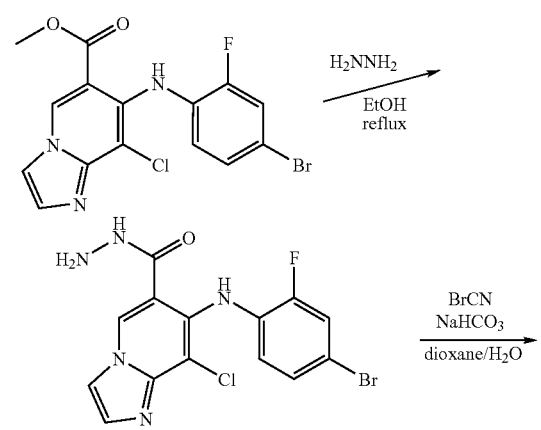

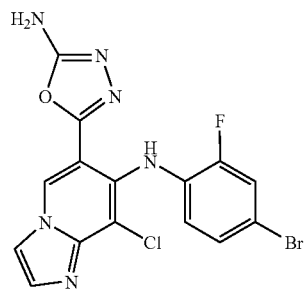

Step A: Preparation of 7-(4-bromo-2-fluorophenylamino)-8-chloroimidazo[1,2-a]pyridine-6-carboxylic acid hydrazide. 7-(4-Bromo-2-fluoro-phenylamino)-8-chloro-imidazo[1,2-a]pyridine-6-carboxylic acid was converted to the hydrazide according to the coupling conditions described in Step A of Example 3. Alternatively, the hydrazide can be prepared directly from 7-(4-Bromo-2-fluorophenylamino)-8-chloroimidazo[1,2-a]pyridine-6-carboxylic acid methyl ester by refluxing with hydrazine in ethanol. MS ESI (+) m/z 398, 400 (M+, Cl, Br pattern) detected.

Step B: Preparation of [6-(5-amino-[1,3,4]oxadiazol-2-yl)-8-chloroimidazo[1,2-a]pyridin-7-yl]-(4-bromo-2-fluorophenyl)-amine. 7-(4-Bromo-2-fluoro-phenylamino)-8-chloro-imidazo[1,2-a]pyridine-6-carboxylic acid hydrazide (100 mg, 0.25 mmol) was suspended in dioxane (2 mL). Cyanogen bromide (27 mg, 0.253 mmol) was added, followed by a solution of sodium bicarbonate (21 mg, 0.25 mmol) in H$_2$O (1.2 mL). The reaction mixture was stirred at room temperature for 16 hours. The reaction mixture was diluted with ethyl acetate and washed with water and saturated aqueous NaCl, dried over Na$_2$SO$_4$ and concentrated to yield the desired product (97 mg, 91%) as a white solid. MS ESI (+) m/z 423, 425 (M+, Cl, Br pattern) detected. $^1$H NMR (400 MHz, CD$_3$OD) δ 8.98 (s, 1H), 7.95 (s, 1H), 7.61 (s, 1H), 7.33 (d, 1H), 7.17 (d, 1H), 6.78 (t, 1H). $^{19}$F (376 MHz, CD$_3$OD)−128.6 (t).

Example 36

Preparation of 5-[7-(4-Bromo-2-fluorophenylamino)-8-chloroimidazo[1,2-a]pyridin-6-yl]-[1,3,4]oxadiazole-2-thiol

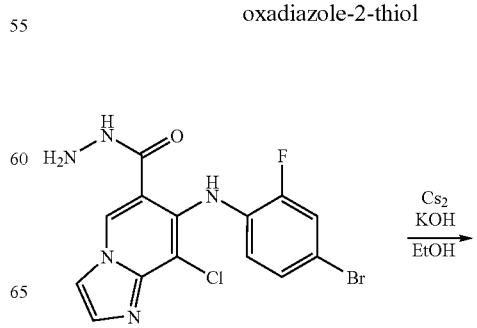

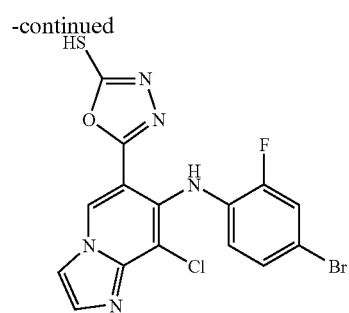

7-(4-Bromo-2-fluoro-phenylamino)-8-chloro-imidazo[1,2-a]pyridine-6-carboxylic acid hydrazide (50 mg, 0.13 mmol) was suspended in ethanol (2.5 mL) and cooled to 0° C. Carbon disulfide (22 mg, 0.29 mmol) was added, followed by powdered potassium hydroxide (7 mg, 0.13 mmol). The reaction mixture was stirred under $N_2$ for 1 hour at 0° C. and then for 30 minutes at room temperature. The reaction mixture was then brought to reflux and stirred under $N_2$ for 5 days. The reaction mixture was diluted with water and acidified to pH 1-2 with aqueous 1 M HCl. This mixture was then extracted with ethyl acetate (2×). The combined organic layers were washed with saturated aqueous $NaHCO_3$, saturated aqueous NaCl, dried over $Na_2SO_4$ and concentrated. Purification of the crude product was achieved by flash column chromatography (gradient of dichloromethane to 15:1 dichloromethane/methanol) and then trituration with diethyl ether and dichloromethane to yield the desired product (17 mg, 31%) as a yellow solid. MS ESI (+) m/z 440, 442 (M+, Cl, Br pattern) detected. $^1$H NMR (400 MHz, DMSO-$d_6$) δ 9.29 (s, 1H), 8.16 (s, 1H), 8.08 (br s, 1H), 7.73 (s, 1H), 7.49 (d, 1H), 7.15 (d, 1H), 6.59 (t, 1H). $^{19}$F (376 MHz, DMSO-$d_6$)–128.7 (s).

Example 37

Preparation of 5-[7-(4-bromo-2-fluorophenylamino)-8-fluoroimidazo[1,2-a]pyridin-6-yl]-3H-[1,3,4]oxadiazol-2-one

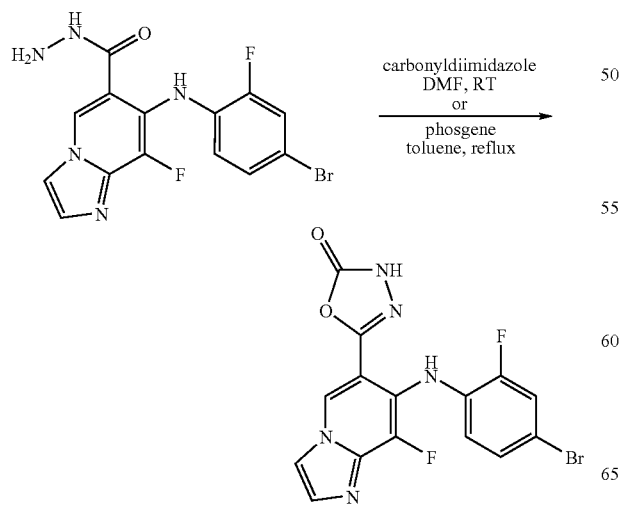

7-(4-bromo-2-fluorophenylamino)-8-fluoroimidazo[1,2-a]pyridine-6-carboxylic acid hydrazide (373 mg, 0.98 mmol), which was prepared according to Step A, Example 35, was dissolved into dimethylformamide (5 mL). Carbonyldiimidazole (166 mg, 1.02 mmol) was added as a solid. The reaction mixture was stirred for 1 hour at room temperature. It was then diluted with ethyl acetate and washed with water. The aqueous layer was back-extracted with ethyl acetate (3×). The combined organic layers were washed with saturated aqueous NaCl, dried over $Na_2SO_4$ and concentrated. Purification of the crude product was achieved by trituration with ethyl acetate and diethyl ether. The resulting solid was filtered, washed with diethyl ether, collected and dried under vacuum. The filtrate was concentrated and the trituration procedure was repeated. The solids were combined to yield the desired product (334 mg, 84%) as a yellow solid. MS ESI (+) m/z 408, 410 (M+, Br pattern) detected. $^1$H NMR (400 MHz, DMSO-$d_6$) δ 12.69 (br s, 1H), 9.05 (s, 1H), 8.11 (d, 1H), 7.89 (s, 1H), 7.67 (s, 1H), 7.51 (dd, 1H), 7.20 (d, 1H), 6.77 (m, 1H). $^{19}$F (376 MHz, DMSO-$d_6$)–128.9 (t, 1F), –139.5 (s, 1F).

Example 38

Preparation of [6-(5-Aminomethyl-[1,3,4]oxadiazol-2-yl)-8-chloroimidazo[1,2-a]pyridin-7-yl]-(4-bromo-2-fluorophenyl)-amine

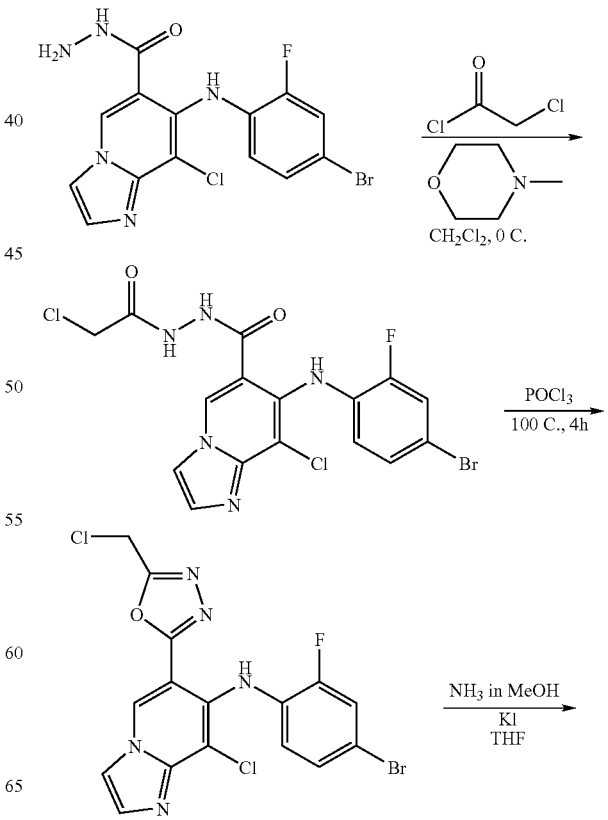

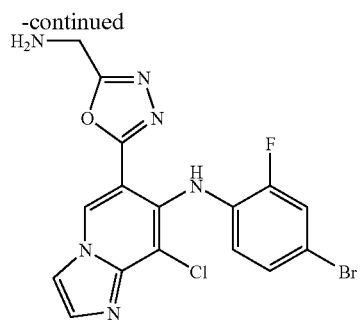

Step A: Preparation of 7-(4-bromo-2-fluorophenylamino)-8-chloroimidazo[1,2-a]pyridine-6-carboxylic acid N'-(2-chloroacetyl)-hydrazide. 7-(4-Bromo-2-fluorophenylamino)-8-chloroimidazo[1,2-a]pyridine-6-carboxylic acid hydrazide (100 mg, 0.25 mmol) of Step A, Example 35 was suspended in dichloromethane (2 mL) and 4-Me morpholine (0.040 mL, 0.36 mmol) was added. The mixture was cooled to 0° C. and then chloroacetyl chloride (0.029 mL, 0.36 mmol) was added dropwise. The reaction mixture was warmed to room temperature and stirred for 1 hour under N₂. Rinsed reaction mixture into a separatory funnel with a small amount of tetrahydrofuran and methanol and then diluted with ethyl acetate. The organic layer was washed with water and saturated aqueous NaCl, dried over Na₂SO₄ and concentrated. Purification of the crude product was achieved by flash column chromatography (20:1 dichloromethane/methanol) to yield the desired product (64 mg, 54%) as a yellow solid. MS ESI (+) m/z 474, 476 (M+, Cl, Br pattern) detected.

Step B: Preparation of (4-bromo-2-fluorophenyl)-[8-chloro-6-(5-chloromethyl-[1,3,4]oxadiazol-2-yl)-imidazo[1,2-a]pyridin-7-yl]-amine. 7-(4-Bromo-2-fluorophenylamino)-8-chloroimidazo[1,2-a]pyridine-6-carboxylic acid N'-(2-chloro-acetyl)-hydrazide (63 mg, 0.13 mmol) was suspended in POCl₃ (1 mL). The reaction mixture was heated to 100° C. for 8 hours, during which time it became a bright red solution. The reaction mixture was cooled to room temperature and the solvent evaporated under reduced pressure. The residue was dissolved in ethyl acetate and washed with saturated aqueous NaHCO₃, saturated aqueous NaCl, dried over Na₂SO₄ and concentrated. The crude product (38 mg, 62%) was used without further purification in next step. MS ESI (+) m/z 456, 458 (M+, Cl, Br pattern) detected.

Step C: Preparation of [6-(5-aminomethyl-[1,3,4]oxadiazol-2-yl)-8-chloroimidazo[1,2-a]pyridin-7-yl]-(4-bromo-2-fluorophenyl)-amine. (4-Bromo-2-fluoro-phenyl)-[8-chloro-6-(5-chloromethyl-[1,3,4]oxadiazol-2-yl)-imidazo[1,2-a]pyridin-7-yl]-amine (38 mg, 0.083 mmol) was dissolved in tetrahydrofuran (1 mL). Potassium iodide (14 mg, 0.083 mmol) was added and then ammonia (7 M solution in methanol, 0.30 mL, 2.08 mmol). The reaction mixture was stirred at room temperature for 16 hours. The solvent was removed under reduced pressure and the crude product was purified by flash column chromatography (gradient of 20:1 dichloromethane/methanol to 5:1) to yield the desired product (26 mg, 71%) as a yellow solid. MS ESI (+) m/z 437, 439 (M+, Cl, Br pattern) detected. ¹H NMR (400 MHz, DMSO-d₆) δ 9.35 (s, 1H), 8.33 (s, 1H), 8.17 (d, 1H), 7.70 (d, 1H), 7.51 (dd, 1H), 7.16 (d, 1H), 6.65 (t, 1H), 3.94 (s, 2H). ¹⁹F (376 MHz, DMSO-d₆)−128.3 (t).

Example 39

2-{5-[7-(4-Bromo-2-fluorophenylamino)-8-fluoroimidazo[1,2-a]pyridin-6-yl]-[1,3,4]oxadiazol-2-ylamino}-ethanol

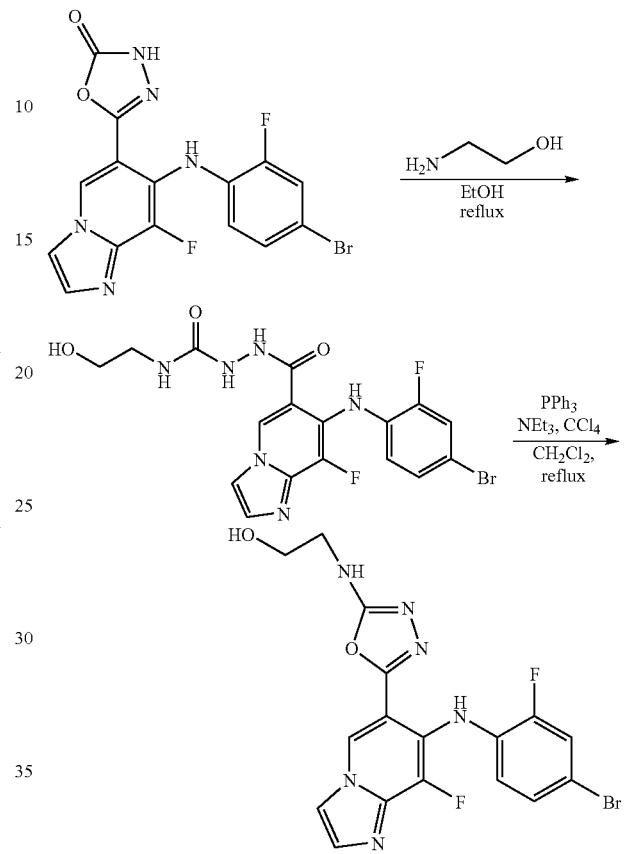

5-[7-(4-Bromo-2-fluoro-phenylamino)-8-fluoroimidazo[1,2-a]pyridin-6-yl]-3H-[1,3,4]oxadiazol-2-one of Example 37 was converted in two steps to the desired product following the procedures described in WO 04/056789. MS ESI (+) m/z 451, 453 (M+, Br pattern) detected. ¹H NMR (400 MHz, DMSO-d₆) δ 8.96 (s, 1H), 8.42 (s, 1H), 8.13 (d, 1H), 7.98 (t, 1H), 7.64 (d, 1H), 7.55 (dd, 1H), 7.26 (d, 1H), 6.87 (m, 1H), 4.78 (t, 1H), 3.56 (q, 2H), 3.30 (m, 2H). ¹⁹F (376 MHz, DMSO-d₆)−128.3 (t, 1F), −139.6 (s, 1F).

Example 40

N-{5-[7-(4-bromo-2-fluorophenylamino)-8-fluoroimidazo[1,2-a]pyridin-6-yl]-[1,3,4]oxadiazol-2-yl}-N'-methyl-ethane-1,2-diamine

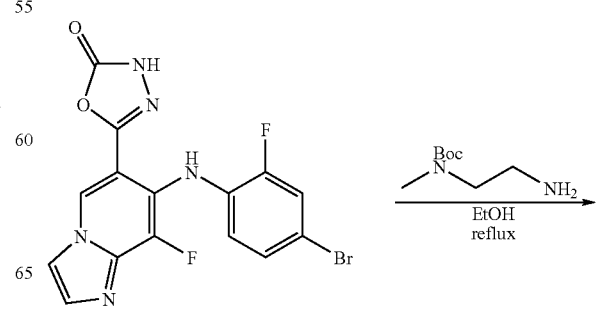

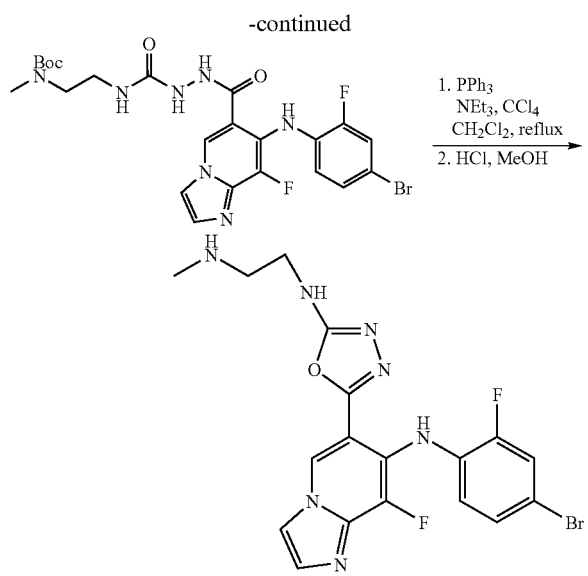

5-[7-(4-Bromo-2-fluorophenylamino)-8-fluoroimidazo[1,2-a]pyridin-6-yl]-3H-[1,3,4]oxadiazol-2-one of Example 37 was converted in three steps to the desired product, isolated as the HCl salt, following the procedures described in WO 04/056789. MS ESI (+) m/z 464, 466 (M+, Br pattern) detected. $^1$H NMR (400 MHz, DMSO-$d_6$) δ 9.26 (s, 1H), 8.95 (br s, 1H), 8.86 (br s, 2H), 8.39 (t, 1H), 8.25 (s, 1H), 7.93 (s, 1H), 7.64 (dd, 1H), 7.36 (d, 1H), 7.13 (m, 1H), 3.59 (q, 2H), 3.17 (m, 2H), 2.59 (t, 3H).

Example 41

Preparation of Hydroxylamines

Hydroxylamines useful for synthesizing compounds of the present invention may be prepared as follows:

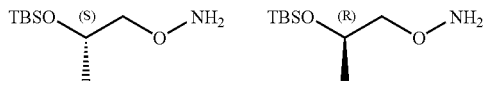

(i). (S)—O-[2-(tert-Butyl-dimethylsilanyloxy)-propyl]-hydroxylamine and (R)—O-[2-(tert-butyl-dimethylsilanyloxy)-propyl]-hydroxylamine Step A: Preparation of (S)-1-iodopropan-2-ol and (R)-1-Iodo-propan-2-ol. Acetic acid (12.8 mL, 224 mmol) and (S)-(−)- or (R)-(+)-propylene oxide (16.0 mL, 224 mmol) were added sequentially to a solution of lithium iodide (15.0 g, 112 mmol) in THF (200 mL) cooled to 0° C. The resulting thick suspension was allowed to warm to room temperature and stir for 16 hours. The suspension was diluted with ether, washed with water (3×), saturated NaHCO$_3$ (3×), brine, dried over Na$_2$SO$_4$, and concentrated to provide the desired product as a yellow liquid (19.5 g, 94%).

Step B: Preparation of (S)-tert-butyl-(2-iodo-1-methylethoxy)-dimethylsilane and (R)-tert-Butyl-(2-iodo-1-methylethoxy)-dimethylsilane. Pyridine (9.50 mL, 118 mmol) was added to a solution of (S)— or (R)-1-iodo-propan-2-ol (19.9 g, 107 mmol) and TBSCl (17.0 g, 113 mmol) in DMF (100 mL) cooled to 0° C. After stirring for two days, the solution was diluted with hexanes, washed with water (3×) and brine. The aqueous washes were back-extracted with 1:1 hexanes/ethyl acetate. The combined organic phases were dried over Na$_2$SO$_4$. Concentration provided the desired product as a yellow liquid (26.7 g, 83%).

Step C: Preparation of (S)-2-[2-(tert-Butyl-dimethylsilanyloxy)-propoxy]-isoindole-1,3-dione and (R)-2-[2-(tert-Butyl-dimethylsilanyloxy)-propoxy]-isoindole-1,3-dione. A solution of (S)— or (R)-tert-butyl-(2-iodo-1-methylethoxy)-dimethylsilane (22.7 g, 75.4 mmol), N-hydroxyphthalimide (14.8 g, 90.5 mmol) and diisopropylethylamine (15.8 mL, 90.5 mmol) was heated at 75° C. for 48 hours. The solution was cooled to room temperature, diluted with water and extracted with 1:1 hexanes/ethyl acetate (2×) and diethyl ether (2×). The combined organic extracts were washed with water (3×), brine (2×), dried over Na$_2$SO$_4$ and concentrated to a red liquid. The crude product was purified by flash column chromatography (dichloromethane) to provide the desired product as a yellow liquid (12.8 g, 50%).

Step D: Preparation of (S)—O-[2-(tert-Butyl-dimethylsilanyloxy)-propyl]-hydroxylamine or (R)—O-[2-(tert-Butyl-dimethylsilanyloxy)-propyl]-hydroxylamine. Methyl hydrazine (2.12 mL, 39.9 mmol) was added to a solution of (S)— or (R)-2-[2-(tert-butyl-dimethylsilanyloxy)-propoxy]-isoindole-1,3-dione (12.8 g, 38.0 mmol) in dichloromethane (100 mL) and the resulting suspension was stirred for 16 hours. The suspension was filtered to remove solids and the filtrate was concentrated to a yellow liquid. Flash column chromatography (2:1 hexanes/ethyl acetate) provided the desired product as a light yellow liquid (6.37 g, 82%). MS APCI (+) m/z 206 (M+1) detected. $^1$H NMR (400 MHz, CDCl$_3$) δ 5.44 (br s, 2H), 4.03 (m, 1H), 3.58 (m, 1H), 3.51 (m, 1H), 1.12 (d, 3H), 0.90 (s, 9H), 0.08 (s, 6H).

(ii). The following hydroxylamines were prepared similarly starting with the appropriate terminal epoxide. The isoindol-1,3-diones intermediates and the final hydroxylamines were purified by flash column chromatography.

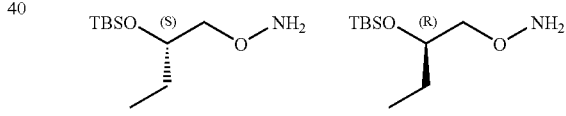

(S)-O-[2-(tert-butyl-dimethyl-silanyloxy)-butyl]-hydroxylamine and (R)-O-[2-(tert-butyl-dimethyl-silanyloxy)-butyl]-hydroxylamine (S)—O-[2-(tert-Butyl-dimethyl-silanyloxy)-butyl]-hydroxylamine and (R)—O-[2-(tert-butyl-dimethyl-silanyloxy)-butyl]-hydroxylamine were prepared from the homochiral terminal epoxides (S)— and (R)-1,2-epoxybutane respectively, which were obtained by kinetic resolution of 1,2-epoxybutane as described within J. Am. Chem. Soc., 2002, 124:1307. MS APCI (+) m/z 220 (M+1) detected. $^1$H NMR (400 MHz, CDCl$_3$) δ 5.41 (br s, 2H), 3.79 (m, 1H), 3.60 (m, 2H), 1.54 (m, 1H), 1.44 (m, 1H), 0.90 (s, 9H), 0.08 (s, 3H), 0.07 (s, 3H).

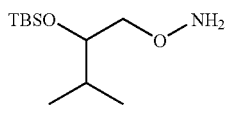

O-[2-(tert-Butyl-dimethylsilanyloxy)-3-methylbu-tyl]-hydroxylamine

MS APCI (+) m/z 234 (M+1) detected. $^1$H NMR (400 MHz, CDCl$_3$) δ 5.38 (br s, 2H), 3.64 (m, 3H), 1.75 (m, 1H), 0.90 (m, 15H), 0.08 (s, 3H), 0.05 (s, 3H).

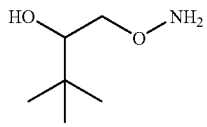

(iii). 1-Aminooxy-3,3-dimethylbutan-2-ol

Step A: Preparation of 2-(2-hydroxy-3,3-dimethylbutoxy)-isoindole-1,3-dione. To a solution of 3,3-dimethyl-1,2-epoxybutane (5.0 mL, 41.0 mmol) in DMF (100 mL) was added N-hydroxyphthalimide (8.03 g, 49.2 mmol) and triethylamine (6.90 mL, 49.2 mmol). The solution was heated at 75° C. for two days. The solution was cooled to room temperature, diluted with ethyl acetate and washed with water (2×), saturated potassium carbonate (3×), brine (2×), dried over Na$_2$SO$_4$ and concentrated to an orange solid. Purification using flash column chromatography (dichloromethane) provided the desired product as a white solid (1.50 g, 14%).

Step B: Preparation of 1-aminooxy-3,3-dimethylbutan-2-ol. To a solution of 2-(2-hydroxy-3,3-dimethylbutoxy)-isoindole-1,3-dione (1.47 g, 5.60 mmol) in dichloromethane (20 mL) cooled to 0° C. was added methylhydrazine (0.31 mL, 5.90 mmol). The white suspension was allowed to stir for 16 hours at room temperature. Diethyl ether (50 mL) was added and the solids were removed by filtration. The filtrate was concentrated, diluted with diethyl ether and the solids were removed by filtration. This procedure was repeated twice more and the final filtrate was concentrated to provide the desired product as a yellow liquid (0.643 g, 86%). $^1$H NMR (400 MHz, CDCl$_3$) δ 4.87 (br s, 2H), 3.85 (q, 1H), 3.58 (q, 2H), 0.93 (s, 9H).

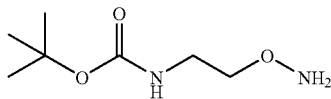

(iv). (2-Aminooxy-ethyl)-carbamic acid tert-butyl ester

Step A: Preparation of methanesulfonic acid 2-tert-butoxycarbonylamino-ethyl ester. Methanesulfonyl chloride (0.60 mL, 7.76 mmol) was added to a solution of (2-hydroxy-ethyl)-carbamic acid tert-butyl ester (1.04 g, 6.46 mmol) and triethylamine (1.35 mL, 9.70 mmol) in dichloromethane (35 mL) cooled to 0° C. The solution was stirred for one hour, after which time it was diluted with ethyl acetate, washed with saturated NaHCO$_3$ (2×), brine, dried over Na$_2$SO$_4$ and concentrated to a thick colorless liquid (1.37 g, 89%).

Step B: Preparation of [2-(1,3-dioxo-1,3-dihydroisoindol-2-yloxy)-ethyl]-carbamic acid tert-butyl ester. Added N-hydroxyphthalimide (1.12 g, 6.87 mmol) and triethylamine (0.96 mL, 6.87 mmol) to a solution of methanesulfonic acid 2-tert-butoxycarbonylaminoethyl ester (1.37 g, 5.73 mmol) in DMF (20 mL). The solution was heated to 50° C. for 16 hours after which time it was cooled to room temperature. The solution was diluted with ethyl acetate, washed with water (2×), saturated K$_2$CO$_3$, dried over Na$_2$SO$_4$ and concentrated to an orange solid (747 mg, 43%) which was taken on without purification.

Step C: Preparation of (2-aminooxyethyl)-carbamic acid tert-butyl ester. The synthesis of the title compound was carried out according to Step D of Example 41 (i) using [2-(1,3-dioxo-1,3-dihydroisoindol-2-yloxy)-ethyl]-carbamic acid tert-butyl ester as the starting material to provide 255 mg (71%) of the desired compound as a yellow liquid. $^1$H NMR (400 MHz, CDCl$_3$) δ 5.50 (br s, 2H), 5.02 (br s, 1H), 3.71 (t, 2H), 3.36 (q, 2H), 1.45 (s, 9H).

The following hydroxylamine was prepared similarly using (3-hydroxy-propyl)-carbamic acid tert-butyl ester as the starting material.

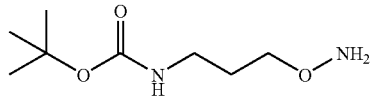

(3-Aminooxypropyl)-carbamic acid tert-butyl ester $^1$H NMR (400 MHz, CDCl$_3$) δ 5.41 (br s, 2H), 4.76 (br s, 1H), 3.73 (t, 2H), 3.21 (q, 2H), 1.78 (m, 2H), 1.44 (s, 9H).

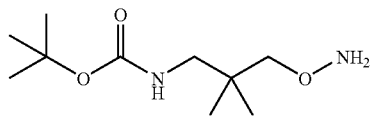

(v). (3-Aminooxy-2,2-dimethylpropyl)-carbamic acid tert-butyl ester

Step A: Preparation of (3-hydroxy-2,2-dimethylpropyl)-carbamic acid tert-butyl ester. Boc-anhydride (13.07 g, 59.9 mmol) in THF (10 mL) was added dropwise to a solution of 3-amino-2,2-dimethylpropan-1-ol (5.15 g, 49.9 mmol) and NaOH (2.40 g, 59.9 mmol) dissolved into 1:1 THF/water (50 mL). The solution was stirred at room temperature for 72 hours. The solution was concentrated under reduced pressure to about one half of the reaction volume. The remaining solution was acidified to pH 6 and was then extracted with ethyl acetate (2×). The organic extracts were washed with water, brine, dried over Na$_2$SO$_4$ and concentrated to provide the desired product (10.2 g, quantitative) as a white solid.

Step B: Preparation of [3-(1,3-dioxo-1.3-dihydroisoindol-2-yloxy)-2,2-dimethylpropyl]-carbamic acid tert-butyl ester. Diethylazodicarboxylate (8.26 mL, 52.4 mmol) was added to a solution of (3-hydroxy-2,2-dimethyl-propyl)-carbamic acid tert-butyl ester (10.2 g, 49.9 mmol), N-hydroxyphthalimide (8.15 g, 49.9 mmol) and triphenylphosphine (13.1 g, 49.9 mmol) in THF (200 mL). The solution was stirred at room temperature for 16 hours after which time it was diluted with dichloromethane and passed through a plug of silica gel, eluting with dichloromethane. The product containing fractions were concentrated to a yellow liquid, which was further purified by flash column chromatography (dichloromethane to 4:1 dichloromethane/ethyl acetate) to provide pure desired product (1.98 g, 11%) as a waxy white solid.

Step C: Preparation of (3-aminooxy-2,2-dimethylpropyl)-carbamic acid tert-butyl ester. The synthesis of the title compound was carried out according to STEP D of the Example 41 using [3-(1,3-dioxo-1,3-dihydroisoindol-2-yloxy)-2,2-dimethylpropyl]-carbamic acid tert-butyl ester as the starting material to provide 998 mg (80%) desired product as a pale yellow liquid. $^1$H NMR (400 MHz, CDCl$_3$) δ 5.45 (br s, 2H), 4.94 (br s, 1H), 3.44 (s, 2H), 3.03 (br d, 2H), 1.45 (s, 9H), 0.88 (s, 6H).

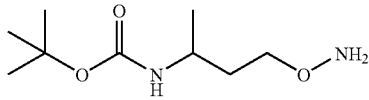

(vi). (3-Aminooxy-1-methylpropyl)-carbamic acid tert-butyl ester

Step A: Preparation of 3-aminobutan-1-ol. Lithium aluminum hydride (1.0 M in THF, 43.8 mL, 43.8 mmol) was added dropwise over one hour to a suspension of 3-aminobutyric acid (2.26 g, 21.9 mmol) in THF (100 mL) cooled to 0° C. The solution was then refluxed for 16 hours after which time it was cooled to 0° C. and quenched by the careful sequential addition of water (2 mL), 15% aqueous NaOH (2 mL) and water (2 mL). The mixture was stirred for 15 minutes and was filtered through CELITE, washing the filter pad with THF. Concentration of the filtrated provided the desired product (1.43 g, 73%) as a clear oil.

Step B: Preparation of (3-aminooxy-1-methylpropyl)-carbamic acid tert-butyl ester. The synthesis of the title compound was carried out according to Steps A, B and C of Example 41(iii) above using 3-aminobutan-1-ol as the starting material to provide 998 mg (80%) desired product as a pale yellow liquid. $^1$H NMR (400 MHz, CDCl$_3$) δ 5.39 (br s, 2H), 4.52 (br s, 1H), 3.72 (m, 3H), 1.70 (m, 2H), 1.43 (2, 9H), 1.14 (d, 3H).

(vii). The following hydroxylamines were prepared as described in WO 02/06213: O-(2-vinyloxyethyl)-hydroxylamine; O-(2-methoxyethyl)-hydroxylamine; 2-aminooxypropan-1-ol; 3-aminooxypropan-1-ol; 1-aminooxy-2-methylpropan-2-ol; 1-aminooxy-3-methoxypropan-2-ol; 3-aminooxy-1,1,1-trifluoropropan-2-ol; 2-aminooxy-2methylpropan-1-ol; (2-aminooxyethyl)-methylcarbamic acid tert-butyl ester; (R)—O-2,2-dimethyl-[1,3]dioxolan-4-ylmethyl)-hydroxylamine; (S)—O-2,2-dimethyl-[1,3]dioxolan-4-ylmethyl)-hydroxylamine.

(viii). The isoindole-1,3-dione intermediates of the following hydroxylamines are prepared from the appropriate alkyl halide and N-hydroxyphthalimide by the procedure described within *J. Heterocyclic Chemistry* 2000, 37, 827-830: O-propyl-hydroxylamine; O-isopropylhydroxylamine; O-cyclopropylmethylhydroxylamine. The isoindole-1,3-diones are deprotected by the procedure described above.

(ix). The following hydroxylamines were obtained from commercial sources: methoxyamine hydrochloride; O-ethylhydroxylamine hydrochloride; O-(tert-butyl)amine hydrochloride; O-allylamine hydrochloride.

Additional compounds suitable for use in the methods of the present invention are shown in FIGS. 13A-13G.

Biological Examples

Drugs

The preparation of AR-14 [7-(4-bromo-2-chlorophenylamino)-8-chloroimidazo[1,2-a]pyridine-6-carboxylic acid (2-hydroxyethoxy)-amide] and AR-13 [7-(4-bromo-2-fluorophenylamino)-8-chloroimidazo[1,2-a]pyridine-6-carboxylic acid (2-hydroxyethoxy)-amide] is described in the above Examples.

Example 42

Effect of AR-14 on Collagen-Induced Arthritis (CIA)

Type II collagen-induced arthritis (CIA) in rats is an experimental model of arthritis that has a number of pathologic, immunologic, and genetic features in common with rheumatoid arthritis.

Animals

Female Lewis rats (7-9 weeks of age; 8 per group for arthritis, 4 per group for normal control) were acclimated for 7 days after arrival.

Experimental Protocol

Acclimated animals were anesthetized with Isoflurane. The disease was induced by immunization of the rats with type II collagen (equal mixture of 4 mg/mL bovine type II collagen in 0.01 N acetic acid and Freund's incomplete adjuvant) by injection (day 0). On day 6, the rats were anesthetized again for the second collagen injection. Each animal received 300 μL of the collagen mixture on days 0 and 6, which was spread over 3 sites on the back.

Caliper measurements of normal (pre-disease) right and left ankle joints were taken on day 9 post-collagen injection. On days 10-11, onset of arthritis occurred and rats were randomized into treatment groups. Randomization into each group was done after ankle joint swelling was established in at least one hind paw.

Once enrolled in the treatment groups, treatment with once daily oral dosing of AR-14 (1, 3, 10, 30 or 60 mg/kg) or indomethacin (1 mg/kg) was initiated. Animals receiving vehicle or compound were enrolled and daily dosing was initiated using a volume of 5 mL/kg for oral solutions. ENBREL (etanercept) treatment was on days 11 and 15 (10 mg/kg) by subcutaneous administration. Rats were weighed on days 11-18 and caliper measurements of ankles were taken every day. Final body weights were taken on day 19. On day 19, animals were euthanized, both hind paws and knees were removed, hind paws were weighed and then (with knees) placed in formalin.

Following 1-2 days in fixative and then 4-5 days in decalcifier, the ankle joints and knees were processed, embedded, sectioned and stained with toluidine blue.

Scoring of Joints

A clinical scoring index was used to assess disease progression. Collagen arthritic ankles and knees were given scores of 0-5 for inflammation, pannus formation and bone resorption according to the criteria in Tables 1-7.

TABLE 1

Knee and Ankle Inflammation

| Score | Evaluation |
|---|---|
| 0 | Normal |
| 1 | Minimal infiltration of inflammatory cells in periarticular tissue |
| 2 | Mild infiltration |
| 3 | Moderate infiltration with moderate edema |
| 4 | Marked infiltration with marked edema |
| 5 | Severe infiltration with severe edema |

TABLE 2

Ankle Pannus (Emphasis on tibiotarsal joint)

| Score | Evaluation |
|---|---|
| 0 | Normal |
| 1 | Minimal infiltration of pannus in cartilage and subchondral bone |

TABLE 2-continued

Ankle Pannus (Emphasis on tibiotarsal joint)

| Score | Evaluation |
|---|---|
| 2 | Mild infiltration (<¼ of tibia at edges) |
| 3 | Moderate infiltration (¼ to ⅓ of tibia affected, smaller tarsals affected) |
| 4 | Marked infiltration (½-¾ of tibia affected, destruction of smaller tarsals) |
| 5 | Severe infiltration (>¾ of tibia affected, severe distortion of overall architecture) |

TABLE 3

Knee Pannus

| Score | Evaluation |
|---|---|
| 0 | Normal |
| 1 | Minimal infiltration of pannus in cartilage and subchondral bone |
| 2 | Mild infiltration (extends over up to ¼ of surface or subchondral area of tibia or femur) |
| 3 | Moderate infiltration (extends over >¼ but <½ of surface or subchondral area of tibia or femur) |
| 4 | Marked infiltration (extends over ½ to ¾ of tibial or femoral surface) |
| 5 | Severe infiltration (covers >¾ of surface) |

TABLE 4

Cartilage Damage (Ankle)

| Score | Evaluation |
|---|---|
| 0 | Normal |
| 1 | Minimal to mild loss of toluidine blue staining with no obvious chondrocyte loss or collagen disruption |
| 2 | Mild loss of toluidine blue staining with focal mild (superficial) chondrocyte loss and/or collagen disruption and full destruction of tibia <¼ of surface, mild changes in smaller tarsals |
| 3 | Moderate loss of toluidine blue staining with multifocal moderate (depth to middle zone) chondrocyte loss and/or collagen disruption, ¼ to ⅓ of tibia affected by full thickness destruction, smaller tarsals affected to ½-¾ depth |
| 4 | Marked loss of toluidine blue staining with multifocal marked (depth to deep zone) chondrocyte loss and/or collagen disruption, ½-¾ of tibia with full thickness destruction, destruction of smaller tarsals |
| 5 | Severe diffuse loss of toluidine blue staining with multifocal severe (depth to tide mark) chondrocyte loss and/or collagen disruption |

TABLE 5

Cartilage Damage (Knee, emphasis on femoral condyles)

| Score | Evaluation |
|---|---|
| 0 | Normal |
| 1 | Minimal to mild loss of toluidine blue staining with no obvious chondrocyte loss or collagen disruption |
| 2 | Mild loss of toluidine blue staining with focal mild (superficial) chondrocyte loss and/or collagen disruption |
| 3 | Moderate loss of toluidine blue staining with multifocal to diffuse moderate (depth to middle zone) chondrocyte loss and/or collagen disruption |
| 4 | Marked loss of toluidine blue staining with multifocal to diffuse marked (depth to deep zone) chondrocyte loss and/or collagen disruption |
| 5 | Severe diffuse loss of toluidine blue staining with multifocal severe (depth to tide mark) chondrocyte loss and/or collagen disruption on both femur and tibia |

TABLE 6

Bone Resorption (Ankle)

| Score | Evaluation |
|---|---|
| 0 | Normal |
| 1 | Minimal, i.e., small areas of resorption, not readily apparent on low magnification, rare osteoclasts |
| 2 | Mild, i.e., more numerous areas of resorption, not readily apparent on low magnification, osteoclasts more numerous, <¼ of tibia at edges is resorbed |
| 3 | Moderate, i.e., obvious resorption of medullary trabecular and cortical bone without full thickness defects in cortex, loss of some medullary trabeculae, lesion apparent on low magnification, osteoclasts more numerous, ¼ to ⅓ of tibia affected, smaller tarsals affected |
| 4 | Marked, i.e., full thickness defects in cortical bone, often with distortion of profile of remaining cortical surface, marked loss of medullary bone, numerous osteoclasts, ½-¾ of tibia affected, destruction of smaller tarsals |
| 5 | Severe, i.e., full thickness defects in cortical bone, often with distortion of profile of remaining cortical surface, marked loss of medullary bone, numerous osteoclasts, >¾ of tibia affected, severe distortion of overall architecture |

TABLE 7

Bone Resorption (Knee)

| Score | Evaluation |
|---|---|
| 0 | Normal |
| 1 | Minimal, i.e., small areas of resorption, not readily apparent on low magnification, rare osteoclasts |
| 2 | Mild, i.e., more numerous areas of resorption, definite loss of subchondral bone involving ¼ of tibial or femoral surface (medial or lateral) |
| 3 | Moderate, i.e., obvious resorption of subchondral bone involving >¼ but <½ of tibial or femoral surface (medial or lateral) |
| 4 | Marked, i.e., obvious resorption of subchondral bone involving ≧½ but <¾ of tibial or femoral surface (medial or lateral) |
| 5 | Severe, i.e., distortion of entire joint due to destruction involving >¾ of tibial or femoral surface (medial or lateral) |

Statistical Analysis

Clinical data for ankle joint diameter were analyzed by determining the area under the dosing curve (AUC). For calculation of AUC, the daily measurements of ankle joints (using a caliper) for each rat were entered into Microsoft Excel and the area between the treatment days after the onset of disease to the termination day was computed. Means for each group were determined and percent inhibition from arthritis controls was calculated by comparing values for treated and normal animals. Data were analyzed by the Mann Whitney or Student's t test. Paw weights and histologic parameters (mean±SE) for each group were analyzed for differences using the Mann Whitney or Student's t test. In both cases, significance was set at p≦0.05.

Percent inhibition of paw weight and AUC was calculated using the following formula:

$$\% \text{ Inhibition} = A - (B/A) \times 100$$

wherein A=(Mean Disease Control−Mean Normal) and B=(Mean Treated−Mean Normal).

Results

Figure 1:
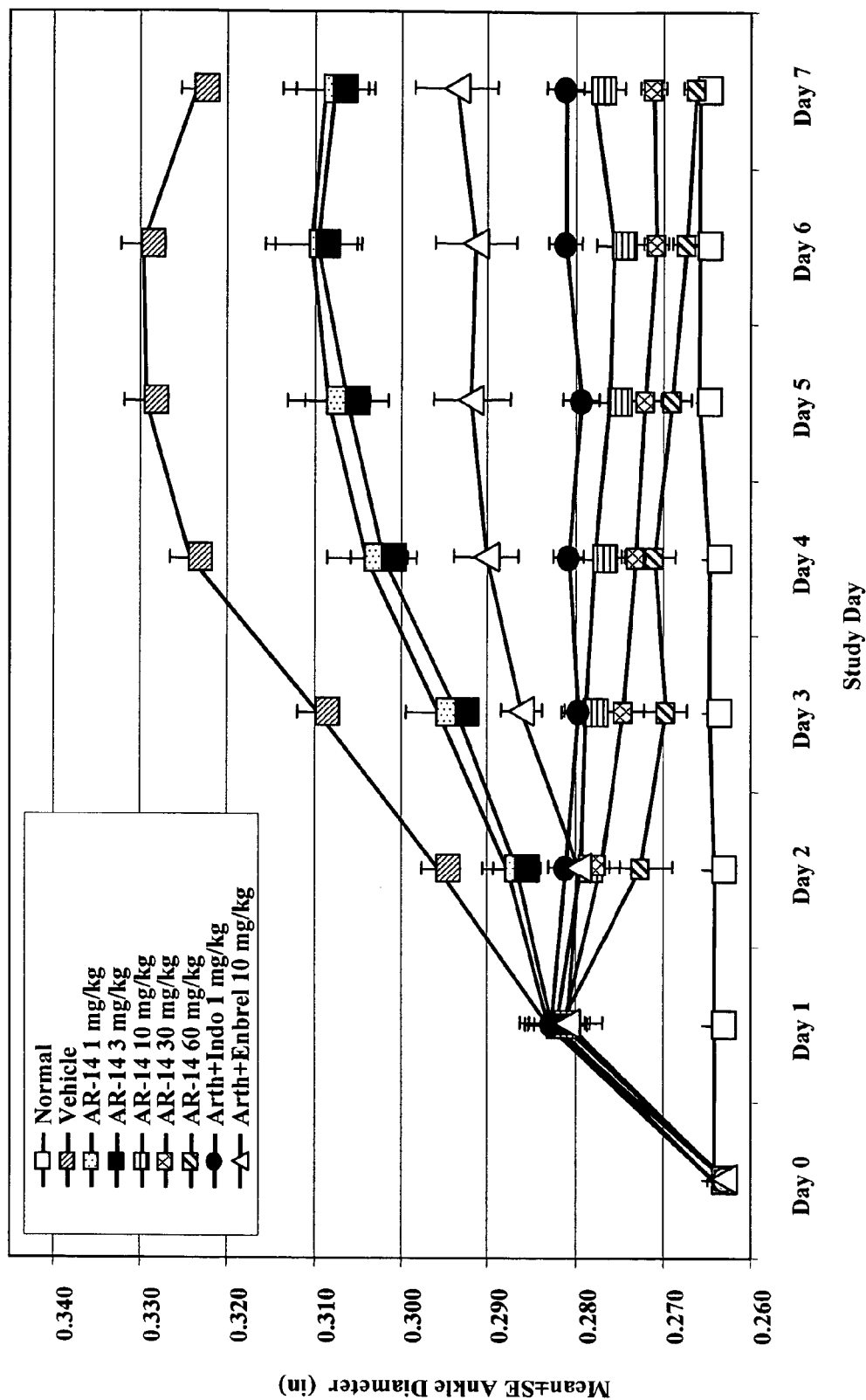
FIG. 1 is a graph representing mean ankle diameter in inches for established type II collagen-induced arthritis in rats with respect to time in days after dosing with AR-14 (1 mg/kg, 3 mg/kg, 10 mg/kg, 30 mg/kg or 60 mg/kg), indomethacin (1 mg/kg), ENBREL (etanercept) (10 mg/kg), or vehicle.

AR-14 was well tolerated at all doses administered. FIG. 1 shows the effects of AR-14 on paw diameter over 7 days. AR-14 significantly inhibited ankle swelling compared to vehicle control at all doses tested. AR-14 stopped the progression of established disease at 10 mg/kg and caused improvement to normal at 60 mg/kg. The activity of AR-14 at 10 mg/kg was equivalent to indomethacin (Arth+Indo) and better than that of ENBREL (etanercept) (Arth+Enbrel) in this model.

Figure 2:
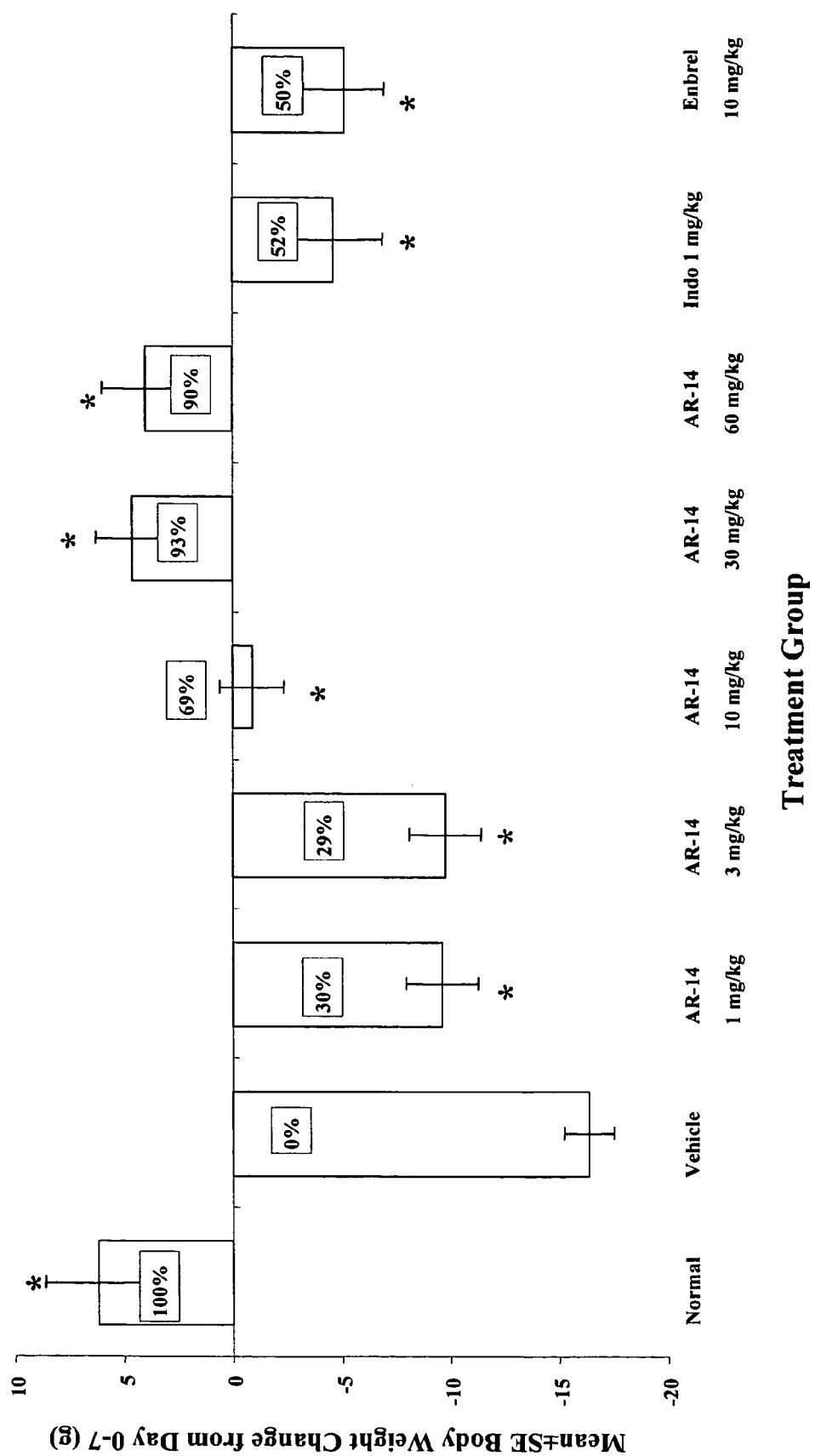
FIG. 2 is a bar graph representing the mean change in body weight in grams for established type II collagen-induced arthritis in rats after 7 days after dosing with AR-14 (1 mg/kg, 3 mg/kg, 10 mg/kg, 30 mg/kg or 60 mg/kg), indomethacin (1 mg/kg), ENBREL (etanercept) 10 mg/kg), or vehicle, relative to normal body weight change.

FIG. 2 shows the effects of AR-14 versus indomethacin (Indo) and ENBREL (etanercept) on body weight after 7 days. AR-14 significantly inhibited body weight loss at all doses tested with near normal body weights observed at doses of 30 and 60 mg/kg. The $ED_{50}$ was 4.57 mg/kg.

Figure 3:
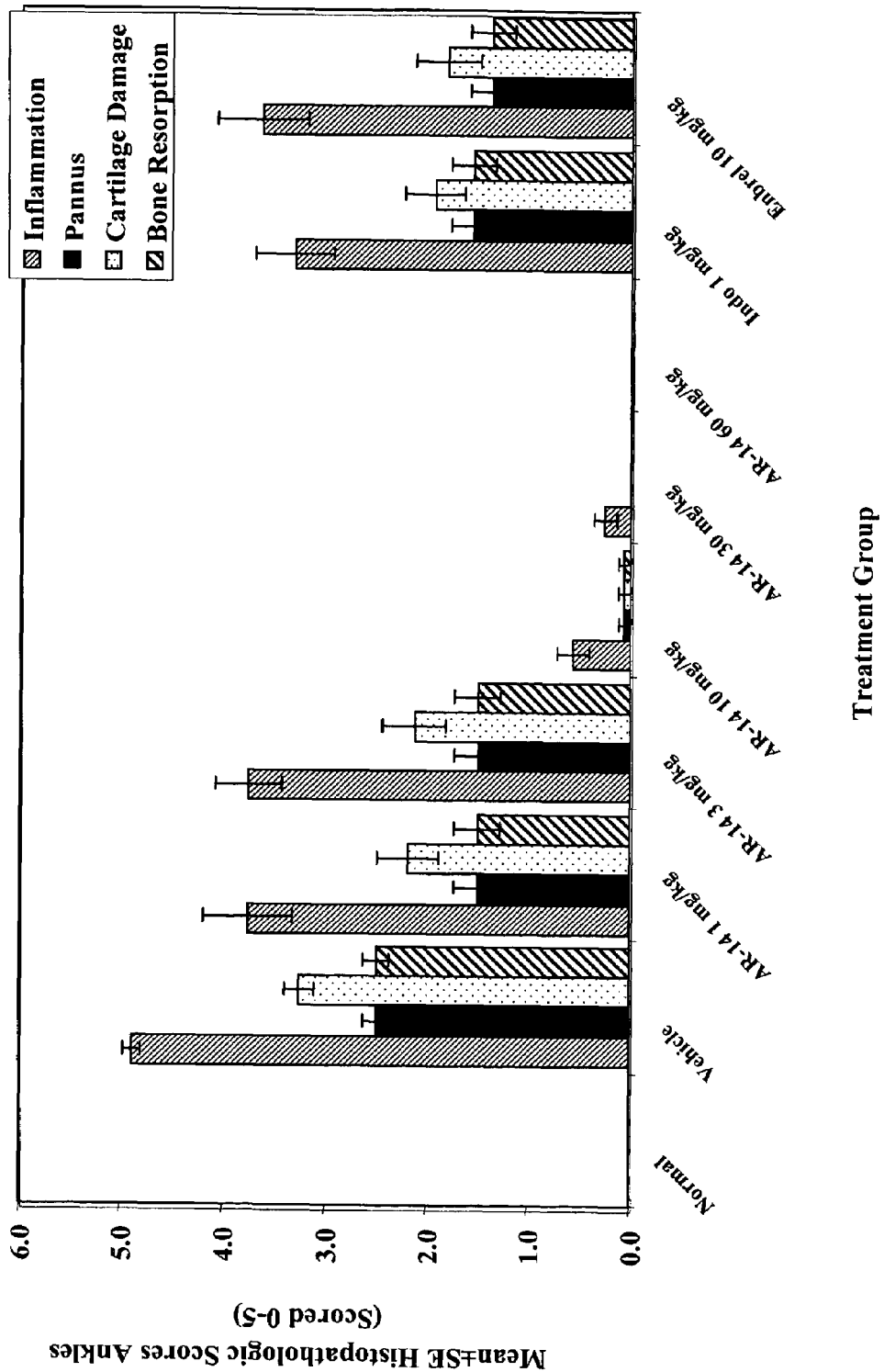
FIG. 3 is a bar graph representing the mean histopathologic score for ankles for established type II collagen-induced arthritis in rats after 7 days as a function of the dosage of AR-14 (1 mg/kg, 3 mg/kg, 10 mg/kg, 30 mg/kg or 60 mg/kg), indomethacin (1 mg/kg), ENBREL (etanercept) (10 mg/kg) or vehicle. Parameters scored were inflammation, pannus, cartilage damage and bone resorption.

FIG. 3 shows the effects of AR-14 versus indomethacin (Indo) and ENBREL (etanercept) on ankle histopathology after 7 days. AR-14 significantly inhibited pannus formation, cartilage damage and bone resorption at 1 and 3 mg/kg. Near normal joints with minimal inflammation at 10 mg/kg was observed, which is significantly better than indomethacin or ENBREL(etanercept) at this dose.

In summary, AR-14 significantly inhibited the progression of established arthritis at doses as low as 10 mg/kg and significantly inhibited joint destruction at a dose of 1 mg/kg.

Example 43

Effect of AR-14 on Adjuvant-Induced Arthritis (AIA)

Animals

Male Lewis rats (7-9 weeks of age; 8 per group for arthritis, 4 per group for normal control) were acclimated for 7 days after arrival.

Experimental Protocol

Acclimated animals were randomized into groups by body weight and then anesthetized with Isoflurane and given lipoidal amine (LA) in Freund's complete adjuvant (100 μL injection of 7 mg LA, intradermal administration at the base of the tail, Day 0).

Caliper measurements of normal (pre-disease) right and left ankle joints were taken on day 7 post-adjuvant injection. On day 8, dosing began for vehicle and AR-14 treatment groups. Methotrexate treatment (0.075 mg/kg) began on day 0 prior to adjuvant injection.

Once enrolled in the treatment group, treatment with once daily oral doses of AR-14 (1, 3, 10 or 30 mg/kg) was initiated. AR-14 was well tolerated at all doses administered. Animals receiving vehicle or compound were enrolled and daily dosing was initiated using a volume of 5 mL/kg for oral solutions on days 8-14. Rats were weighed on days 8-14 and caliper measurements of ankles were taken every day. Final body weights and caliper measurements of ankles and paws were taken on day 15. On day 15, animals were euthanized, both hind paws were removed, and the hind paws weighed and then placed in formalin for histopathologic analyses. Spleens were also removed, weighed and placed in formalin for histopathologic analyses.

Results

Figure 4:
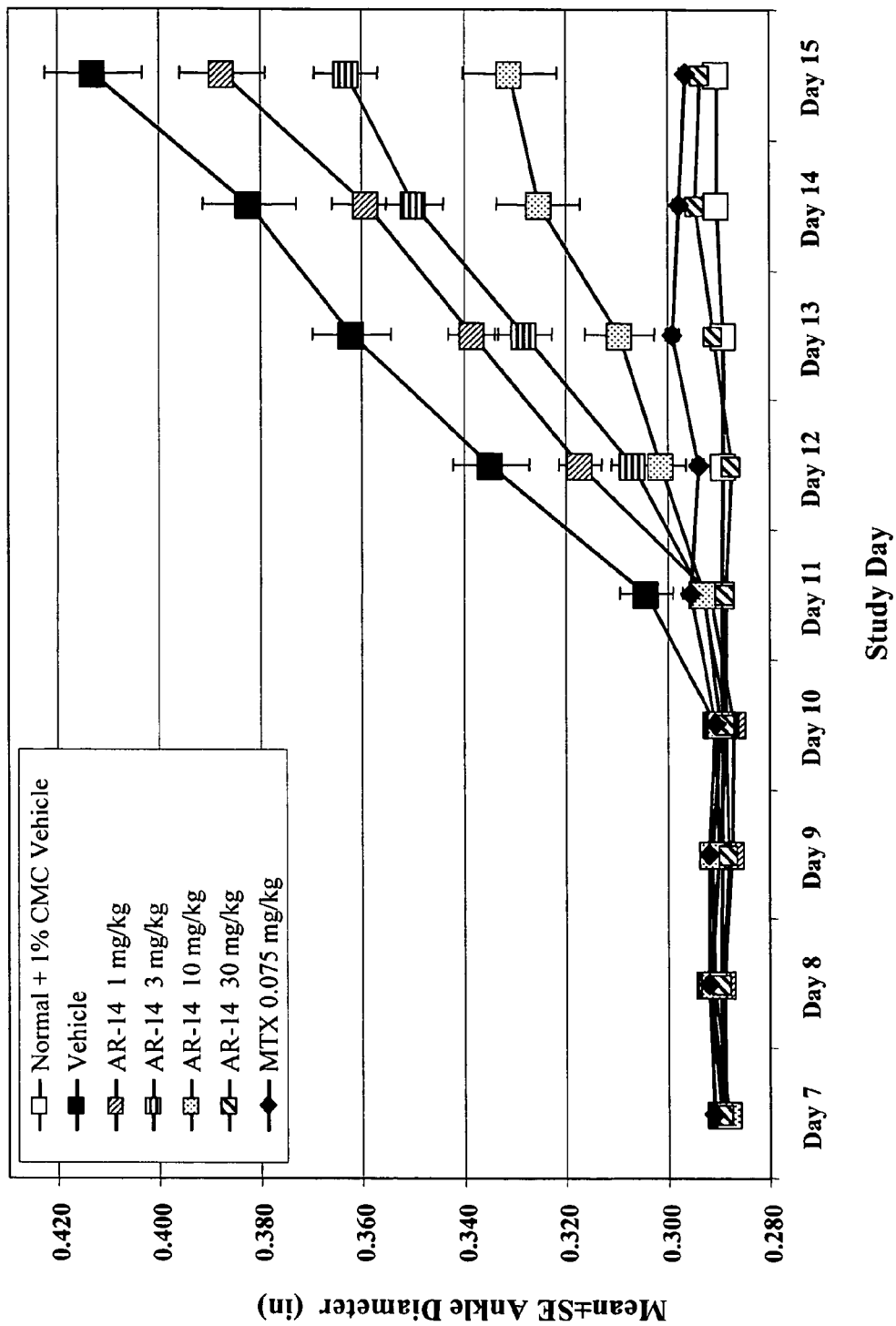
FIG. 4 is a graph representing mean ankle diameter in inches for adjuvant-induced arthritis in rats as a function of time in days after dosing with AR-14 (1 mg/kg, 3 mg/kg, 10 mg/kg, or 30 mg/kg), methotrexate (0.075 mg/kg), or vehicle, relative to normal ankle diameter.

FIG. 4 shows the effects of AR-14 versus methotrexate (MTX) on paw diameter over 15 days. AR-14 significantly inhibited ankle swelling compared to vehicle control at all doses tested. AR-14 stopped the progression of established disease and causes improvement to normal at 30 mg/kg. The activity of AR-14 at 30 mg/kg was equivalent to methotrexate in this model.

Figure 5:
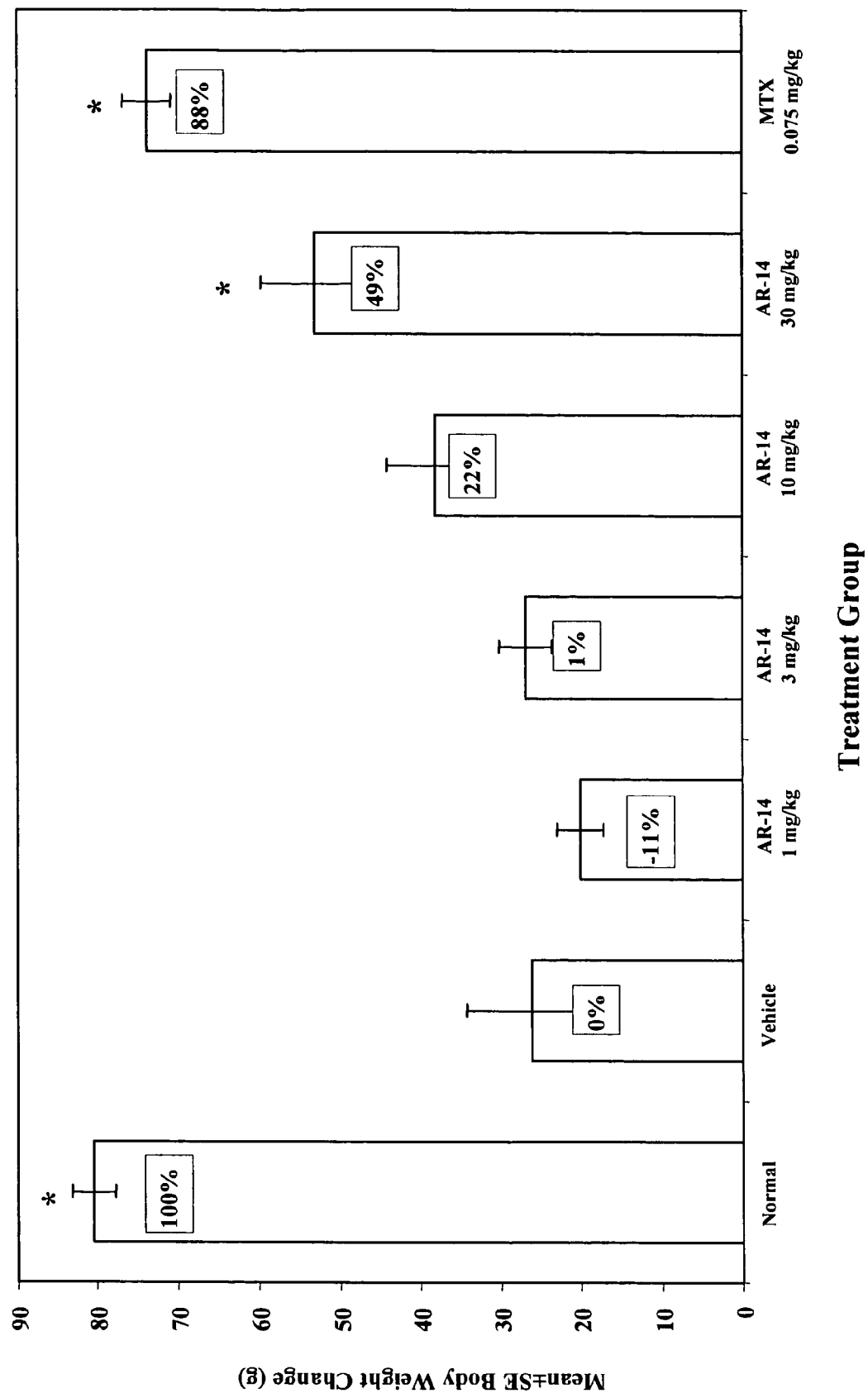
FIG. 5 is a bar graph representing mean change in body weight in grams for adjuvant-induced arthritis in rats after 15 days as a function of dosage of AR-14 (1 mg/kg, 3 mg/kg, 10 mg/kg, or 30 mg/kg), methotrexate (0.075 mg/kg), or vehicle, relative to normal body weight.

FIG. 5 shows the effects of AR-14 versus methotrexate (MTX) on body weight after 15 days. AR-14 significantly inhibited body weight loss at 30 mg/kg.

Figure 6:
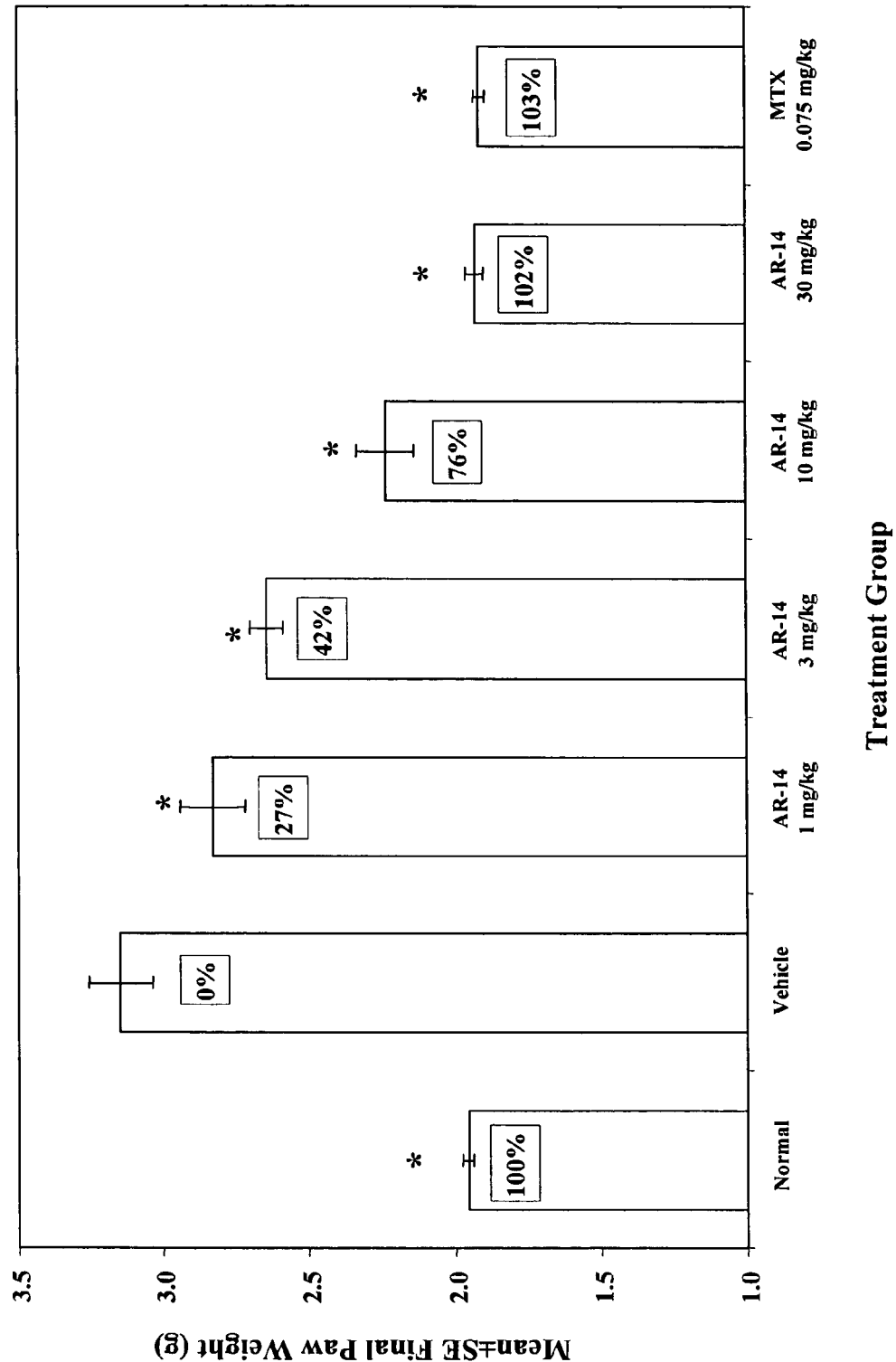
FIG. 6 is a bar graph representing mean paw weight in grams for adjuvant-induced arthritis in rats after 15 days as a function of the dosage of AR-14 (1 mg/kg, 3 mg/kg, 10 mg/kg, or 30 mg/kg), methotrexate (0.075 mg/kg), or vehicle, relative to normal paw weight.

FIG. 6 shows the effects of AR-14 versus methotrexate (MTX) on paw weight after 15 days. AR-14 significantly inhibited paw weight gain (edema/inflammation) at all doses compared to vehicle control. Near normal joints with minimal inflammation were observed at 30 mg/kg (comparable to methotrexate).

Figure 7:
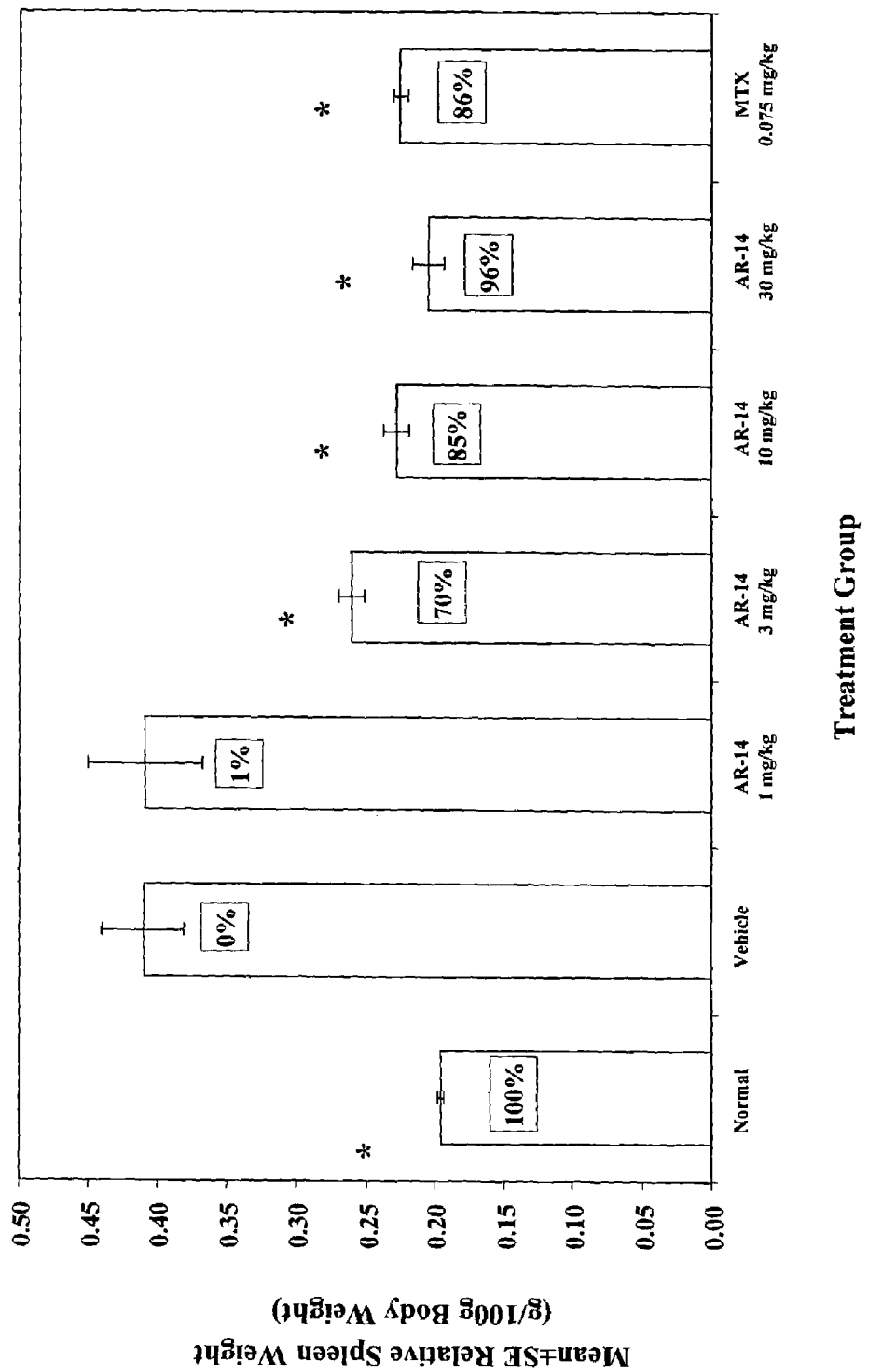
FIG. 7 is a bar graph representing mean relative spleen weight in grams for adjuvant-induced arthritis in rats after 15 days as a function of the dosage of AR-14 (1 mg/kg, 3 mg/kg, 10 mg/kg, or 30 mg/kg), methotrexate (0.075 mg/kg), or vehicle, relative to normal spleen weight.

FIG. 7 shows the effects of AR-14 versus methotrexate (MTX) on relative spleen weight after 15 days. AR-14 significantly inhibited splenomegaly at 3, 10 and 30 mg/kg. At the latter two doses, this inhibition is comparable to that seen with methotrexate.

Example 44

Effect of AR-14 on Indomethacin-Induced Inflammatory Bowel Disease (IBD)

This study evaluated AR-14 (PO, QD) in a model of Crohn's disease (indomethacin induced intestinal injury) in rats to determine if beneficial effects could be detected in this IBD model.

Experimental Protocol

Rats received two subcutaneous administrations of indomethacin (7.5 mg/kg, in 5% $NaHCO_3$) spaced 24 hours apart. Rats received once daily oral doses of vehicle, AR-14 (1, 3, 10 or 30 mg/kg) or dexamethasone (0.1 mg/kg). Rats were euthanized and evaluated for effects of treatment at day 4 post-initial indomethacin injection. Body weights were taken as well as intestinal weights per 10 cm of area at risk.

Scoring of Intestines

A clinical scoring index (Table 8) was used to assess disease progression. Intestines were scored for gross lesions and multiple sections of gut taken for histology (5 sections per rat spaced equally along area at risk).

TABLE 8

Gross Scoring Criteria

| Score | Evaluation |
|---|---|
| 0 | Normal |
| 1 | Minimal thickening |
| 2 | Mild to moderate small intestinal/mesenteric thickening |
| 3 | Moderate thickening with 1 or more definite adhesions that would be easy to separate |
| 4 | Marked thickening with numerous hard to separate adhesions |
| 5 | Severe intestinal lesion resulting in death |

Histologic Scoring Criteria

Five equally spaced sections from area at risk were scored for necrosis and inflammation (0,0) (1,3) etc., according to the criteria in Tables 9 and 10.

TABLE 9

Necrosis

| Score | Percent of lesion with necrosis |
|---|---|
| 0 | Normal |
| 1 | 10% |
| 2 | 10-25% |
| 3 | 25-50% |
| 4 | 50-75% |
| 5 | 75-100% |

TABLE 10

| Score | Evaluation |
|---|---|
| | Inflammation |
| 0 | Normal |
| 1 | Minimal in mesentery and muscle or lesion |
| 2 | Mild in mesentery and muscle or lesion |
| 3 | Moderate in mesentery and muscle or lesion |
| 4 | Marked in lesion |
| 5 | Severe in lesion |

Results

Figure 8:
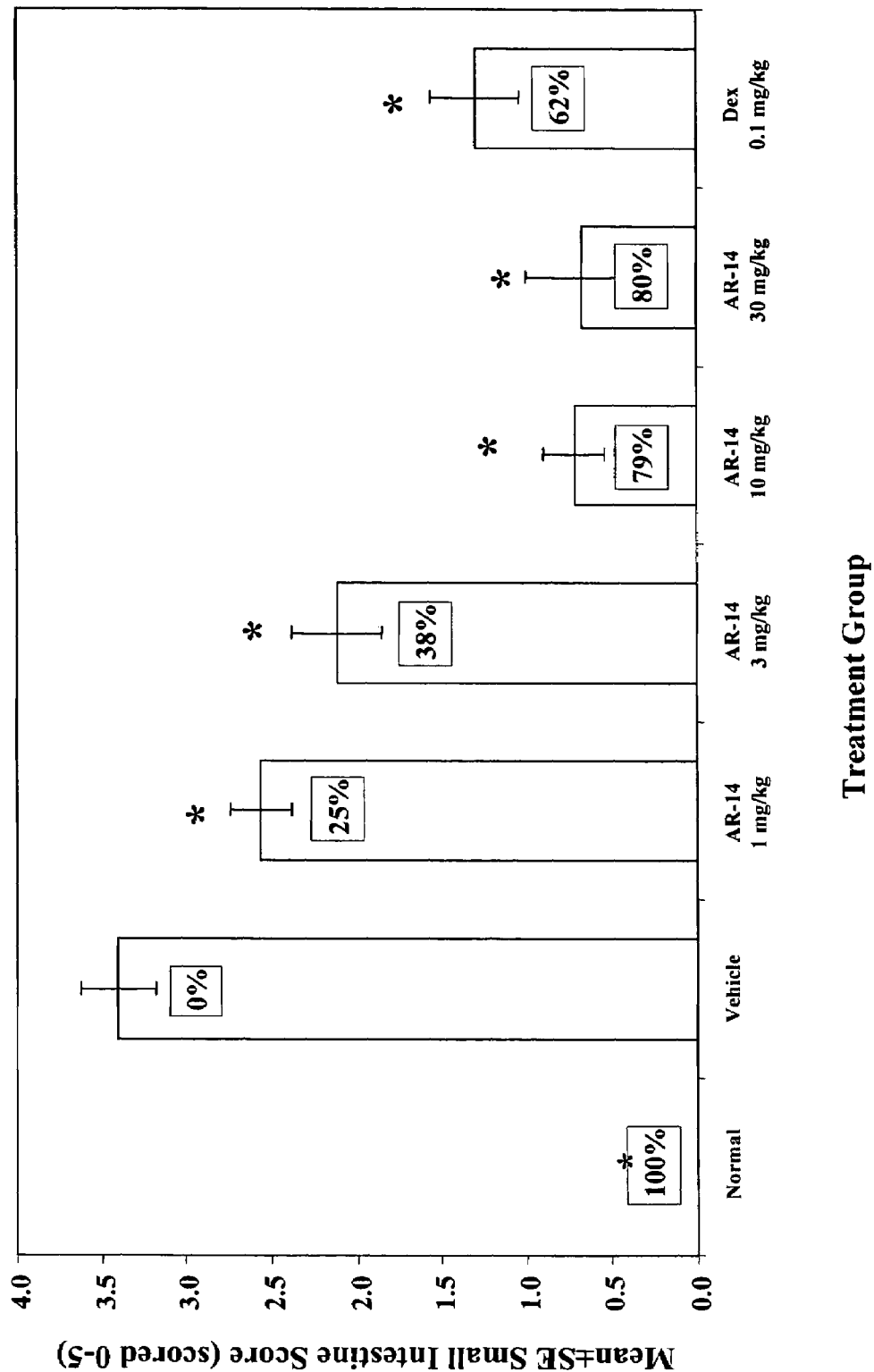
FIG. 8 is a bar graph representing gross lesion score (small intestine) for indomethacin-induced IBD in rats after 4 days as a function of the dosage of AR-14 (1 mg/kg, 3 mg/kg, 10 mg/kg, or 30 mg/kg), dexamethasone (0.1 mg/kg), or vehicle, relative to normal gross lesion score.

FIG. 8 shows the effects of AR-14 versus dexamethasone (Dex) on small intestine score after 4 days. AR-14 significantly inhibited gross lesion score at all doses. At the 10 and 30 mg/kg doses, AR-14 was significantly better than dexamethasone at inhibiting gross lesion score.

Figure 9:
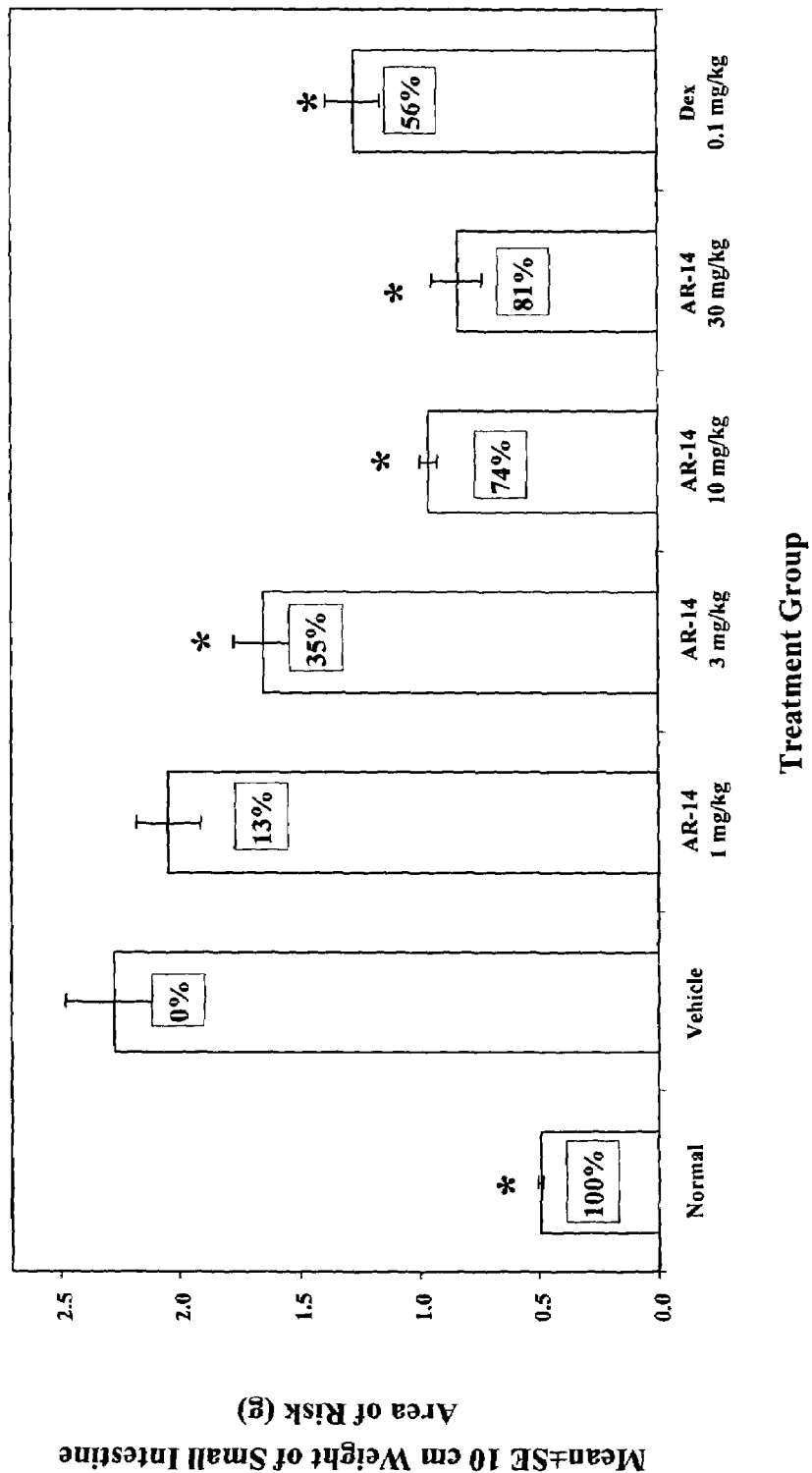
FIG. 9 is a bar graph representing mean small intestine weight for indomethacin-induced IBD in rats after 4 days as a function of the dosage of AR-14 (1 mg/kg, 3 mg/kg, 10 mg/kg, or 30 mg/kg), dexamethasone (0.1 mg/kg), or vehicle, relative to normal small intestine weight.

FIG. 9 shows the effects of AR-14 versus dexamethasone (Dex) on small intestine weight after 4 days. AR-14 significantly inhibited small intestine weight gain as a result of edema/inflammation at the 3, 10 and 30 mg/kg doses. At the 10 and 30 mg/kg doses, AR-14 was significantly better than dexamethasone at inhibiting intestinal inflammation and edema as well as small intestine necrosis and inflammation.

Figure 10:
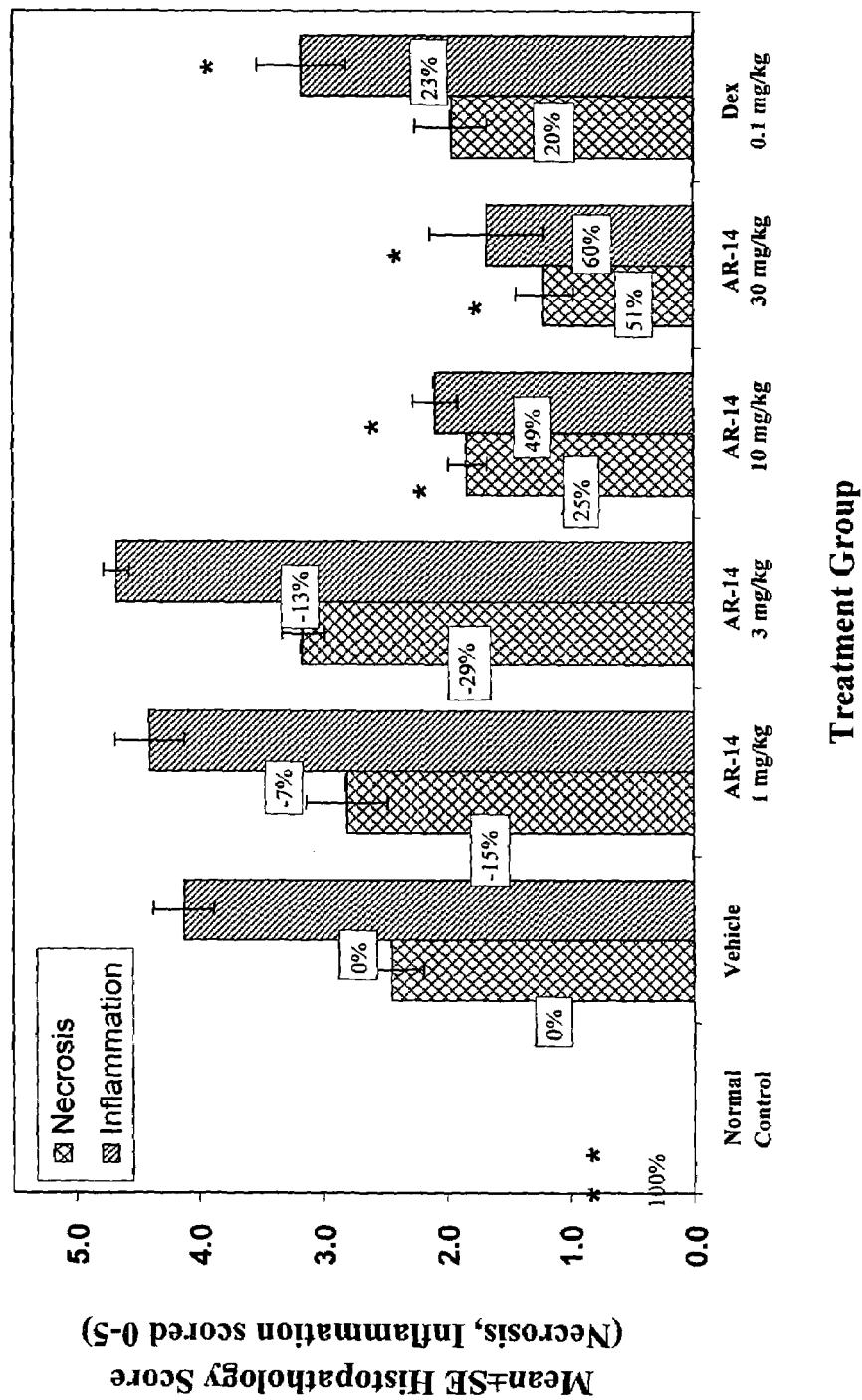
FIG. 10 is a bar graph representing the mean histopathology score for indomethacin-induced IBD in rats after 4 days as a function of the dosage of AR-14 (1 mg/kg, 3 mg/kg, 10 mg/kg, or 30 mg/kg), dexamethasone (0.1 mg/kg), or vehicle, relative to normal histopathology score. Parameters scored were necrosis and inflammation.

FIG. 10 shows the effects of AR-14 versus dexamethasone (Dex) on the histopathology of the gut (necrosis and inflammation scored). At 30 mg/kg, AR-14 was significantly more efficacious than dexamethasone in this model.

In summary, a significant inhibition of disease (gut score and weight and microscopic changes) was seen with once daily dosing of AR-14 at 10 mg/kg.

Example 45

Effect of AR-13 and AR-14 on Carrageenan Paw Edema

The rat carrageenan paw edema model of inflammation was utilized to evaluate the effectiveness of AR-13 and AR-14 in ameliorating swelling and inflammation.

Animals

Male Lewis rats (7-9 weeks of age; 10 per group) were acclimated for at least 7 days after arrival.

Experimental Protocol

Acclimated animals were randomized into groups by body weight. Animals were treated orally with AR-13 or AR-14 (3, 10 or 30 mg/kg) or with a positive control (indomethacin, 2 mg/kg). After 2 hours, the animals were anesthetized with Isoflurane and given an intradermal injection of 1.2% carrageenan into the right hind footpad. Four hours after the carrageenan injection, the animals were sacrificed with carbon dioxide inhalation and both paws were removed at the medial malleolus and weighed. The difference in weight between the right (carrageenan) and left (normal) paws was calculated.

Results

Figure 11:
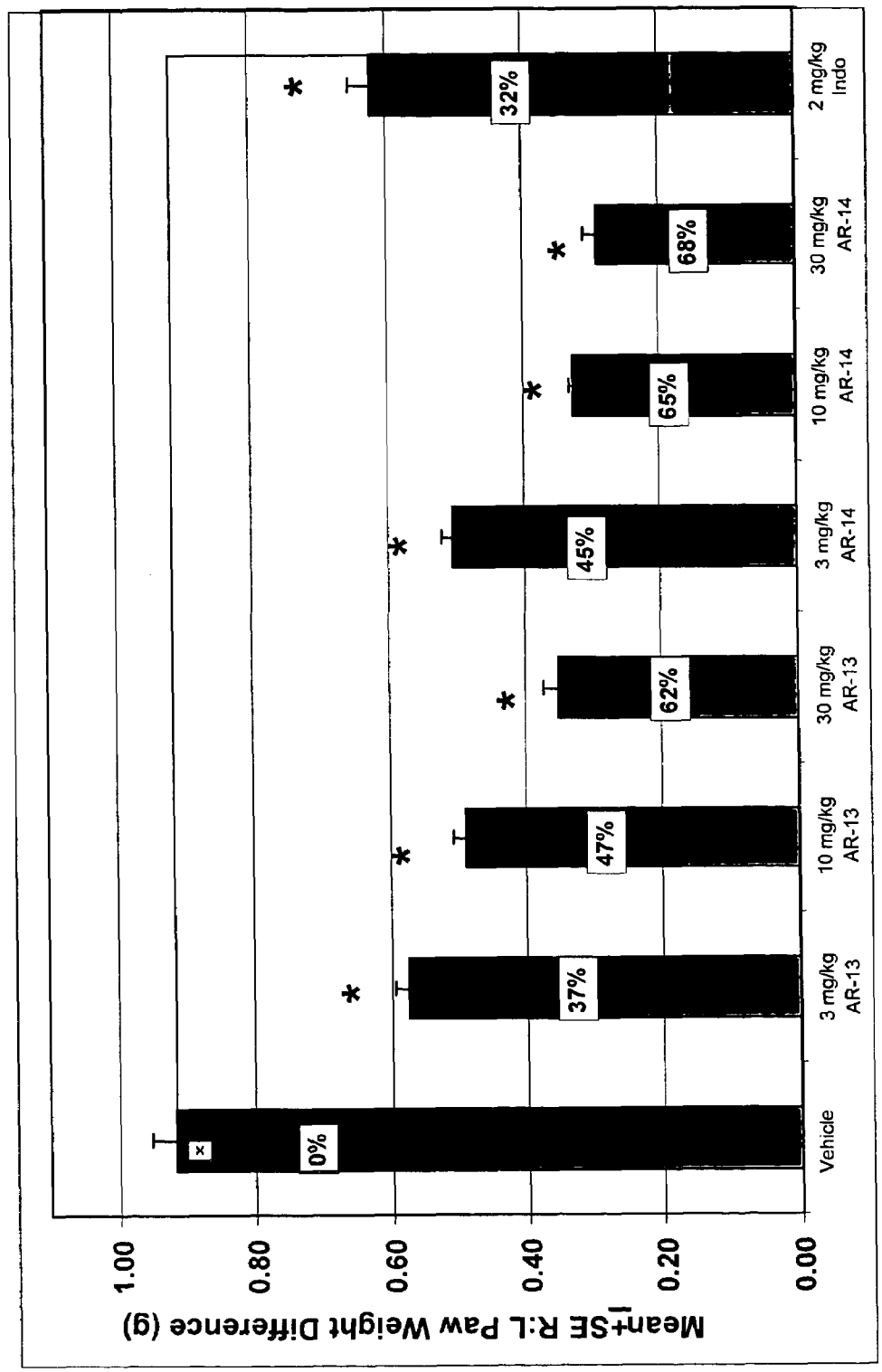
FIG. 11 is a bar graph representing mean paw weight in grams in the carrageenan paw edema model in rats as a function of the dosage of AR-13 (3 mg/kg, 10 mg/kg or 30 mg/kg), AR-14 (3 mg/kg, 10 mg/kg, or 30 mg/kg), indomethacin (2 mg/kg), or vehicle, relative to normal paw weight.

FIG. 11 shows the effects of AR-13 and AR-14 versus indomethacin on paw weight. Treatment with AR-13 or AR-14 significantly inhibited paw weight at 3, 10 and 30 mg/kg. The $ED_{50}$ for AR-14 was about 4 mg/kg, while the $ED_{50}$ for AR-13 was about 10 mg/kg. The activity seen with both of these compounds was superior to indomethacin.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A method for treating an inflammatory disease or disorder, said method comprising administering to a mammal in need of such treatment an effective amount of compound of the Formula II

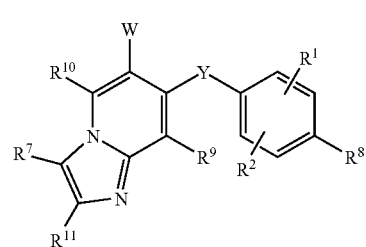

II or a solvate, metabolite or pharmaceutically acceptable salt thereof, wherein:

$R^1$, $R^2$, $R^7$, $R^8$, $R^9$, $R^{10}$ and $R^{11}$ are independently hydrogen, halo, cyano, nitro, trifluoromethyl, difluoromethoxy, trifluoromethoxy, azido, —$OR^3$, —$C(O)R^3$, —$C(O)OR^3$, $NR^4C(O)OR^6$, —$OC(O)R^3$, —$NR^4SO_2R^6$, —$SO_2NR^3R^4$, —$NR^4C(O)R^3$, —$C(O)NR^3R^4$, —$NR^5C(O)NR^3R^4$, —$NR^5C(NCN)NR^3R^4$, —$NR^3R^4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —$S(O)_j$($C_1$-$C_6$ alkyl), —$S(O)_j(CR^4R^5)_m$-aryl, aryl, arylalkyl, heteroaryl, heteroarylalkyl, heterocyclyl, heterocyclylalkyl, —$O(CR^4R^5)_m$-aryl, —$NR^4(CR^4R^5)_m$-aryl, —$O(CR^4R^5)_m$-heteroaryl, —$NR^4(CR^4R^5)_m$-heteroaryl, —$O(CR^4R^5)_m$-heterocyclyl or —$NR^4(CR^4R^5)_m$-heterocyclyl, wherein any of said alkyl, alkenyl, alkynyl, cycloalkyl, aryl, arylalkyl, heteroaryl, heteroarylalkyl, heterocyclyl and heterocyclylalkyl portions are optionally substituted with one or more groups independently selected from oxo, halo, cyano, nitro, trifluoromethyl, difluoromethoxy, trifluoromethoxy, azido, —$NR^4SO_2R^6$, —$SO_2NR^3R^4$, —$C(O)R^3$, —$C(O)OR^3$, —$OC(O)R^3$, —$NR^4C(O)OR^6$, —$NR^4C(O)R^3$, —$C(O)NR^3R^4$, —$NR^3R^4$, —$NR^5C(O)NR^3R^4$, —$NR^5C(NCN)NR^3R^4$, —$OR^3$, aryl, heteroaryl, arylalkyl, heteroarylalkyl, heterocyclyl and heterocyclylalkyl;

or $R^7$ and $R^{11}$ together with the atoms to which they are attached form a 4 to 10 membered saturated, unsaturated, or partially saturated carbocyclic or heterocyclic ring, wherein any of said saturated, unsaturated, partially saturated carbocyclic or heterocyclic rings are optionally substituted with one or more groups independently selected from halo, cyano, nitro, trifluoromethyl, difluoromethoxy, trifluoromethoxy, azido, —NR'SO₂R"", —SO₂NR'R", —C(O)R', —C(O)OR', —OC(O)R', —NR'C(O)OR"", —NR'C(O)R", —C(O)NR'R", —SO₂R"", —NR'R", —NR'C(O)NR"R''', —NR'C(NCN)NR"R''', —OR', aryl, heteroaryl, arylalkyl, heteroarylalkyl, heterocyclyl and heterocyclylalkyl;

$R^3$ is hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, heterocyclylalkyl, phosphate or an amino acid residue, wherein any of said alkyl, alkenyl, alkynyl, cycloalkyl, cycloalkylalkyl, aryl, arylalkyl, heteroaryl, heteroarylalkyl, heterocyclyl and heterocyclylalkyl portions are optionally substituted with one or more groups independently selected from oxo, halo, cyano, nitro, trifluoromethyl, difluoromethoxy, trifluoromethoxy, azido, —NR'SO$_2$R"", —SO$_2$NR'R", —C(O)R', —C(O)OR', —OC(O)R', —NR'C(O)OR"", —NR'C(O)R", —C(O)NR'R", —SR', —S(O)R"", —SO$_2$R"", —NR'R", —NR'C(O)NR"R''', —NR'C(NCN)NR"R''', —OR', aryl, heteroaryl, arylalkyl, heteroarylalkyl, heterocyclyl and heterocyclylalkyl, or $R^3$ and $R^4$ together with the atom to which they are attached form a 4 to 10 membered saturated, unsaturated, or partially saturated heterocyclic ring, wherein any of said saturated, unsaturated, or partially saturated heterocyclic rings are optionally substituted with one or more groups independently selected from halo, cyano, nitro, trifluoromethyl, difluoromethoxy, trifluoromethoxy, azido, —NR'SO$_2$R"", —SO$_2$NR'R", —C(O)R', —C(O)OR', —OC(O)R', —NR'C(O)OR"", —NR'C(O)R", —C(O)NR'R", —SO$_2$R"", —NR'R", —NR'C(O)NR"R''', —NR'C(NCN)NR'R''', —OR', aryl, heteroaryl, arylalkyl, heteroarylalkyl, heterocyclyl and heterocyclylalkyl;

R', R" and R''' are independently hydrogen, lower alkyl, lower alkenyl, aryl or arylalkyl;

R"" is lower alkyl, lower alkenyl, aryl or arylalkyl, or any two of R', R", R''' and R"" together with the atoms to which they are attached form a 4 to 10 membered saturated, unsaturated, or partially saturated heterocyclic ring, wherein any of said alkyl, alkenyl, aryl, arylalkyl saturated, unsaturated, or partially saturated heterocyclic rings are optionally substituted with one or more groups independently selected from halo, cyano, nitro, trifluoromethyl, difluoromethoxy, trifluoromethoxy, azido, aryl, heteroaryl, arylalkyl, heteroarylalkyl, heterocyclyl, and heterocyclylalkyl;

$R^4$ and $R^5$ are independently hydrogen or $C_1$-$C_6$ alkyl;

$R^6$ is trifluoromethyl, $C_1$-$C_{10}$ alkyl, $C_3$-$C_{10}$ cycloalkyl, aryl, arylalkyl, heteroaryl, heteroarylalkyl, heterocyclyl or heterocyclylalkyl, wherein any of said alkyl, cycloalkyl, aryl, arylalkyl, heteroaryl, heteroarylalkyl, heterocyclyl and heterocyclylalkyl portions are optionally substituted with one or more groups independently selected from oxo, halo, cyano, nitro, trifluoromethyl, difluoromethoxy, trifluoromethoxy, azido, —NR'SO$_2$R"", —SO$_2$NR'R", —C(O)R', —C(O)OR', —OC(O)R', —NR'C(O)OR"", —NR'C(O)R", —C(O)NR'R", —SO$_2$R"", —NR'R', —NR'C(O)NR"R''', —NR'C(NCN)NR"R''', —OR', aryl, heteroaryl, arylalkyl, heteroarylalkyl, heterocyclyl, and heterocyclylalkyl;

W is heteroaryl, heterocyclyl, —C(O)OR$^3$, —C(O)NR$^3$R$^4$, —C(O)NR$^4$OR$^3$, C(O)R$^4$OR$^3$, —C(O)(C$_3$-C$_{10}$ cycloalkyl), —C(O)(C$_1$-C$_{10}$ alkyl), —C(O)(aryl), C(O)(heteroaryl), —C(O)(heterocyclyl), —CONH(SO$_2$)CH$_3$ or —CR$^3$OR$^3$, wherein any of said heteroaryl, heterocyclyl, —C(O)OR$^3$, —C(O)NR$^3$R$^4$, —C(O)NR$^4$OR$^3$, —C(O)R$^4$OR$^3$, —C(O)(C$_3$-C$_{10}$ cycloalkyl), —C(O)(C$_1$-C$_{10}$ alkyl), —C(O)(aryl), —C(O)(heteroaryl), —C(O)(heterocyclyl), —CONH(SO$_2$)CH$_3$ and —CR$^3$OR$^3$ are optionally substituted with one or more groups independently selected from —NR$^3$R$^4$, —OR$^3$, —R$^2$, C$_1$-C$_{10}$ alkyl, C$_2$-C$_{10}$ alkenyl and C$_2$-C$_{10}$ alkynyl, wherein any of said alkyl, alkenyl, and alkynyl portions are optionally substituted with 1 or more groups independently selected from —NR$^3$R$^4$ and —OR$^3$;

m is 0, 1, 2, 3, 4 or 5;

j is 0, 1 or 2; and

Y is a linker.

2. The method of claim 1, wherein said inflammatory disorder is rheumatoid arthritis.

3. The method of claim 2, wherein said compound is administered in an amount between about 1 and 60 mg per kilogram of body weight of said mammal.

4. The method of claim 3, wherein said amount is between about 1 and 10 mg per kilogram of body weight of said mammal.

5. The method of claim 4, wherein said amount is between about 1 and 3 mg per kilogram of body weight of said mammal.

6. The method of claim 1, wherein said compound is administered once a day.

7. The method of claim 1, wherein said compound is administered orally.

8. The method of claim 1, wherein said compound is 7-(4-bromo-2-chlorophenylamino)-8-chloroimidazo[1,2-a]pyridine-6-carboxylic acid (2-hydroxyethoxy)-amide.

9. The method of claim 1, wherein said compound is 7-(4-bromo-2-fluorophenylamino)-8-chloroimidazo[1,2-a]pyridine-6-carboxylic acid (2-hydroxyethoxy)-amide.

\* \* \* \* \*